US009556419B2

(12) United States Patent
Minke

(10) Patent No.: US 9,556,419 B2
(45) Date of Patent: Jan. 31, 2017

(54) REVERSE GENETICS SCHMALLENBERG VIRUS VACCINE COMPOSITIONS, AND METHODS OF USE THEREOF

(71) Applicant: Merial Limited, Duluth, GA (US)

(72) Inventor: Jules Maarten Minke, Corbas (FR)

(73) Assignee: MERIAL INC., Duluth, GA (US)

( * ) Notice: Subject to any disclaimer, the term of this patent is extended or adjusted under 35 U.S.C. 154(b) by 0 days.

(21) Appl. No.: 14/204,248

(22) Filed: Mar. 11, 2014

(65) Prior Publication Data

US 2014/0314807 A1 Oct. 23, 2014

Related U.S. Application Data

(60) Provisional application No. 61/776,833, filed on Mar. 12, 2013.

(51) Int. Cl.
| | |
|---|---|
| *A61K 39/12* | (2006.01) |
| *C12N 7/00* | (2006.01) |
| *A61K 39/00* | (2006.01) |

(52) U.S. Cl.
CPC ............... *C12N 7/00* (2013.01); *A61K 39/12* (2013.01); *A61K 2039/5252* (2013.01); *A61K 2039/552* (2013.01); *A61K 2039/55505* (2013.01); *A61K 2039/55566* (2013.01); *A61K 2039/55577* (2013.01); *C12N 2760/12021* (2013.01); *C12N 2760/12034* (2013.01)

(58) Field of Classification Search
None
See application file for complete search history.

(56) References Cited

U.S. PATENT DOCUMENTS

2014/0274762 A1* 9/2014 Manuguerra et al. ............ 506/9

FOREIGN PATENT DOCUMENTS

| EP | 1217031.1 | * | 6/2012 | ............ C07K 14/175 |
|---|---|---|---|---|
| WO | WO2009/128043 A1 | * | 10/2009 | ............ A61K 39/15 |
| WO | WO2013/181270 A1 | * | 12/2013 | ............ C07K 14/175 |
| WO | WO 2013/181270 A1 | | 12/2013 | |

OTHER PUBLICATIONS

Varela et al. (PLoS, Jan. 10, 2013, vol. 9, p. 1-13).*
Accession Nos. JX853179, 2013.*
Accession Nos. JX853180, 2013.*
Accession Nos. JX853181, 2013.*
Van der Brom et al. (Tijdschr Diergeneeskd. Feb. 2012 p. 102-111).*
Schmidt (Science, Mar. 2, 2012, vol. 335, p. 1028-1029).*
Lytle and Sagripanti, Journal of Virology, 2005.*
"Abstracts 6th Annual Meeting Epizone "Schmallenberg Virus" Jun. 15, 2012" [Online] Jun. 15, 2012 (Jun. 15, 2012), XP055136296, Retrieved from the Internet: URL:http://www.epizone-eu.netfupload mm/2/ efe/8358656e-bfc8-41a6-9aa3-6ee516efa334_6 th%20EPIZONE%20Schmallenberg%20Virus%0Abs tracts%20Booklet July%202012b%20.pdf> [retrieved on Aug. 25, 2014].
"Schmallenberg virus genes for nucleocapsid protein and non-structural protein, segment S, genomic RNA, isolate BH80/11-4", EMBL, Mar. 26, 2012 (Mar. 26, 2012), XP002700360, [retrieved on Jan. 16, 2012].
"Schmallenberg virus gene for M polyprotein, segment M, genomic RNA, isolate BH80/11-4", EMBL, Mar. 26, 2012 (Mar. 26, 2012), XP002700361, [retrieved on Jan. 16, 2012].
"Schmallenberg virus RdRp gene for RNA-dependent RNA polymerase, segment L, genomic RNA, isolate BH80/11-4", EMBL, Mar. 26, 2012 (Mar. 26, 2012), XP002700362, [retrieved on Jan. 16, 2012].
Elliott R M et al: "Establishment of a reverse genetics system for Schmallenberg virus, a newly emerged orthobunyavirus in Europe", Journal of General Virology, Society for General Microbiology, Spencers Wood, GB, vol. 94, No. Part 4, Dec. 19, 2012.
Wernike Kerstin et al: "Inactivated Schma 11 enberg virus prototype vaccines", Vaccine, vol. 31, No. 35, May 23, 2014 (May 23, 2014), pp. 3558-3563, XP028683950.
Silke Hechinger et al: "Single immunization with an inactivated vaccine protects sheep from Schmallenberg virus infection", Veterinary Research, vo 1 • 45, No. 1, Jan. 1, 2014 (Jan. 1, 2014), p. 79, XP055136280.
"Bovilis SBV The World's First SBV Vaccination", 1•Jul. 2, 2013 (Jul. 21, 2013), XP055136264, Retrieved from the Internet: URL:http://www.westpointfarmvets.co.ukflib rary/files/ BovilisSBV.pdf [retrieved on Aug. 25, 2014].
Claude Hamers et al: "Demonstration of Efficacy Against Challenge of an Inactivated Schmallenberg Vaccine in Cattle Introduction", 1• Nov. 2013 (Nov. 1, 2013), XP055136271, Retrieved from the Internet: URL:http://www.buiatricsforum.com/Pres 2013/C. Hamers.pdf [retrieved on Aug. 25, 2014].
Toon Rosseel et al: "DNase SISPA—Next Generation Sequencing Confirms Schmallenberg Virus in Belgian Field Samples and Identifies Genetic Variation in Europe", PLOS One, vol. 7, No. 7, Jul. 1, 2012 (Jul. 1, 2012), p. e41967, XP055136202.
Hoffmann B. et al. *Novel Orthobunyavirus in Cattle, Europe, 2011.* Emerging Infectious Diseases • www.cdc.gov/eid • vol. 18, No. 3, Mar. 2012.
European Centre for Disease Prevention and Control, Stockholm, 2011. *Risk Assessment. New Orthobunyavirus isolated from infected cattle and small livestock—potential implications for human health.*
Saeed MF, Li L, Wang H, Weaver SC, Barrett AD. Phylogeny of the Simbu serogroup of the genus Bunyavirus. J Gen Virol. 2001;82:2173-81.

* cited by examiner

*Primary Examiner* — Agnieszka Boesen
(74) *Attorney, Agent, or Firm* — Judy Jarecki-Black; Chad Kitchen; Merial Inc.

(57) ABSTRACT

The present invention relates to compositions comprising replication defective Schmallenberg virus vaccines, methods of producing the vaccines, and the administration of such vaccines to animals, including ovines and bovines. The invention further relates to methods for providing long-term protective immunity against Schmallenberg in animals, including ovines and bovines.

9 Claims, 13 Drawing Sheets

S segment +T7/Ribo/T7t:

SEQ ID NO:1 T7 minimal promotor
TAATACGACTCACTATAG

SEQ ID NO:2 ("S" 5' UTR)
AGTAGTGAACTCCACTATTAACTACAGAAAT

SEQ ID NO:3 ("S" ORF nucleotide)
ATGTCAAGCCAATTCATTTTTGAAGATGTACCACAACGGAATGCAGCTACATTTAACCCGGAGGTCGGGT
ATGTGGCATTTATTGGTAAGTATGGGCAACAACTCAACTTCGGTGTTGCTAGAGTCTTCTTCCTCAACCA
GAAGAAGGCCAAGATGGTCCTACATAAGACGGCACAACCAAGTGTCGATCTTACTTTTGGTGGGGTCAAA
TTTACAGTGGTTAATAACCATTTTCCCCAATATGTCTCAAATCCTGTGCCAGACAATGCCATTACACTTC
ACAGGATGTCAGGATATCTAGCACGTTGGATTGCTGATACATGCAAGGCTAGTGTCCTCAAACTAGCTGA
AGCTAGTGCTCAGATTGTCATGCCCCTTGCTGAGGTTAAGGGATGCACCTGGGCCGATGGTTATACAATG
TATCTTGGATTTGCACCTGGGGCCGAAATGTTCCTTGATGCTTTTGACTTCTATCCACTAGTTATTGAAA
TGCATAGGGTCCTCAAGGACAATATGGATGTAAATTTTATGAAAAAAGTCCTCCGCCAACGCTATGGAAC
AATGACTGCTGAAGAATGGATGACTCAGAAAATAACAGAAATAAAAGCTGCTTTTAATTCTGTTGGACAG
CTTGCCTGGGCCAAATCTGGATTCTCTCCTGCTGCTAGAACCTTCTTGCAGCAATTCGGTATCAACATC

SEQ ID NO:4 ("S" ORF amino acid)
MSSQFIFEDVPQRNAATFNPEVGYVAFIGKYGQQLNFGVARVFFLNQKKAKMVLHKTAQPSVDLTFGGVK
FTVVNNHFPQYVSNPVPDNAITLHRMSGYLARWIADTCKASVLKLAEASAQIVMPLAEVKGCTWADGYTM
YLGFAPGAEMFLDAFDFYPLVIEMHRVLKDNMDVNFMKKVLRQRYGTMTAEEWMTQKITEIKAAFNSVGQ
LAWAKSGFSPAARTFLQQFGINI

SEQ ID NO:5 ("S" 3' UTR)
TGAACCTCTTCATCACAGATCTTCAATTTCCGTGCAATATGTCTATGTATTGCACACCATTATACTGCAA
GGCTTCTGTTAAGATAGTTAATAAGTGGAGAACACTACT

SEQ ID NO:6 (Ribozyme/T7 Terminator)
GGGTCGGCATGGCATCTCCACCTCCTCGCGGTCCGACCTGGGCATCCGAAGGAGGACGTCGTCCACTCGG
ATGGCTAAGGGAGAGCTCGGATCCGGCTGCTAACAAAGCCCGAAAGGAAGCTGAGTTGGCTGCTGCCACC
GCTGAGCAATAACTAGCATAACCCCTTGGGGCCTCTAAACGGGTCTTGAGGGGTTTTTTG

*FIG. 3*

Schmallenberg Virus M segment:

SEQ ID NO:7 (T7 minimal promotor)
TAATACGACTCACTATAG

SEQ ID NO:8 ("M" 5' UTR)
AGTAGTGAACTACCACAATCAAA

SEQ ID NO:9 ("M" ORF nucleotide; "A/G's" are "A's" in SBV-Germ and
"G's" in SBV-Neth)
ATGCTTCTCAACATTGTCTTGATATCTAACTTAGCCTGTTTAGCTTTTGCACTCCCACTTAAGGAAGGCA
CTAGAGGGTCTAGGTGCTTCCTGAATGGCGAACTGGTTAAAACTGTTAACACATCAAAGGTCGTTTCAGA
ATGCTGTGTGAAAGACGACATATCTATCATTAAATCAAATGCTGAACATTATAAATCAGGAGATCGGTTG
GCTGCTGTAATAAAATATTATCGTTTATATCAGGTGAAGGATTGGCATTCTTGCAATCCAATTTATGATG
ACCACGGTTCCTTTATGATATTAGATATAGATAATACTGGCACATTAATCCCTAAAATGCATACATGCAG
AGTTGAATGCGAAATAGCACTGAATAAAGATACTGGCGAAGTTATATTGAATTCATATCGAATTAACCAC
TACCGAATCTCGGGCACAATGCATGTATCAGGTTGGTTTAAAAACAAAATTGAGATTCCTTTGGAAAACA
CATGCGAATCCATTGAGGTAACATGTGGATTAAAAACACTTAATTTTCATGCATGTTTCCATACCCATAA
GTCATGCACCCGCTATTTTAAAGGATCAATCCTGCCGGAATTGATGATCGAATCATTTTGTACGAATCTT
GAATTAATACTGCTAGTAACTTTCATATTAGTTGGGTCTGTCATGATGATGATATTGACGAAAACATATA
TAGTATATGTGTTCATTCCTATATTTTATCCATTTGTGAAATTATATGCTTATATGTACAACAAATATTT
TAAATTGTGTAAAAATTGCCTGTTAGCAGTACATCCCTTTACAAATTGCCCATCGACATGCATCTGTGGA
ATGATTTACACTACCACTGAATCACTCAAATTGCATCGCATGTGTAACAATTGTTCTGGCTATAAAGCAT
TGCCGAAAACAAGGAAATTGTGTAAAAGTAAAATATCCAATATAGTGCTATGTGTGATAACATCACTGAT
ATTTTTCTCATTTATCACACCTATATCGAGTCAATGTATCGATATAGAAAAACTGCCAGACGAGTATATT
ACATGTAAAAGAGAGCTAGCTAATATCAAAAGCTTGACAATTGATGACACATATAGCTTTATATATTCCT
GTACATGCATAATTGTGTTAATATTACTTAAAAAGGCAGCAAAGTATATCTTGTACTGCAACTGCAGCTT
TTGTGGTATGGTACATGAACGACGTGGATTGAAGATAATGGACAACTTTACAAACAAGTGCCTAAGTTGT
GTATGCGCAGAAAACAAGGGCTTAACAATTCACAGAGCCTCTGAGAAATGTCTGTTCAAATTTGAATCAA
GTTATAATAGGACCGGGTTGATAATCTTTATGCTTCTGTTAGTCCCAACAATTGTAATGACGCAAGAAAC
TAGTATTAACTGCAAAAACATTCAATCAACTCAGCTTACAATAGAGCACCTGAGTAAGTGCATGGCATTT
TATCAAAATAAAACAAGCTCACCAGTTGTAATCAATGAAATAATTTCAGATGCTTCAGTAGACGAACAAG
AATTAATAAAAAGTTTAAACTTGAACTGTAATGTCATAGATAGGTTTATTTCCGAATCTAGTGTTATTGA
GACTCAAGTTTATTATGAGTATATAAAATCACAGTTGTGCCCTCTCCAAGTGCATGATATTTTCACTATC
AATTCAGCAAGTAACATACAATGGAAAGCACTGGCCCGAAGTTTCACCTTAGGAGTGTGCAATACGAATC
CTCATAAACATATATGTAGATGCTTGGAGTCTATGCAAATGTGCACATCAACCAAGACAGACCACGCTAG
GGAAATGTCAATATATTATGATGGTCATCCAGATCGCTTTGAGCATGACATGAAAATAATATTGAATATA
ATGAGATATATAGTCCCTGGATTAGGTCGAGTCTTGCTTGATCAAATCAAACAAACAAAAGACTACCAAG
CTTTACGCCACATACAAGGTAAGCTTTCTCCTAAATCGCAGTCAAATTTACAACTTAAAGGATTTCTGGA
ATTTGTTGATTTTATCCTTGGTGCAAACGTGACAATAGAAAAAACCCCTCAAACATTAACTACATTATCT
TTGATAAAAGGAGCCCACAGAAACTTGGATCAAAAAGATCCAGGTCCAACACCAATACTGGTATGCAAAT
CACCACAAAAGTGGTATGCTACTCACCACGTGGTGTCACACACCCAGGAGATTATATATCATGC (A/G)
AATCTAAGATGTATAAGTGGCCATCTTTAGGGGTATACAAACATAATAGAGACCAGCAACAAGCCTGCAG
CAGTGACACACATTGCCTAGAGATGTTTGAACCAGCAGAAAGAACAATAACTACAAAAATATGCAAAGTA
AGTGATATGACTTATTCAGAATCGCCATATAGTACTGGAATACCATCATGCAACGTGAAGAGATTTGGAT
CATGTAATGTAAGGGGTCATCAATGGCAAATTGCAGAATGCTCAAATGGCTTATTTTACTATGTTTCAGC
TAAAGCCCATTCGAAAACTAACGATATAACACTGTACTGTTTATCAGCAAATTGCCTGGACTTGCGTTAT
GCAT

FIG. 4

TCAGATCCAGTAGTTGTTCAGATATAGTATGGGATACAAGTTATCGAAATAAATTAACACCTAAATCTAT
TAATCATCCAGATATTGAAAACTACATAGCAGCGCTTCAGTCAGATATTGCAAATGATTTAACTATGCAC
TACTTTAAACCATTAAAAAACCTTCCAGCAATAATTCCTCAATACAAAACAATGACATTGAATGGGGACA
AGGTATCAAATGGTATTAGAAATAGTTATATCGAGTCGCACATCCCTGCAATTAATGGTTTATCAGCAGG
GATTAATATTGCCATGCCAAATGGAGAAAGCCTCTTTTCCATTATTATCTATGTCAGAAGAGTAATAAAT
AAAGCATCGTATCGATTTCTATATGAAACAGGACCCACAATTGGAATAAATGCCAAGCACGAAGAGGTAT
GTACCGGGAAGTGCCCAAGCCCAATACCACATCAAGATGGTTGGGTCACATTCTCAAAGGAAAGATCAAG
TAATTGGGGCTGTGAAGAATGGGGTTGCTTGGCAATAAATGATGGTTGTTTATATGGGTCATGTCAAGAC
ATAATAAGGCCTGAATATAAGATATACAAGAAGTCTAGTATTGAACAAAAGGATGTTGAAGTTTGTATAA
CCATGGCCCATGAATCATTCTGCAGTACCGTTGATGTTCTCCAACCTTTAATTAGCGACAGGATACAATT
AGATATCCAAACGATTCAAATGGACTCTATGCCAAATATAATTGCAGTCAAGAATGGGAAAGTTTATGTT
GGAGATATCAATGACTTAGGTTCGACAGCAAAGAAATGTGGCTCAGTCCAATTATATTCTGAAGGGATCA
TTGGATCGGGAACCCCAAAATTTGATTATGTTTGCCATGCATTCAATCGTAAAGATGTCATCCTTCGAAG
ATGCTTTGATAACTCATATCAGTCTTGTCTTCTCTTGGAACAAGATAATACATTAACTATTGCTTCTACC
AGTCATATGGAAGTGCATAAAAAAGTTTCAAGCGTGGGTACAATCAATTATAAAATTATGTTAGGGGATT
TTGACTACAATGCATATTCAACACAAGCAACAGTCACAATAGATGAGATCAGGTGTGGTGGTTGTTATGG
CTGCCCTGAAGGAATGGCTTGCGCACTCAAATTGAGTACCAATACCATCGGGAGTTGTTCAATAAAAAGT
AACTGCGATACATACATTAAAATAATAGCAGTCGATCCGATGCAGAGCGAGTATTCCATTAAGTTAAACT
GCCCACTAGCAACAGAGACAGTTTCAGTAAGTGTGTGCTCAGCTTCTGCTTACACAAAACCTTCAATATC
TAAAAATCAACCAAAAATTGTTTTGAATTCCTTAGATGAAACATCTTACATCGAGCAACATGATAAAAG
TGTTCTACATGGCTTTGCAGAGTTTAT (A/G) AAGAAGGGATTAGCGTAATATTTCAGCCTCTATTTGGC
AACCTATCTTTCTATTGGAGACTGACAATATATATAATAATCTCTTTGATTATGCTAATTCTGTTTCTAT
ACATATTAATACCACTGTGCAAACGGCTAAAAGGTTTATTGGAATACAATGAGAGAATATACCAAATGGA
AAATAAATTTAAG

SEQ ID NO:10 (SBV-Germ sequence → wherein both variable nucleotides of
SEQ ID NO:9 are "A")
MLLNIVLISNLACLAFALPLKEGTRGSRCFLNGELVKTVNTSKVVSECCVKDDISIIKSNAEHYKSGDRL
AAVIKYYRLYQVKDWHSCNPIYDDHGSFMILDIDNTGTLIPKMHTCRVECEIALNKDTGEVILNSYRINH
YRISGTMHVSGWFKNKIEIPLENTCESIEVTCGLKTLNFHACFHTHKSCTRYFKGSILPELMIESFCTNL
ELILLVTFILVGSVMMMILTKTYIVYVFIPIFYPFVKLYAYMYNKYFKLCKNCLLAVHPFTNCPSTCICG
MIYTTTESLKLHRMCNNCSGYKALPKTRKLCKSKISNIVLCVITSLIFFSFITPISSQCIDIEKLPDEYI
TCKRELANIKSLTIDDTYSFIYSCTCIIVLILLKKAAKYILYCNCSFCGMVHERRGLKIMDNFTNKCLSC
VCAENKGLTIHRASEKCLFKFESSYNRTGLIIFMLLLVPTIVMTQETSINCKNIQSTQLTIEHLSKCMAF
YQNKTSSPVVINEIISDASVDEQELIKSLNLNCNVIDRFISESSVIETQVYYEYIKSQLCPLQVHDIFTI
NSASNIQWKALARSFTLGVCNTNPHKHICRCLESMQMCTSTKTDHAREMSIYYDGHPDRFEHDMKIILNI
MRYIVPGLGRVLLDQIKQTKDYQALRHIQGKLSPKSQSNLQLKGFLEFVDFILGANVTIEKTPQTLTTLS
LIKGAHRNLDQKDPGPTPILVCKSPQKVVCYSPRGVTHPGDYISCKSKMYKWPSLGVYKHNRDQQQACSS
DTHCLEMFEPAERTITTKICKVSDMTYSESPYSTGIPSCNVKRFGSCNVRGHQWQIAECSNGLFYYVSAK
AHSKTNDITLYCLSANCLDLRYAFRSSSCSDIVWDTSYRNKLTPKSINHPDIENYIAALQSDIANDLTMH
YFKPLKNLPAIIPQYKTMTLNGDKVSNGIRNSYIESHIPAINGLSAGINIAMPNGESLFSIIIYVRRVIN
KASYRFLYETGPTIGINAKHEEVCTGKCPSPIPHQDGWVTFSKERSSNWGCEEWGCLAINDGCLYGSCQD
IIRPEYKIYKKSSIEQKDVEVCITMAHESFCSTVDVLQPLISDRIQLDIQTIQMDSMPNIIAVKNGKVYV
GDINDLGSTAKKCGSVQLYSEGIIGSGTPKFDYVCHAFNRKDVILRRCFDNSYQSCLLLEQDNTLTIAST
SHMEVHKKVSSVGTINYKIMLGDFDYNAYSTQATVTIDEIRCGGCYGCPEGMACALKLSTNTIGSCSIKS
NCDTYIKIIAVDPMQSEYSIKLNCPLATETVSVSVCSASAYTKPSISKNQPKIVLNSLDETSYIEQHDKK
CSTWLCRVYKEGISVIFQPLFGNLSFYWRLTIYIIISLIMLILFLYILIPLCKRLKGLLEYNERIYQMEN
KFK

*FIG. 4 (Continued)*

SEQ ID NO:11 (SBV-Neth sequence → wherein both variable nucleotides of SEQ ID NO:9 are "G")
MLLNIVLISNLACLAFALPLKEGTRGSRCFLNGELVKTVNTSKVVSECCVKDDISIIKSNAEHYKSGDRL
AAVIKYYRLYQVKDWHSCNPIYDDHGSFMILDIDNTGTLIPKMHTCRVECEIALNKDTGEVILNSYRINH
YRISGTMHVSGWFKNKIEIPLENTCESIEVTCGLKTLNFHACFHTHKSCTRYFKGSILPELMIESFCTNL
ELILLVTFILVGSVMMMILTKTYIVYVFIPIFYPFVKLYAYMYNKYFKLCKNCLLAVHPFTNCPSTCICG
MIYTTTESLKLHRMCNNCSGYKALPKTRKLCKSKISNIVLCVITSLIFFSFITPISSQCIDIEKLPDEYI
TCKRELANIKSLTIDDTYSFIYSCTCIIVLILLKKAAKYILYCNCSFCGMVHERRGLKIMDNFTNKCLSC
VCAENKGLTIHRASEKCLFKFESSYNRTGLIIFMLLLVPTIVMTQETSINCKNIQSTQLTIEHLSKCMAF
YQNKTSSPVVINEIISDASVDEQELIKSLNLNCNVIDRFISESSVIETQVYYEYIKSQLCPLQVHDIFTI
NSASNIQWKALARSFTLGVCNTNPHKHICRCLESMQMCTSTKTDHAREMSIYYDGHPDRFEHDMKIILNI
MRYIVPGLGRVLLDQIKQTKDYQALRHIQGKLSPKSQSNLQLKGFLEFVDFILGANVTIEKTPQTLTTLS
LIKGAHRNLDQKDPGPTPILVCKSPQKVVCYSPRGVTHPGDYISCESKMYKWPSLGVYKHNRDQQQACSS
DTHCLEMFEPAERTITTKICKVSDMTYSESPYSTGIPSCNVKRFGSCNVRGHQWQIAECSNGLFYYVSAK
AHSKTNDITLYCLSANCLDLRYAFRSSSCSDIVWDTSYRNKLTPKSINHPDIENYIAALQSDIANDLTMH
YFKPLKNLPAIIPQYKTMTLNGDKVSNGIRNSYIESHIPAINGLSAGINIAMPNGESLFSIIIYVRRVIN
KASYRFLYETGPTIGINAKHEEVCTGKCPSPIPHQDGWVTFSKERSSNWGCEEWGCLAINDGCLYGSCQD
IIRPEYKIYKKSSIEQKDVEVCITMAHESFCSTVDVLQPLISDRIQLDIQTIQMDSMPNIIAVKNGKVYV
GDINDLGSTAKKCGSVQLYSEGIIGSGTPKFDYVCHAFNRKDVILRRCFDNSYQSCLLLEQDNTLTIAST
SHMEVHKKVSSVGTINYKIMLGDFDYNAYSTQATVTIDEIRCGGCYGCPEGMACALKLSTNTIGSCSIKS
NCDTYIKIIAVDPMQSEYSIKLNCPLATETVSVSVCSASAYTKPSISKNQPKIVLNSLDETSYIEQHDKK
CSTWLCRVYEEGISVIFQPLFGNLSFYWRLTIYIIISLIMLILFLYILIPLCKRLKGLLEYNERIYQMEN
KFK

SEQ ID NO:12 (SBV-Germ "M" 3' UTR)
TGATAAGCCTTATAACAATGAGCAATTATAAATGAATAAATAAAAACAATAAAAGATAAACAAATAACAA
CATATATATGTGGTTACACATATATATGTAATTATTCAGCTGAGAAGTTTTTCATGTGGTAGAACACTAC
T

SEQ ID NO:13 (SBV-Neth "M" 3' UTR)
TGATAAGCCCTATAACAATGAGCAATTATAAATGAATAAATAAAAACAATAAAAGATAAACAAATAACAA
CATATATATGTGGTTACACATATATATGTAATTATTCAGCTGAGAAGTTTTTCATGTGGTAGAACACTAC
T

SEQ ID NO:6 (Ribozyme/T7 Terminator)
GGGTCGGCATGGCATCTCCACCTCCTCGCGGTCCGACCTGGGCATCCGAAGGAGGACGTCGTCCACTCGG
ATGGCTAAGGGAGAGCTCGGATCCGGCTGCTAACAAAGCCCGAAAGGAAGCTGAGTTGGCTGCTGCCACC
GCTGAGCAATAACTAGCATAACCCCTTGGGGCCTCTAAACGGGTCTTGAGGGGTTTTTG

*FIG. 4 (Continued)*

Schmallenberg Virus L segment:

SEQ ID NO:7 (T7 minimal promotor)
TAATACGACTCACTATAG

SEQ ID NO:13 ("L" 5'UTR)
AGTAGTGTACCCCTAATTACAATCACT

SEQ ID NO:14 ("L" ORF nucleotide)
ATGGAGACATACAAGATTAACATTTTTAGAGATAGGATCAACCAGTGTCGAAGTGCTGAAGAAGCCAAAG
ACATTGTTGCTGATCTTCTCATGGCTAGACATGACTACTTTGGTAGAGAGGTATGTTATTACCTGGATAT
CGAATTCCGGCAGGATGTTCCAGCTTACGACATACTTCTTGAATTTCTGCCAGCTGGCACTGCTTTCAAC
ATTCGCAATTGTACACCAGACAATTTTATCATTCACAATGGCAAGCTTTATATCATTGACTATAAAGTAT
CAACTGATCATGCATATGGTCAAAAAACTTATGAAAAGTACACCCAGATCTTTGGAGACGCATTGTCAGA
ATTGCCGTTTGATTTTGAAGTTGTGATCATCCGTGCTGACCCTCTGCGAGATACTATCCATGTTAATTCA
AATCAATTCTTGGAAATATTTGGGCCGCTCAACATAAACCTTGATTTACTTGGTTCTTTAATTTGCGAT
CCCTGATATATGAGAAATATAAGGATGACGACAGATTCCTAGAAATTGTGAATCAAGGTGAATTTACGAT
GACTGGACCCTGGATTGATGAGGATACCCCGGAGCTCTATTCACACCCTGTCTTTTTGGAATTCTATGAT
TCTTTAGATGAGATGGCTAAACTGACATTCCATGAGTCTATGACATTTGATGCAACTCGCGGTGAGAAAT
GGAATCAAAATCTACAAAAGGTTATAAATAGATATGGCAATGATTATAACATTTTTGTGAAAGAGGCCGC
TGCAGGAATCTTTAGATGTGAAGGGAACTACCCAAAACCAAATCATGATGAAATCACAATCGGTTGGAAT
CAAATGGTTCAAAGAGTGAGTACTGAGAGAAACCTGACTCAAGATGTCAGCAAGCAAAAACCATCTATTC
ATTTCATATGGGGTCAACCTGACGAAACATCAAATGCGACAACACCAAAACTAATCAAGATTGCAAAAGC
ACTCCAAAATATTTCTGGCGAGTCTACATATATAAGCGCATTCAGAGCATTGGGTATGCTTATGGACTTT
TCTGAGAACACAGCTTTATATGAAGCACACACTAGCAAACTAAAAAGTATGGCAAGACAGACATCGAAAA
GAATTGATACTAAACTGGAACCAATCAAAATAGGCACGGCGACAATTTATTGGGAACAGCAGTTTAAACT
GGATACTGAAATAATGAATACAAAAGACAAATCACATTTGCTAAAAGATTTTCTTGGCATAGGGGGTCAC
GTGCAATTTTCAAAAAAGACCATTGACGATTTGGATACTGACAAACCTACTATATTAGATTTCAACAAAA
AGGAAGTCATTGATTTTGCAAATTCCAGTATGAAAATGTAAAGAAAATACTATCCGGAGATAATAATCT
AGAGCGTATAGGATGTTATTTAGAAGAATATGGTGCAAATATTGCATCATGTTCAAAGGATACATGGGAT
CAGATTAACCAGATAGGGAAGTCAAATTACTGGGCTTGTATTAAAGATTTTTCAGTCTTGATGAAAAATA
TGTTGGCAGTTTCTCAATATAATAGGCACAATACTTTTCGTGTAGTGTGTTGTGCAAACAATAATCTGTT
TGGGTTTGTAATGCCTTCTTCTGATATTAAAGCAAAGCGATCCACACTTGTTTACTTCTTAGCTGTGTTG
CATTCTACTCCTCAGAATGTGATGCACCACGGTGCATTGCATGCGACATTTAAAACTGGTTCAAAATACC
TTAGTATCTCTAAAGGAATGCGTTTAGATAAAGAACGATGTCAACGCATAGTTAGTTCACCGGGACTTTT
TATGTTGACTACATTGATGTTTGCAGGAGACAATCCGACACTCAATTTGACTGATGTCATGAATTTTACA
TTCCACACTTCCCTGTCTATAACCAAAGCTATGCTGTCATTGACAGAACCATCAAGATATATGATAATGA
ATTCATTAGCCATATCCAGTCATGTTAGAGATTATATAGCAGAAAAATTTGGCCCTTATACAAAGACCAG
CTTCTCTGTAGTAATGGCAAACTTGATTAAAAGGGGATGTTATATGGCATATAATCAAAGAGATAAAGTA
GACATGAGGAATATCTGCCTAACAGATTATGAAATAACTCAAAAAGGTGTGAGAGATAACAGAGACCTAT
CATCAATCTGGTTTGAAGGCTATGTATCACTAAAAGAATATATTAACCAAATATATCTACCATTTTACTT
CAATTCAAAAGGTTTGCATGAAAAGCATCATGTTATGATAGATCTGGCTAAGACAATCTTAGATATAGAA
AGGGACCAGAGATTAAATATCCCAGGAATATGGTCTACAACACCTAGAAAACAAACTGCAAATTTAAATA
TAACTATCTATGCAGTTGCAAAAAATCTAATAATGGACACTGCTAGACATAATTATATTAGATCACGGAT
AGAAAACACAAACAACTTAAATAGATCGATATGCACTATTTCTACATTCACCAGCTCTAAATCATGTATT
AAAGTAGGCGACTTTGAGAAAGAAAAAGCTCAGCAACAAAAAGGCTGCAGATTGCATGTCAAAAGAGA
TAAAGAAGTATACAATTGCAAACCCAGAATTTGTTGATGAAGAGTTACTAAATGCAACTATAAGACATTC

*FIG. 5*

```
ACGCTATGAAGACTTAAAAAAAGCAATCCCGAATTATATTGACATTATGTCAACTAAAGTATTTGATTCT
CTGTACCAGAAAATAAAAAGGAAGGAGATAGATGATAAACCCACTGTGTATCATATACTCTCTGCTATGA
AGAATCACACAGATTTTAAGTTTACATTCTTTAACAAAGGCCAAAAAACAGCAAAGGATAGGGAAATATT
CGTAGGCGAATTTGAGGCAAAATGTGCTTGTATTTAGTGGAGAGGATATCTAAAGAACGCTGTAAGTTG
AATCCAGATGAGATGATTAGTGAACCAGGCGATTCTAAATTGAAAAAATTAGAAGAGCTTGCAGAGTCTG
AAATACGATTCACAGCAGCAACTATGAAACAGATCAAAGAACGCTATTTAGCAGAAATGGGAGAAGCAAG
CCATATGATCGCATATAAACCACATTCTGTTAAGATTGAAATCAATGCAGACATGTCAAATGGAGTGCC
CAAGATGTTTTATTCAAATATTTCTGGTTGTTTGCATTAGATCCCGCACTTTATCTGCAAGAAAAGAAA
GGATATTGTACTTCCTATGCAATTATATGCAAAAAAGCTAATTCTGCCTGATGAAATGCTCTGTAGCAT
CCTTGACCAACGTATCAAACATGAGGATGATATAATATATGAAATGACCAATGGCTTATCGCAAAATTGG
GTCAATATTAAACGGAACTGGCTGCAGGGGAATCTCAATTACACAAGTAGCTACCTACATTCATGTTCTA
TGAATGTTTATAAGGATATTCTAAAGAGAGCAGCCACTTTACTAGAAGGGGAAGTTTTAGTCAATTCTAT
GGTTCATTCTGATGACAATCACACTTCAATAGTGATGATCCAAGATAAATTAGATGATGATATTGTTATT
GAATTTTCTGCAAAACTATTTGAAAAAATATGTCTAACTTTTGGAAATCAAGCAAATATGAAGAAGACAT
ATATAACAAATTTCATAAAGGAGTTCGTTTCACTTTTTAATATTTATGGTGAGCCATTTCTGTTTATGG
TCGCTTTATTTTGACATCTGTTGGCGATTGTGCTTTCTTGGACCATATGAGGATGTTGCCAGTAGGTTG
TCTGCAACGCAGACAGCAATTAAGCATGGAGCACCTCCATCACTTGCATGGACTGCTATTGCATTAACTC
AGTGATAACACATAGCACATATAACATGCTTCCAGGTCAAATCAATGATCCTACTTCATCTTTACCTAG
TCATGATAGATTTGAGCTGCCTATAGAATTGTGTGGCTTAATAAATTCAGAATTACCCACTATAGCTATA
GCAGGTTTGGAAGCAGATAATCTAAGTTATTTAGTTAGGTTATCAAAAAGAATGTCCCCTATACATCTTT
GCCGTGAACCAATCCAGCATCAATATGAGAATATACATACATGGGATATAAGTAAACTGACACAATGTGA
TATTTTCAGACTTAAGCTTTTAAGATACATGACGTTAGACTCAACTATGTCATCTGATGATGGAATGGGC
GAAACTAGTGAAATGAGATCTAGGTCTCTTCTGACACCAAGAAAATTCACTACTGCAAGTTCGTTATCTA
GATTGCATTCATATGCTGATTATCAAAAAACAATACAAGACCAACAGAAAATTGAAGAATTATTTGAATA
TTTTATAGCCAACCCTCAACTATTGGTTACAAAAGGTGAGACTTGTGAAGAGTTCTGTATGTCTGTATTG
TTCAGATACAACAGTCGTAAATTTAAAGAATCATTGTCTATTCAAAACCCAGCTCAGCTCTTCATAGAAC
AAGTATTGTTTGCAAATAAACCAATGATAGACTATACAAGTATTCATGATAGGTTGTTTGGTATACAAGA
TGACCCAAATATAAATGATGCTACATGTATTATTGGCAAGAAGACTTTTGTTGAAACATATCAGCAAATA
AAAATTGATGTAGAAAAATTTACACTTGATGTAGAGGATATAAAGACGATATATAGCTTCTGTATAATGA
ACGACCCTATATTAGTTGCTTGTGCAAACAACTTGTTAATTTCAATACAGGGAGTGGAGATGCAACGATT
GGGTATGACATGCTGTTATATGCCGGAGATTAAGAGCCTTAAAGTAATTTATCATAGTCCTGCTCTCGTA
TTACGTGCTTATGTAACAGATAACTATGAGCAAAAAGGGATGGAGCCAGATGAAATGCGGAGAGATATAT
ATCATTTAGAAGAATTTATAGAGAAGACAAAATTGAGGACAAATATGCAAGGGAGAATTGCAAATAATGA
AATTAAGTTAATGAAGCGAGATTTGAAATTTGAAGTGCAGGAATTGACTAAATTCTATCAGATCTGTTAT
GAATATGTGAAATCAACAGAACACAAAATTAAATATTCATCCTTCCAAAAAAGGCTTACACTCCCATTG
ATTTCTGCTCATTAGTAACAGGTAATCTGATATCAGACAACAAATGGATGGTTGTTCACTATTTAAAACA
AATAACTGTCCCAGCAAAGAAGGCACAAATAGCCACATCTATAGATCTGGAAATACAAATAGCCTACGAA
TGTTTCAGGCTAATTGCACATTTTGCTGATATGTTCCTAAATGATGACTCCAAAAAAGCTTATATTAATG
CAATTATTAACACATATACATACAAGGATGTTCAAGTATCCAGTCTCTACAAGAAAATCAAAAATTCGAG
ACTACGTTCAAAAATTATACCATTATTATATCACCTGGGCGATTTGCAACAAATAGACGTTGACAGATTT
GATGCAGAAAAAGCAGAAGAGCAGATCACATGGAATAACTGGCAAACATCTCGAGAATTTACTACTGGTC
CAATTGATCTATCAATCAAAGGTTATGGACGGTCAATAAGGATCGTAGGTGAGGACAACAAGCTTACAGC
TGCAGAAATGCAATTGTCAAGAGTGAGAAGTGATATAGTATCAAGGCATGGACAGGCTTTATTGAACAAA
CCTCATGGGCTAAAATTAGAGAAAATGGAACCAGTGACTGATCTAAATCCTAAATTATGGTATATTGCAT
ACCAATTGCGTGAGAAAAGCGGTATCACTATGGGGTCTTTAGTACATCTTATATAGAAGAGCATAACTC
AAGGATAGAAGCATCTCGGATACGTAAGACTAATAAATGGATACCAGTTTGCCCTATTGCTATATCAAAA
```

FIG. 5 (Continued)

```
CAATCATCTGATGGAAAGCCTAGTCTTGCAAAAATCCCTATGTTAAATATTGGGGAGATTAAATTTACAA
AACTACAGATTGCAGTAGATGATCATGCAATGATTAGGAAAGCCCCATTTAGTAAGATGGTGTTCTTTGA
TGGCCCACCCATACAGAGCGGTGGCATTGACATTGGAAAGCTTATGAAGAACCAAAATATTCTCAATTTG
AGGTTAGATAATATACAGAGTATAACATTATTAGATTTGTGCCGCATATTTTCATGCCGAGGGTCTAAAG
TGGATCAAGATGCATTTGAATTCTTATCTGATGAACCTTTGGATGAAGATGTTATTGATGAATTAGATAG
CTCACCTGCATTAGTGGTATCTTACACAAAGAAATCAACCAAATCCAATAGTTTCAAAAATGTTATAGTT
AGAGCATTGATAAGAGAATGTGATATATTTGAAGATATAATGGACATAACAGACGATGGATTCACATCTG
ATAGCAATCTAGAGGTGTTAGAAAACTTAACATGGATTTTAAATATGCTCGCAACAAATCAGTGGTCTAC
AGAACTGTTAGCATGCATACACATGTGTTTATATCGCAATGAGATGGATCATATCTATCACAATTTTCAA
GTTCCAGAAATATTTGTCGACAATCCAATCTCATTAAATGTAAAGTGGGATGAAGTAATTATGTTCTTAA
ACATACTGCGAGACAGAGATTACAAATTTGAGCCATGGGTGTCTATACTGAATCATTCCTTAACTAAAGC
TATAGAGTATGCTTACAAAAAGATGGAAGAGGAGAGGAAGCAGAAATCAACAGGCATCAACAAATTCTTA
AAGGGTAAAAAAATGGGTGGCAGATCAAAGTTTGATTTCCAG
```

SEQ ID NO:15 ("L" ORF amino acid)
```
METYKINIFRDRINQCRSAEEEAKDIVADLLMARHDYFGREVCYYLDIEFRQDVPAYDILLEFLPAGTAFN
IRNCTPDNFIIHNGKLYIIDYKVSTDHAYGQKTYEKYTQIFGDALSELPFDFEVVIIRADPLRDTIHVNS
NQFLEIFGPLNINLDFTWFFNLRSLIYEKYKDDDRFLEIVNQGEFTMTGPWIDEDTPELYSHPVFLEFYD
SLDEMAKLTFHESMTFDATRGEKWNQNLQKVINRYGNDYNIFVKEAAAGIFRCEGNYPKPNHDEITIGWN
QMVQRVSTERNLTQDVSKQKPSIHFIWGQPDETSNATTPKLIKIAKALQNISGESTYISAFRALGMLMDF
SENTALYEAHTSKLKSMARQTSKRIDTKLEPIKIGTATIYWEQQFKLDTEIMNTKDKSHLLKDFLGIGGH
VQFSKKTIDDLDTDKPTILDFNKKEVIDFCKFQYENVKKILSGDNNLERIGCYLEEYGANIASCSKDTWD
QINQIGKSNYWACIKDFSVLMKNMLAVSQYNRHNTFRVVCCANNNLFGFVMPSSDIKAKRSTLVYFLAVL
HSTPQNVMHHGALHATFKTGSKYLSISKGMRLDKERCQRIVSSPGLFMLTTLMFAGDNPTLNLTDVMNFT
FHTSLSITKAMLSLTEPSRYMIMNSLAISSHVRDYIAEKFGPYTKTSFSVVMANLIKRGCYMAYNQRDKV
DMRNICLTDYEITQKGVRDNRDLSSIWFEGYVSLKEYINQIYLPFYFNSKGLHEKHHVMIDLAKTILDIE
RDQRLNIPGIWSTTPRKQTANLNITIYAVAKNLIMDTARHNYIRSRIENTNNLNRSICTISTFTSSKSCI
KVGDFEKEKSSATKKAADCMSKEIKKYTIANPEFVDEELLNATIRHSRYEDLKKAIPNYIDIMSTKVFDS
LYQKIKRKEIDDKPTVYHILSAMKNHTDFKFTFFNKGQKTAKDREIFVGEFEAKMCLYLVERISKERCKL
NPDEMISEPGDSKLKKLEELAESEIRFTAATMKQIKERYLAEMGEASHMIAYKPHSVKIEINADMSKWSA
QDVLFKYFWLFALDPALYLQEKERILYFLCNYMQKKLILPDEMLCSILDQRIKHEDDIIYEMTNGLSQNW
VNIKRNWLQGNLNYTSSYLHSCSMNVYKDILKRAATLLEGEVLVNSMVHSDDNHTSIVMIQDKLDDDIVI
EFSAKLFEKICLTFGNQANMKKTYITNFIKEFVSLFNIYGEPFSVYGRFILTSVGDCAFLGPYEDVASRL
SATQTAIKHGAPPSLAWTAIALTQWITHSTYNMLPGQINDPTSSLPSHDRFELPIELCGLINSELPTIAI
AGLEADNLSYLVRLSKRMSPIHLCREPIQHQYENIHTWDISKLTQCDIFRLKLLRYMTLDSTMSSDDGMG
ETSEMRSRSLLTPRKFTTASSLSRLHSYADYQKTIQDQQKIEELFEYFIANPQLLVTKGETCEEFCMSVL
FRYNSRKFKESLSIQNPAQLFIEQVLFANKPMIDYTSIHDRLFGIQDDPNINDATCIIGKKTFVETYQQI
KIDVEKFTLDVEDIKTIYSFCIMNDPILVACANNLLISIQGVEMQRLGMTCCYMPEIKSLKVIYHSPALV
LRAYVTDNYEQKGMEPDEMRRDIYHLEEFIEKTKLRTNMQGRIANNEIKLMKRDLKFEVQELTKFYQICY
EYVKSTEHKIKIFILPKKAYTPIDFCSLVTGNLISDNKWMVVHYLKQITVPAKKAQIATSIDLEIQIAYE
CFRLIAHFADMFLNDDSKKAYINAIINTYTYKDVQVSSLYKKIKNSRLRSKIIPLLYHLGDLQQIDVDRF
DAEKAEEQITWNNWQTSREFTTGPIDLSIKGYGRSIRIVGEDNKLTAAEMQLSRVRSDIVSRHGQALLNK
PHGLKLEKMEPVTDLNPKLWYIAYQLREKKRYHGVFSTSYIEEHNSRIEASRIRKTNKWIPVCPIAISK
QSSDGKPSLAKIPMLNIGEIKFTKLQIAVDDHAMIRKAPFSKMVFFDGPPIQSGGIDIGKLMKNQNILNL
RLDNIQSITLLDLCRIFSCRGSKVDQDAFEFLSDEPLDEDVIDELDSSPALVVSYTKKSTKSNSFKNVIV
RALIRECDIFEDIMDITDDGFTSDSNLEVLENLTWILNMLATNQWSTELLACIHMCLYRNEMDHIYHNFQ
VPEIFVDNPISLNVKWDEVIMFLNILRDRDYKFEPWVSILNHSLTKAIEYAYKKMEEERKQKSTGINKFL
KGKKMGGRSKFDFQ
```

*FIG. 5 (Continued)*

SEQ ID NO:16 ("L" 3'UTR)
TAGCTTGATCTTAAATAATACATAATCTTTGCCCCAAATCTGTATTATATAAATAATTCTAAAGTAGTTT
CATGTAATTAGGGGCACACTACT

SEQ ID NO:6 (Ribozyme/T7 Terminator)
GGGTCGGCATGGCATCTCCACCTCCTCGCGGTCCGACCTGGGCATCCGAAGGAGGACGTCGTCCACTCGG
ATGGCTAAGGGAGAGCTCGGATCCGGCTGCTAACAAAGCCCGAAAGGAAGCTGAGTTGGCTGCTGCCACC
GCTGAGCAATAACTAGCATAACCCCTTGGGGCCTCTAAACGGGTCTTGAGGGGTTTTTG

*FIG. 5 (Continued)*

SEQ ID NO:17 (HE649912 nucleotide)
CTAATTACAATCACTATGGAGACATACAAGATTAACATTTTTAGAGATAGGATCAACCAGTGTCGAAGTGCTGA
AGAAGCCAAAGACATTGTTGCTGATCTTCTCATGGCTAGACATGACTACTTTGGTAGAGAGGTATGTTATTACC
TGGATATCGAATTCCGGCAGGATGTTCCAGCTTACGACATACTTCTTGAATTTCTGCCAGCTGGCACTGCTTTC
AACATTCGCAATTGTACACCAGACAATTTTATCATTCACAATGGCAAGCTTTATATCATTGACTATAAAGTATC
AACTGATCATGCATATGGTCAAAAAACTTATGAAAAGTACACCCAGATCTTTGGAGACGCATTGTCAGAATTGC
CGTTTGATTTTGAAGTTGTGATCATCCGTGCTGACCCTCTGCGAGATACTATCCATGTTAATTCAAATCAATTC
TTGGAAATATTTGGGCCGCTCAACATAAACCTTGATTTTACTTGGTTCTTTAATTTGCGATCCCTGATATATGA
GAAATATAAGGATGACGACAGATTCCTAGAAATTGTGAATCAAGGTGAATTTACGATGACTGGACCCTGGATTG
ATGAGGATACCCCGGAGCTCTATTCACACCCTGTCTTTTTGGAATTCTATGATTCTTTAGATGAGATGGCTAAA
CTGACATTCCATGAGTCTATGACATTTGATGCAACTCGCGGTGAGAAATGGAATCAAAATCTACAAAAGGTTAT
AAATAGATATGGCAATGATTATAACATTTTTGTGAAAGAGGCCGCTGCAGGAATCTTTAGATGTGAAGGGAACT
ACCCAAAACCAAATCATGATGAAATCACAATCGGTTGGAATCAAATGGTTCAAAGAGTGAGTACTGAGAGAAAC
CTGACTCAAGATGTCAGCAAGCAAAAACCATCTATTCATTTCATATGGGGTCAACCTGACGAAACATCAAATGC
GACAACACCAAAACTAATCAAGATTGCAAAAGCACTCCAAAATATTTCTGGCGAGTCTACATATATAAGCGCAT
TCAGAGCATTGGGTATGCTTATGGACTTTTCTGAGAACACAGCTTTATATGAAGCACACACTAGCAAACTAAAA
AGTATGGCAAGACAGACATCGAAAAGAATTGATACTAAACTGGAACCAATCAAAATAGGCACGGCGACAATTTA
TTGGGAACAGCAGTTTAAACTGGATACTGAAATAATGAATACAAAAGACAAATCACATTTGCTAAAAGATTTTC
TTGGCATAGGGGGTCACGTGCAATTTTCAAAAAAGACCATTGACGATTTGGATACTGACAAACCTACTATATTA
GATTTCAACAAAAAGGAAGTCATTGATTTTTGCAAATTCCAGTATGAAAATGTAAAGAAAATACTATCCGGAGA
TAATAATCTAGAGCGTATAGGATGTTATTTAGAAGAATATGGTGCAAATATTGCATCATGTTCAAAGGATACAT
GGGATCAGATTAACCAGATAGGGAAGTCAAATTACTGGGCTTGTATTAAAGATTTTTCAGTCTTGATGAAAAAT
ATGTTGGCAGTTTCTCAATATAATAGGCACAATACTTTTCGTGTAGTGTGTTGTGCAAACAATAATCTGTTTGG
GTTTGTAATGCCTTCTTCTGATATTAAAGCAAAGCGATCCACACTTGTTTACTTCTTAGCTGTGTTGCATTCTA
CTCCTCAGAATGTGATGCACCACGGTGCATTGCATGCGACATTTAAAACTGGTTCAAAATACCTTAGTATCTCT
AAAGGAATGCGTTTAGATAAAGAACGATGTCAACGCATAGTTAGTTCACCGGGACTTTTTATGTTGACTACATT
GATGTTTGCAGGAGACAATCCGACACTCAATTTGACTGATGTCATGAATTTTACATTCCACACTTCCCTGTCTA
TAACCAAAGCTATGCTGTCATTGACAGAACCATCAAGATATATGATAATGAATTCATTAGCCATATCCAGTCAT
GTTAGAGATTATATAGCAGAAAAATTTGGCCCTTATACAAAGACCAGCTTCTCTGTAGTAATGGCAAACTTGAT
TAAAAGGGGATGTTATATGGCATATAATCAAAGAGATAAAGTAGACATGAGGAATATCTGCCTAACAGATTATG
AAATAACTCAAAAAGGTGTGAGAGATAACAGAGACCTATCATCAATCTGGTTTGAAGGCTATGTATCACTAAAA
GAATATATTAACCAAATATATCTACCATTTTACTTCAATTCAAAAGGTTTGCATGAAAAGCATCATGTTATGAT
AGATCTGGCTAAGACAATCTTAGATATAGAAAGGGACCAGAGATTAAATATCCCAGGAATATGGTCTACAACAC
CTAGAAAACAAACTGCAAATTTAAATATAACTATCTATGCAGTTGCAAAAAATCTAATAATGGACACTGCTAGA
CATAATTATATTAGATCACGGATAGAAAACACAAACAACTTAAATAGATCGATATGCACTATTTCTACATTCAC
CAGCTCTAAATCATGTATTAAAGTAGGCGACTTTGAGAAAGAAAAAAGCTCAGCAACAAAAAAGGCTGCAGATT
GCATGTCAAAAGAGATAAAGAAGTATACAATTGCAAACCCAGAATTTGTTGATGAAGAGTTACTAAATGCAACT
ATAAGACATTCACGCTATGAAGACTTAAAAAAAGCAATCCCGAATTATATTGACATTATGTCAACTAAAGTATT
TGATTCTCTGTACCAGAAAATAAAAAGGAAGGAGATAGATGATAAACCCACTGTGTATCATATACTCTCTGCTA
TGAAGAATCACACAGATTTTAAGTTTACATTCTTTAACAAAGGCCAAAAAACAGCAAAGGATAGGGAAATATTC
GTAGGCGAATTTGAGGCAAAAATGTGCTTGTATTTAGTGGAGAGGATATCTAAAGAACGCTGTAAGTTGAATCC
AGATGAGATGATTAGTGAACCAGGCGATTCTAAATTGAAAAAATTAGAAGAGCTTGCAGAGTCTGAAATACGAT
TCACAGCAGCAACTATGAAACAGATCAAAGAACGCTATTTAGCAGAAATGGGAGAAGCAAGCCATATGATCGCA
TATAAACCACATTCTGTTAAGATTGAAATCAATGCAGACATGTCAAAATGGAGTGCCCAAGATGTTTTATTCAA
ATATTTCTGGTTGTTTGCATTAGATCCCGCACTTTATCTGCAAGAAAAGAAAGGATATTGTACTTCCTATGCA
ATTATATGCAAAAAAGCTAATTCTGCCTGATGAAATGCTCTGTAGCATCCTTGACCAACGTATCAAACATGAG
GATGATATAATATATGAAATGACCAATGGCTTATCGCAAAATTGGGTCAATATTAAACGGAACTGGCTGCAGGG
GAATCTCAATTACACAAGTAGCTACCTACATTCATGTTCTATGAATGTTTATAAGGATATTCTAAAGAGAGCAG
CCACTTTACTAGAAGGGGAAGTTTTAGTCAATTCTATGGTTCATTCTGATGACAATCACACTTCAATAGTGATG
ATCCAAGATAAATTAGATGATGATATTGTTATTGAATTTTCTGCAAAACTATTTGAAAAAATATGTCTAACTTT

FIG. 6

```
TGGAAATCAAGCAAATATGAAGAAGACATATATAACAAATTTCATAAAGGAGTTCGTTTCACTTTTTAATATTT
ATGGTGAGCCATTTTCTGTTTATGGTCGCTTTATTTTGACATCTGTTGGCGATTGTGCTTTTCTTGGACCATAT
GAGGATGTTGCCAGTAGGTTGTCTGCAACGCAGACAGCAATTAAGCATGGAGCACCTCCATCACTTGCATGGAC
TGCTATTGCATTAACTCAGTGGATAACACATAGCACATATAACATGCTTCCAGGTCAAATCAATGATCCTACTT
CATCTTTACCTAGTCATGATAGATTTGAGCTGCCTATAGAATTGTGTGGCTTAATAAATTCAGAATTACCCACT
ATAGCTATAGCAGGTTTGGAAGCAGATAATCTAAGTTATTTAGTTAGGTTATCAAAAGAATGTCCCCTATACA
TCTTTGCCGTGAACCAATCCAGCATCAATATGAGAATATACATACATGGGATATAAGTAAACTGACACAATGTG
ATATTTTCAGACTTAAGCTTTTAAGATACATGACGTTAGACTCAACTATGTCATCTGATGATGGAATGGGCGAA
ACTAGTGAAATGAGATCTAGGTCTCTTCTGACACCAAGAAAATTCACTACTGCAAGTTCGTTATCTAGATTGCA
TTCATATGCTGATTATCAAAAAACAATACAAGACCAACAGAAAATTGAAGAATTATTTGAATATTTTATAGCCA
ACCCTCAACTATTGGTTACAAAAGGTGAGACTTGTGAAGAGTTCTGTATGTCTGTATTGTTCAGATACAACAGT
CGTAAATTTAAAGAATCATTGTCTATTCAAAACCCAGCTCAGCTCTTCATAGAACAAGTATTGTTTGCAAATAA
ACCAATGATAGACTATACAAGTATTCATGATAGGTTGTTTGGTATACAAGATGACCCAAATATAAATGATGCTA
CATGTATTATTGGCAAGAAGACTTTTGTTGAAACATATCAGCAAATAAAAATTGATGTAGAAAAATTTACACTT
GATGTAGAGGATATAAAGACGATATATAGCTTCTGTATAATGAACGACCCTATATTAGTTGCTTGTGCAAACAA
CTTGTTAATTTCAATACAGGGAGTGGAGATGCAACGATTGGGTATGACATGCTGTTATATGCCGGAGATTAAGA
GCCTTAAAGTAATTTATCATAGTCCTGCTCTCGTATTACGTGCTTATGTAACAGATAACTATGAGCAAAAGGG
ATGGAGCCAGATGAAATGCGGAGAGATATATATCATTTAGAAGAATTTATAGAGAAGACAAAATTGAGGACAAA
TATGCAAGGGAGAATTGCAAATAATGAAATTAAGTTAATGAAGCGAGATTTGAAATTTGAAGTGCAGGAATTGA
CTAAATTCTATCAGATCTGTTATGAATATGTGAAATCAACAGAACACAAAATTAAAATATTCATCCTTCCAAAA
AAGGCTTACACTCCCATTGATTTCTGCTCATTAGTAACAGGTAATCTGATATCAGACAACAAATGGATGGTTGT
TCACTATTTAAAACAAATAACTGTCCCAGCAAAGAAGGCACAAATAGCCACATCTATAGATCTGGAAATACAAA
TAGCCTACGAATGTTTCAGGCTAATTGCACATTTTGCTGATATGTTCCTAAATGATGACTCCAAAAAAGCTTAT
ATTAATGCAATTATTAACACATATACATACAAGGATGTTCAAGTATCCAGTCTCTACAAGAAAATCAAAAATTC
GAGACTACGTTCAAAAATTATACCATTATTATATCACCTGGGCGATTTGCAACAAATAGACGTTGACAGATTTG
ATGCAGAAAAAGCAGAAGAGCAGATCACATGGAATAACTGGCAAACATCTCGAGAATTTACTACTGGTCCAATT
GATCTATCAATCAAAGGTTATGGACGGTCAATAAGGATCGTAGGTGAGGACAACAAGCTTACAGCTGCAGAAAT
GCAATTGTCAAGAGTGAGAAGTGATATAGTATCAAGGCATGGACAGGCTTTATTGAACAAACCTCATGGGCTAA
AATTAGAGAAAATGGAACCAGTGACTGATCTAAATCCTAAATTATGGTATATTGCATACCAATTGCGTGAGAAA
AAGCGGTATCACTATGGGGTCTTTAGTACATCTTATATAGAAGAGCATAACTCAAGGATAGAAGCATCTCGGAT
ACGTAAGACTAATAAATGGATACCAGTTTGCCCTATTGCTATATCAAAACAATCATCTGATGGAAAGCCTAGTC
TTGCAAAAATCCCTATGTTAAATATTGGGGAGATTAAATTTACAAAACTACAGATTGCAGTAGATGATCATGCA
ATGATTAGGAAAGCCCCATTTAGTAAGATGGTGTTCTTTGATGGCCCACCCATACAGAGCGGTGGCATTGACAT
TGGAAAGCTTATGAAGAACCAAAATATTCTCAATTTGAGGTTAGATAATATACAGAGTATAACATTATTAGATT
TGTGCCGCATATTTTCATGCCGAGGGTCTAAAGTGGATCAAGATGCATTTGAATTCTTATCTGATGAACCTTTG
GATGAAGATGTTATTGATGAATTAGATAGCTCACCTGCATTAGTGGTATCTTACACAAAGAAATCAACCAAATC
CAATAGTTTCAAAAATGTTATAGTTAGAGCATTGATAAGAGAATGTGATATATTTGAAGATATAATGGACATAA
CAGACGATGGATTCACATCTGATAGCAATCTAGAGGTGTTAGAAAACTTAACATGGATTTTAAATATGCTCGCA
ACAAATCAGTGGTCTACAGAACTGTTAGCATGCATACACATGTGTTTATATCGCAATGAGATGGATCATATCTA
TCACAATTTTCAAGTTCCAGAAATATTTGTCGACAATCCAATCTCATTAAATGTAAAGTGGGATGAAGTAATTA
TGTTCTTAAACATACTGCGAGACAGAGATTACAAATTTGAGCCATGGGTGTCTATACTGAATCATTCCTTAACT
AAAGCTATAGAGTATGCTTACAAAAAGATGGAAGAGGAGAGGAAGCAGAAATCAACAGGCATCAACAAATTCTT
AAAGGGTAAAAAAATGGGTGGCAGATCAAAGTTTGATTTCCAGTAGCTTGATCTTAAATAATACATAATCTTTG
CCCCAAATCTGTATTATATAAATAATTCTAAAGTAGTTTCATGTAATTAGGGGCAC
```

*FIG. 6 (Continued)*

SEQ ID NO:18 (HE649912 amino acid)
```
METYKINIFRDRINQCRSAEEAKDIVADLLMARHDYFGREVCYYLDIEFRQDVPAYDILLEFLPAGTAFNIRNC
TPDNFIIHNGKLYIIDYKVSTDHAYGQKTYEKYTQIFGDALSELPFDFEVVIIRADPLRDTIHVNSNQFLEIFG
PLNINLDFTWFFNLRSLIYEKYKDDDRFLEIVNQGEFTMTGPWIDEDTPELYSHPVFLEFYDSLDEMAKLTFHE
SMTFDATRGEKWNQNLQKVINRYGNDYNIFVKEAAAGIFRCEGNYPKPNHDEITIGWNQMVQRVSTERNLTQDV
SKQKPSIHFIWGQPDETSNATTPKLIKIAKALQNISGESTYISAFRALGMLMDFSENTALYEAHTSKLKSMARQ
TSKRIDTKLEPIKIGTATIYWEQQFKLDTEIMNTKDKSHLLKDFLGIGGHVQFSKKTIDDLDTDKPTILDFNKK
EVIDFCKFQYENVKKILSGDNNLERIGCYLEEYGANIASCSKDTWDQINQIGKSNYWACIKDFSVLMKNMLAVS
QYNRHNTFRVVCCANNNLFGFVMPSSDIKAKRSTLVYFLAVLHSTPQNVMHHGALHATFKTGSKYLSISKGMRL
DKERCQRIVSSPGLFMLTTLMFAGDNPTLNLTDVMNFTFHTSLSITKAMLSLTEPSRYMIMNSLAISSHVRDYI
AEKFGPYTKTSFSVVMANLIKRGCYMAYNQRDKVDMRNICLTDYEITQKGVRDNRDLSSIWFEGYVSLKEYINQ
IYLPFYFNSKGLHEKHHVMIDLAKTILDIERDQRLNIPGIWSTTPRKQTANLNITIYAVAKNLIMDTARHNYIR
SRIENTNNLNRSICTISTFTSSKSCIKVGDFEKEKSSATKKAADCMSKEIKKYTIANPEFVDEELLNATIRHSR
YEDLKKAIPNYIDIMSTKVFDSLYQKIKRKEIDDKPTVYHILSAMKNHTDFKFTFFNKGQKTAKDREIFVGEFE
AKMCLYLVERISKERCKLNPDEMISEPGDSKLKKLEELAESEIRFTAATMKQIKERYLAEMGEASHMIAYKPHS
VKIEINADMSKWSAQDVLFKYFWLFALDPALYLQEKERILYFLCNYMQKKLILPDEMLCSILDQRIKHEDDIIY
EMTNGLSQNWVNIKRNWLQGNLNYTSSYLHSCSMNVYKDILKRAATLLEGEVLVNSMVHSDDNHTSIVMIQDKL
DDDIVIEFSAKLFEKICLTFGNQANMKKTYITNFIKEFVSLFNIYGEPFSVYGRFILTSVGDCAFLGPYEDVAS
RLSATQTAIKHGAPPSLAWTAIALTQWITHSTYNMLPGQINDPTSSLPSHDRFELPIELCGLINSELPTIAIAG
LEADNLSYLVRLSKRMSPIHLCREPIQHQYENIHTWDISKLTQCDIFRLKLLRYMTLDSTMSSDDGMGETSEMR
SRSLLTPRKFTTASSLSRLHSYADYQKTIQDQQKIEELFEYFIANPQLLVTKGETCEEFCMSVLFRYNSRKFKE
SLSIQNPAQLFIEQVLFANKPMIDYTSIHDRLFGIQDDPNINDATCIIGKKTFVETYQQIKIDVEKFTLDVEDI
KTIYSFCIMNDPILVACANNLLISIQGVEMQRLGMTCCYMPEIKSLKVIYHSPALVLRAYVTDNYEQKGMEPDE
MRRDIYHLEEFIEKTKLRTNMQGRIANNEIKLMKRDLKFEVQELTKFYQICYEYVKSTEHKIKIFILPKKAYTP
IDFCSLVTGNLISDNKWMVVHYLKQITVPAKKAQIATSIDLEIQIAYECFRLIAHFADMFLNDDSKKAYINAII
NTYTYKDVQVSSLYKKIKNSRLRSKIIPLLYHLGDLQQIDVDRFDAEKAEEQITWNNWQTSREFTTGPIDLSIK
GYGRSIRIVGEDNKLTAAEMQLSRVRSDIVSRHGQALLNKPHGLKLEKMEPVTDLNPKLWYIAYQLREKKRYHY
GVFSTSYIEEHNSRIEASRIRKTNKWIPVCPIAISKQSSDGKPSLAKIPMLNIGEIKFTKLQIAVDDHAMIRKA
PFSKMVFFDGPPIQSGGIDIGKLMKNQNILNLRLDNIQSITLLDLCRIFSCRGSKVDQDAFEFLSDEPLDEDVI
DELDSSPALVVSYTKKSTKSNSFKNVIVRALIRECDIFEDIMDITDDGFTSDSNLEVLENLTWILNMLATNQWS
TELLACIHMCLYRNEMDHIYHNFQVPEIFVDNPISLNVKWDEVIMFLNILRDRDYKFEPWVSILNHSLTKAIEY
AYKKMEEERKQKSTGINKFLKGKKMGGRSKFDFQ
```

*FIG. 7*

SEQUENCE LISTING

<160> NUMBER OF SEQ ID NOS: 18

<210> SEQ ID NO 1
<211> LENGTH: 18
<212> TYPE: DNA
<213> ORGANISM: Artificial Sequence
<220> FEATURE:
<223> OTHER INFORMATION: T7 Minimal promoter

<400> SEQUENCE: 1
taatacgact cactatag                                           18

<210> SEQ ID NO 2
<211> LENGTH: 31
<212> TYPE: DNA
<213> ORGANISM: Artificial Sequence
<220> FEATURE:
<223> OTHER INFORMATION: Schmallenberg "S" 5' UTR

<400> SEQUENCE: 2
agtagtgaac tccactatta actacagaaa t                             31

<210> SEQ ID NO 3
<211> LENGTH: 699
<212> TYPE: DNA
<213> ORGANISM: Artificial Sequence
<220> FEATURE:
<223> OTHER INFORMATION: Schmallenberg "S" ORF nucleotide

<400> SEQUENCE: 3
atgtcaagcc aattcatttt tgaagatgta ccacaacgga atgcagctac atttaacccg    60
gaggtcgggt atgtggcatt tattggtaag tatgggcaac aactcaactt cggtgttgct   120
agagtcttct tcctcaacca gaagaaggcc aagatggtcc tacataagac ggcacaacca   180
agtgtcgatc ttacttttgg tggggtcaaa tttacagtgg ttaataacca tttcccaa    240 tatgtctcaa atcctgtgcc agacaatgcc attacacttc acaggatgtc aggatatcta   300
gcacgttgga ttgctgatac atgcaaggct agtgtcctca aactagctga agctagtgct   360
cagattgtca tgcccttgc tgaggttaag ggatgcacct gggccgatgg ttatacaatg   420
tatcttggat ttgcacctgg ggccgaaatg ttccttgatg cttttgactt ctatccacta   480
gttattgaaa tgcatagggt cctcaaggac aatatggatg taaattttat gaaaaaagtc   540
ctccgccaac gctatggaac aatgactgct gaagaatgga tgactcagaa aataacagaa   600
ataaaagctg cttttaattc tgttggacag cttgcctggg ccaaatctgg attctctcct   660
gctgctagaa ccttcttgca gcaattcggt atcaacatc                          699

<210> SEQ ID NO 4
<211> LENGTH: 233

-continued

<212> TYPE: PRT
<213> ORGANISM: Artificial Sequence
<220> FEATURE:
<223> OTHER INFORMATION: Schmallenberg "S" ORF Amino Acid

<400> SEQUENCE: 4

```
Met Ser Ser Gln Phe Ile Phe Glu Asp Val Pro Gln Arg Asn Ala Ala
1               5                   10                  15

Thr Phe Asn Pro Glu Val Gly Tyr Val Ala Phe Ile Gly Lys Tyr Gly
            20                  25                  30

Gln Gln Leu Asn Phe Gly Val Ala Arg Val Phe Phe Leu Asn Gln Lys
        35                  40                  45

Lys Ala Lys Met Val Leu His Lys Thr Ala Gln Pro Ser Val Asp Leu
    50                  55                  60

Thr Phe Gly Gly Val Lys Phe Thr Val Val Asn Asn His Phe Pro Gln
65                  70                  75                  80

Tyr Val Ser Asn Pro Val Pro Asp Asn Ala Ile Thr Leu His Arg Met
                85                  90                  95

Ser Gly Tyr Leu Ala Arg Trp Ile Ala Asp Thr Cys Lys Ala Ser Val
            100                 105                 110

Leu Lys Leu Ala Glu Ala Ser Ala Gln Ile Val Met Pro Leu Ala Glu
        115                 120                 125

Val Lys Gly Cys Thr Trp Ala Asp Gly Tyr Thr Met Tyr Leu Gly Phe
    130                 135                 140

Ala Pro Gly Ala Glu Met Phe Leu Asp Ala Phe Asp Phe Tyr Pro Leu
145                 150                 155                 160

Val Ile Glu Met His Arg Val Leu Lys Asp Asn Met Asp Val Asn Phe
                165                 170                 175

Met Lys Lys Val Leu Arg Gln Arg Tyr Gly Thr Met Thr Ala Glu Glu
            180                 185                 190

Trp Met Thr Gln Lys Ile Thr Glu Ile Lys Ala Ala Phe Asn Ser Val
        195                 200                 205

Gly Gln Leu Ala Trp Ala Lys Ser Gly Phe Ser Pro Ala Ala Arg Thr
    210                 215                 220

Phe Leu Gln Gln Phe Gly Ile Asn Ile
225                 230
```

<210> SEQ ID NO 5
<211> LENGTH: 109
<212> TYPE: DNA
<213> ORGANISM: Artificial Sequence
<220> FEATURE:
<223> OTHER INFORMATION: Schmallenberg "S" 3' UTR

<400> SEQUENCE: 5

```
tgaacctctt catcacagat cttcaatttc cgtgcaatat gtctatgtat tgcacaccat     60
tatactgcaa ggcttctgtt aagatagtta ataagtggag aacactact               109
```

<210> SEQ ID NO 6
<211> LENGTH: 200
<212> TYPE: DNA
<213> ORGANISM: Artificial Sequence
<220> FEATURE:
<223> OTHER INFORMATION: Ribozyme/T7 Terminator

<400> SEQUENCE: 6

```
gggtcggcat ggcatctcca cctcctcgcg gtccgacctg ggcatccgaa ggaggacgtc     60
gtccactcgg atggctaagg gagagctcgg atccggctgc taacaaagcc cgaaaggaag    120
```

```
ctgagttggc tgctgccacc gctgagcaat aactagcata accccttggg gcctctaaac      180
gggtcttgag gggttttttg                                                  200
```

<210> SEQ ID NO 7
<211> LENGTH: 18
<212> TYPE: DNA
<213> ORGANISM: Artificial Sequence
<220> FEATURE:
<223> OTHER INFORMATION: T7 minimal promoter

<400> SEQUENCE: 7

```
taatacgact cactatag                                                    18
```

<210> SEQ ID NO 8
<211> LENGTH: 23
<212> TYPE: DNA
<213> ORGANISM: Artificial Sequence
<220> FEATURE:
<223> OTHER INFORMATION: Schmallenberg "M" 5' UTR

<400> SEQUENCE: 8

```
agtagtgaac taccacaatc aaa                                              23
```

<210> SEQ ID NO 9
<211> LENGTH: 4209
<212> TYPE: DNA
<213> ORGANISM: Artificial Sequence
<220> FEATURE:
<223> OTHER INFORMATION: Schmallenberg “M” ORF nucleotides

<400> SEQUENCE: 9
atgcttctca acattgtctt gatatctaac ttagcctgtt tagcttttgc actcccactt 60
aaggaaggca ctagagggtc taggtgcttc ctgaatggcg aactggttaa aactgttaac 120
acatcaaagg tcgtttcaga atgctgtgtg aaagacgaca tatctatcat taaatcaaat 180
gctgaacatt ataaatcagg agatcggttg gctgctgtaa taaaatatta tcgtttatat 240
caggtgaagg attggcattc ttgcaatcca atttatgatg accacggttc ctttatgata 300
ttagatatag ataatactgg cacattaatc cctaaaatgc atacatgcag agttgaatgc 360
gaaatagcac tgaataaaga tactggcgaa gttatattga attcatatcg aattaaccac 420
taccgaatct cgggcacaat gcatgtatca ggttggttta aaaacaaaat tgagattcct 480
ttggaaaaca catgcgaatc cattgaggta acatgtggat taaaaacact taattttcat 540
gcatgtttcc atacccataa gtcatgcacc cgctatttta aaggatcaat cctgccggaa 600
ttgatgatcg aatcattttg tacgaatctt gaattaatac tgctagtaac tttcatatta 660
gttgggtctg tcatgatgat gatattgacg aaaacatata tagtatatgt gttcattcct 720
atattttatc catttgtgaa attatatgct tatatgtaca acaaatattt taaattgtgt 780
aaaaattgcc tgttagcagt acatcccttt acaaattgcc catcgacatg catctgtgga 840
atgatttaca ctaccactga atcactcaaa ttgcatcgca tgtgtaacaa ttgttctggc 900
tataaagcat tgccgaaaac aaggaaattg tgtaaaagta aaatatccaa tatagtgcta 960
tgtgtgataa catcactgat atttttctca tttatcacac ctatatcgag tcaatgtatc 1020
gatatagaaa aactgccaga cgagtatatt acatgtaaaa gagagctagc taatatcaaa 1080
agcttgacaa ttgatgacac atatagcttt atatattcct gtacatgcat aattgtgtta 1140
atattactta aaaaggcagc aaagtatatc ttgtactgca actgcagctt ttgtggtatg 1200

```
gtacatgaac gacgtggatt gaagataatg gacaacttta caaacaagtg cctaagttgt    1260
gtatgcgcag aaaacaaggg cttaacaatt cacagagcct ctgagaaatg tctgttcaaa    1320
tttgaatcaa gttataatag gaccgggttg ataatcttta tgcttctgtt agtcccaaca    1380
attgtaatga cgcaagaaac tagtattaac tgcaaaaaca ttcaatcaac tcagcttaca    1440
atagagcacc tgagtaagtg catggcattt tatcaaaata aaacaagctc accagttgta    1500
atcaatgaaa aatttcaga tgcttcagta gacgaacaag aattaataaa aagtttaaac    1560
ttgaactgta atgtcataga taggtttatt tccgaatcta gtgttattga gactcaagtt    1620
tattatgagt atataaaatc acagttgtgc cctctccaag tgcatgatat tttcactatc    1680
aattcagcaa gtaacataca atggaaagca ctggcccgaa gtttcacctt aggagtgtgc    1740
aatacgaatc ctcataaaca tatatgtaga tgcttggagt ctatgcaaat gtgcacatca    1800
accaagacag accacgctag ggaaatgtca atatattatg atggtcatcc agatcgcttt    1860
gagcatgaca tgaaaataat attgaatata tgagatata tagtccctgg attaggtcga    1920
gtcttgcttg atcaaatcaa acaaacaaaa gactaccaag ctttacgcca catacaaggt    1980
aagctttctc ctaaatcgca gtcaaattta caacttaaag gatttctgga atttgttgat    2040
tttatccttg gtgcaaacgt gacaatagaa aaacccctc aaacattaac tacattatct    2100
ttgataaaag gagcccacag aaacttggat caaaagatc caggtccaac accaatactg    2160
gtatgcaaat caccacaaaa agtggtatgc tactcaccac gtggtgtcac acacccagga    2220
gattatatat catgcraatc taagatgtat aagtggccat ctttaggggt atacaaacat    2280
aatagagacc agcaacaagc ctgcagcagt gacacacatt gcctagagat gtttgaacca    2340
gcagaaagaa caataactac aaaaatatgc aaagtaagtg atatgactta ttcagaatcg    2400
ccatatagta ctggaatacc atcatgcaac gtgaagagat ttggatcatg taatgtaagg    2460
ggtcatcaat ggcaaattgc agaatgctca aatggcttat tttactatgt ttcagctaaa    2520
gcccattcga aaactaacga tataacactg tactgtttat cagcaaattg cctggacttg    2580
cgttatgcat tcagatccag tagttgttca gatatagtat gggatacaag ttatcgaaat    2640
aaattaacac ctaaatctat taatcatcca gatattgaaa actacatagc agcgcttcag    2700
tcagatattg caaatgattt aactatgcac tactttaaac cattaaaaaa ccttccagca    2760
ataattcctc aatacaaaac aatgacattg aatggggaca aggtatcaaa tggtattaga    2820
aatagttata tcgagtcgca catccctgca attaatggtt tatcagcagg gattaatatt    2880
gccatgccaa atggagaaag cctctttttc attattatct atgtcagaag agtaataaat    2940
aaagcatcgt atcgatttct atatgaaaca ggacccacaa ttggaataaa tgccaagcac    3000
gaagaggtat gtaccgggaa gtgcccaagc ccaataccac atcaagatgg ttgggtcaca    3060
ttctcaaagg aaagatcaag taattggggc tgtgaagaat ggggttgctt ggcaataaat    3120
gatggttgtt tatatgggtc atgtcaagac ataataaggc ctgaatataa gatatacaag    3180
aagtctagta ttgaacaaaa ggatgttgaa gtttgtataa ccatggccca tgaatcattc    3240
tgcagtaccg ttgatgttct ccaacctta attagcgaca ggatacaatt agatatccaa    3300
acgattcaaa tggactctat gccaaatata attgcagtca gaatgggaa agtttatgtt    3360 ggagatatca atgacttagg ttcgacagca aagaaatgtg gctcagtcca attatattct    3420
gaagggatca ttggatcggg aacccccaaaa tttgattatg tttgccatgc attcaatcgt    3480
aaagatgtca tccttcgaag atgctttgat aactcatatc agtcttgtct ctcttggaa    3540 caagataata cattaactat tgcttctacc agtcatatgg aagtgcataa aaaagtttca    3600
```

-continued

```
agcgtgggta caatcaatta taaaattatg ttaggggatt ttgactacaa tgcatattca   3660
acacaagcaa cagtcacaat agatgagatc aggtgtggtg gttgttatgg ctgccctgaa   3720
ggaatggctt gcgcactcaa attgagtacc aataccatcg ggagttgttc aataaaaagt   3780
aactgcgata catacattaa aataatagca gtcgatccga tgcagagcga gtattccatt   3840
aagttaaact gcccactagc aacagagaca gtttcagtaa gtgtgtgctc agcttctgct   3900
tacacaaaac cttcaatatc taaaaatcaa ccaaaaattg ttttgaattc cttagatgaa   3960
acatcttaca tcgagcaaca tgataaaaag tgttctacat ggctttgcag agtttatraa   4020
gaagggatta gcgtaatatt tcagcctcta tttggcaacc tatctttcta ttggagactg   4080
acaatatata taataatctc tttgattatg ctaattctgt ttctatacat attaatacca   4140
ctgtgcaaac ggctaaaagg tttattggaa tacaatgaga gaatatacca aatggaaaat   4200
aaatttaag                                                           4209
```

<210> SEQ ID NO 10
<211> LENGTH: 1403
<212> TYPE: PRT
<213> ORGANISM: Artificial Sequence
<220> FEATURE:
<223> OTHER INFORMATION: SBV-Germ amino acid sequence

<400> SEQUENCE: 10

```
Met Leu Leu Asn Ile Val Leu Ile Ser Asn Leu Ala Cys Leu Ala Phe
1               5                   10                  15

Ala Leu Pro Leu Lys Glu Gly Thr Arg Gly Ser Arg Cys Phe Leu Asn
            20                  25                  30

Gly Glu Leu Val Lys Thr Val Asn Thr Ser Lys Val Val Ser Glu Cys
        35                  40                  45

Cys Val Lys Asp Asp Ile Ser Ile Ile Lys Ser Asn Ala Glu His Tyr
    50                  55                  60

Lys Ser Gly Asp Arg Leu Ala Ala Val Ile Lys Tyr Tyr Arg Leu Tyr
65                  70                  75                  80

Gln Val Lys Asp Trp His Ser Cys Asn Pro Ile Tyr Asp Asp His Gly
                85                  90                  95

Ser Phe Met Ile Leu Asp Ile Asp Asn Thr Gly Thr Leu Ile Pro Lys
            100                 105                 110

Met His Thr Cys Arg Val Glu Cys Glu Ile Ala Leu Asn Lys Asp Thr
        115                 120                 125

Gly Glu Val Ile Leu Asn Ser Tyr Arg Ile Asn His Tyr Arg Ile Ser
    130                 135                 140

Gly Thr Met His Val Ser Gly Trp Phe Lys Asn Lys Ile Glu Ile Pro
145                 150                 155                 160

Leu Glu Asn Thr Cys Glu Ser Ile Glu Val Thr Cys Gly Leu Lys Thr
                165                 170                 175

Leu Asn Phe His Ala Cys Phe Thr His Lys Ser Cys Thr Arg Tyr
            180                 185                 190

Phe Lys Gly Ser Ile Leu Pro Glu Leu Met Ile Glu Ser Phe Cys Thr
        195                 200                 205

Asn Leu Glu Leu Ile Leu Leu Val Thr Phe Ile Leu Val Gly Ser Val
    210                 215                 220

Met Met Met Ile Leu Thr Lys Thr Tyr Ile Val Tyr Val Phe Ile Pro
225                 230                 235                 240

Ile Phe Tyr Pro Phe Val Lys Leu Tyr Ala Tyr Met Tyr Asn Lys Tyr
```

```
                    245                 250                 255
Phe Lys Leu Cys Lys Asn Cys Leu Leu Ala Val His Pro Phe Thr Asn
                260                 265                 270
Cys Pro Ser Thr Cys Ile Cys Gly Met Ile Tyr Thr Thr Thr Glu Ser
            275                 280                 285
Leu Lys Leu His Arg Met Cys Asn Asn Cys Ser Gly Tyr Lys Ala Leu
        290                 295                 300
Pro Lys Thr Arg Lys Leu Cys Lys Ser Lys Ile Ser Asn Ile Val Leu
305                 310                 315                 320
Cys Val Ile Thr Ser Leu Ile Phe Phe Ser Phe Ile Thr Pro Ile Ser
                325                 330                 335
Ser Gln Cys Ile Asp Ile Glu Lys Leu Pro Asp Glu Tyr Ile Thr Cys
                340                 345                 350
Lys Arg Glu Leu Ala Asn Ile Lys Ser Leu Thr Ile Asp Asp Thr Tyr
            355                 360                 365
Ser Phe Ile Tyr Ser Cys Thr Cys Ile Ile Val Leu Ile Leu Leu Lys
        370                 375                 380
Lys Ala Ala Lys Tyr Ile Leu Tyr Cys Asn Cys Ser Phe Cys Gly Met
385                 390                 395                 400
Val His Glu Arg Arg Gly Leu Lys Ile Met Asp Asn Phe Thr Asn Lys
                405                 410                 415
Cys Leu Ser Cys Val Cys Ala Glu Asn Lys Gly Leu Thr Ile His Arg
            420                 425                 430
Ala Ser Glu Lys Cys Leu Phe Lys Phe Glu Ser Ser Tyr Asn Arg Thr
        435                 440                 445
Gly Leu Ile Ile Phe Met Leu Leu Leu Val Pro Thr Ile Val Met Thr
        450                 455                 460
Gln Glu Thr Ser Ile Asn Cys Lys Asn Ile Gln Ser Thr Gln Leu Thr
465                 470                 475                 480
Ile Glu His Leu Ser Lys Cys Met Ala Phe Tyr Gln Asn Lys Thr Ser
                485                 490                 495
Ser Pro Val Val Ile Asn Glu Ile Ile Ser Asp Ala Ser Val Asp Glu
            500                 505                 510
Gln Glu Leu Ile Lys Ser Leu Asn Leu Asn Cys Asn Val Ile Asp Arg
        515                 520                 525
Phe Ile Ser Glu Ser Ser Val Ile Glu Thr Gln Val Tyr Tyr Glu Tyr
        530                 535                 540
Ile Lys Ser Gln Leu Cys Pro Leu Gln Val His Asp Ile Phe Thr Ile
545                 550                 555                 560
Asn Ser Ala Ser Asn Ile Gln Trp Lys Ala Leu Ala Arg Ser Phe Thr
                565                 570                 575
Leu Gly Val Cys Asn Thr Asn Pro His Lys His Ile Cys Arg Cys Leu
            580                 585                 590
Glu Ser Met Gln Met Cys Thr Ser Thr Lys Thr Asp His Ala Arg Glu
        595                 600                 605
Met Ser Ile Tyr Tyr Asp Gly His Pro Asp Arg Phe Glu His Asp Met
        610                 615                 620
Lys Ile Ile Leu Asn Ile Met Arg Tyr Ile Val Pro Gly Leu Gly Arg
625                 630                 635                 640
Val Leu Leu Asp Gln Ile Lys Gln Thr Lys Asp Tyr Gln Ala Leu Arg
                645                 650                 655
His Ile Gln Gly Lys Leu Ser Pro Lys Ser Gln Ser Asn Leu Gln Leu
            660                 665                 670
```

```
Lys Gly Phe Leu Glu Phe Val Asp Phe Ile Leu Gly Ala Asn Val Thr
        675                 680                 685

Ile Glu Lys Thr Pro Gln Thr Leu Thr Thr Leu Ser Leu Ile Lys Gly
        690                 695                 700

Ala His Arg Asn Leu Asp Gln Lys Asp Pro Gly Pro Thr Pro Ile Leu
705                 710                 715                 720

Val Cys Lys Ser Pro Gln Lys Val Val Cys Tyr Ser Pro Arg Gly Val
                725                 730                 735

Thr His Pro Gly Asp Tyr Ile Ser Cys Lys Ser Lys Met Tyr Lys Trp
                740                 745                 750

Pro Ser Leu Gly Val Tyr Lys His Asn Arg Asp Gln Gln Gln Ala Cys
            755                 760                 765

Ser Ser Asp Thr His Cys Leu Glu Met Phe Glu Pro Ala Glu Arg Thr
        770                 775                 780

Ile Thr Thr Lys Ile Cys Lys Val Ser Asp Met Thr Tyr Ser Glu Ser
785                 790                 795                 800

Pro Tyr Ser Thr Gly Ile Pro Ser Cys Asn Val Lys Arg Phe Gly Ser
                805                 810                 815

Cys Asn Val Arg Gly His Gln Trp Gln Ile Ala Glu Cys Ser Asn Gly
            820                 825                 830

Leu Phe Tyr Tyr Val Ser Ala Lys Ala His Ser Lys Thr Asn Asp Ile
        835                 840                 845

Thr Leu Tyr Cys Leu Ser Ala Asn Cys Leu Asp Leu Arg Tyr Ala Phe
    850                 855                 860

Arg Ser Ser Ser Cys Ser Asp Ile Val Trp Asp Thr Ser Tyr Arg Asn
865                 870                 875                 880

Lys Leu Thr Pro Lys Ser Ile Asn His Pro Asp Ile Glu Asn Tyr Ile
                885                 890                 895

Ala Ala Leu Gln Ser Asp Ile Ala Asn Asp Leu Thr Met His Tyr Phe
            900                 905                 910

Lys Pro Leu Lys Asn Leu Pro Ala Ile Ile Pro Gln Tyr Lys Thr Met
        915                 920                 925

Thr Leu Asn Gly Asp Lys Val Ser Asn Gly Ile Arg Asn Ser Tyr Ile
    930                 935                 940

Glu Ser His Ile Pro Ala Ile Asn Gly Leu Ser Ala Gly Ile Asn Ile
945                 950                 955                 960

Ala Met Pro Asn Gly Glu Ser Leu Phe Ser Ile Ile Tyr Val Arg
                965                 970                 975

Arg Val Ile Asn Lys Ala Ser Tyr Arg Phe Leu Tyr Glu Thr Gly Pro
            980                 985                 990

Thr Ile Gly Ile Asn Ala Lys His Glu Glu Val Cys Thr Gly Lys Cys
        995                 1000                1005

Pro Ser Pro Ile Pro His Gln Asp Gly Trp Val Thr Phe Ser Lys
    1010                1015                1020

Glu Arg Ser Ser Asn Trp Gly Cys Glu Glu Trp Gly Cys Leu Ala
    1025                1030                1035

Ile Asn Asp Gly Cys Leu Tyr Gly Ser Cys Gln Asp Ile Ile Arg
    1040                1045                1050

Pro Glu Tyr Lys Ile Tyr Lys Lys Ser Ser Ile Glu Gln Lys Asp
    1055                1060                1065

Val Glu Val Cys Ile Thr Met Ala His Glu Ser Phe Cys Ser Thr
    1070                1075                1080
```

```
Val Asp Val Leu Gln Pro Leu Ile Ser Asp Arg Ile Gln Leu Asp
1085                1090                1095

Ile Gln Thr Ile Gln Met Asp Ser Met Pro Asn Ile Ile Ala Val
1100                1105                1110

Lys Asn Gly Lys Val Tyr Val Gly Asp Ile Asn Asp Leu Gly Ser
1115                1120                1125

Thr Ala Lys Lys Cys Gly Ser Val Gln Leu Tyr Ser Glu Gly Ile
1130                1135                1140

Ile Gly Ser Gly Thr Pro Lys Phe Asp Tyr Val Cys His Ala Phe
1145                1150                1155

Asn Arg Lys Asp Val Ile Leu Arg Arg Cys Phe Asp Asn Ser Tyr
1160                1165                1170

Gln Ser Cys Leu Leu Leu Glu Gln Asp Asn Thr Leu Thr Ile Ala
1175                1180                1185

Ser Thr Ser His Met Glu Val His Lys Lys Val Ser Ser Val Gly
1190                1195                1200

Thr Ile Asn Tyr Lys Ile Met Leu Gly Asp Phe Asp Tyr Asn Ala
1205                1210                1215

Tyr Ser Thr Gln Ala Thr Val Thr Ile Asp Glu Ile Arg Cys Gly
1220                1225                1230

Gly Cys Tyr Gly Cys Pro Glu Gly Met Ala Cys Ala Leu Lys Leu
1235                1240                1245

Ser Thr Asn Thr Ile Gly Ser Cys Ser Ile Lys Ser Asn Cys Asp
1250                1255                1260

Thr Tyr Ile Lys Ile Ile Ala Val Asp Pro Met Gln Ser Glu Tyr
1265                1270                1275

Ser Ile Lys Leu Asn Cys Pro Leu Ala Thr Glu Thr Val Ser Val
1280                1285                1290

Ser Val Cys Ser Ala Ser Ala Tyr Thr Lys Pro Ser Ile Ser Lys
1295                1300                1305

Asn Gln Pro Lys Ile Val Leu Asn Ser Leu Asp Glu Thr Ser Tyr
1310                1315                1320

Ile Glu Gln His Asp Lys Lys Cys Ser Thr Trp Leu Cys Arg Val
1325                1330                1335

Tyr Lys Glu Gly Ile Ser Val Ile Phe Gln Pro Leu Phe Gly Asn
1340                1345                1350

Leu Ser Phe Tyr Trp Arg Leu Thr Ile Tyr Ile Ile Ile Ser Leu
1355                1360                1365

Ile Met Leu Ile Leu Phe Leu Tyr Ile Leu Ile Pro Leu Cys Lys
1370                1375                1380

Arg Leu Lys Gly Leu Leu Glu Tyr Asn Glu Arg Ile Tyr Gln Met
1385                1390                1395

Glu Asn Lys Phe Lys
1400
```

<210> SEQ ID NO 11
<211> LENGTH: 1403
<212> TYPE: PRT
<213> ORGANISM: Artificial Sequence
<220> FEATURE:
<223> OTHER INFORMATION: SBV-Neth amino acid sequence

<400> SEQUENCE: 11

```
Met Leu Leu Asn Ile Val Leu Ile Ser Asn Leu Ala Cys Leu Ala Phe
1               5                   10                  15
```

-continued

```
Ala Leu Pro Leu Lys Glu Gly Thr Arg Gly Ser Arg Cys Phe Leu Asn
             20                  25                  30

Gly Glu Leu Val Lys Thr Val Asn Thr Ser Lys Val Val Ser Glu Cys
         35                  40                  45

Cys Val Lys Asp Asp Ile Ser Ile Ile Lys Ser Asn Ala Glu His Tyr
     50                  55                  60

Lys Ser Gly Asp Arg Leu Ala Ala Val Ile Lys Tyr Tyr Arg Leu Tyr
 65                  70                  75                  80

Gln Val Lys Asp Trp His Ser Cys Asn Pro Ile Tyr Asp His Gly
                 85                  90                  95

Ser Phe Met Ile Leu Asp Ile Asp Asn Thr Gly Thr Leu Ile Pro Lys
                100                 105                 110

Met His Thr Cys Arg Val Glu Cys Glu Ile Ala Leu Asn Lys Asp Thr
             115                 120                 125

Gly Glu Val Ile Leu Asn Ser Tyr Arg Ile Asn His Tyr Arg Ile Ser
         130                 135                 140

Gly Thr Met His Val Ser Gly Trp Phe Lys Asn Lys Ile Glu Ile Pro
145                 150                 155                 160

Leu Glu Asn Thr Cys Glu Ser Ile Glu Val Thr Cys Gly Leu Lys Thr
                165                 170                 175

Leu Asn Phe His Ala Cys Phe His Thr His Lys Ser Cys Thr Arg Tyr
            180                 185                 190

Phe Lys Gly Ser Ile Leu Pro Glu Leu Met Ile Glu Ser Phe Cys Thr
        195                 200                 205

Asn Leu Glu Leu Ile Leu Leu Val Thr Phe Ile Leu Val Gly Ser Val
210                 215                 220

Met Met Met Ile Leu Thr Lys Thr Tyr Ile Val Tyr Val Phe Ile Pro
225                 230                 235                 240

Ile Phe Tyr Pro Phe Val Lys Leu Tyr Ala Tyr Met Tyr Asn Lys Tyr
                245                 250                 255

Phe Lys Leu Cys Lys Asn Cys Leu Leu Ala Val His Pro Phe Thr Asn
            260                 265                 270

Cys Pro Ser Thr Cys Ile Cys Gly Met Ile Tyr Thr Thr Thr Glu Ser
        275                 280                 285

Leu Lys Leu His Arg Met Cys Asn Asn Cys Ser Gly Tyr Lys Ala Leu
    290                 295                 300

Pro Lys Thr Arg Lys Leu Cys Lys Ser Lys Ile Ser Asn Ile Val Leu
305                 310                 315                 320

Cys Val Ile Thr Ser Leu Ile Phe Phe Ser Phe Ile Thr Pro Ile Ser
                325                 330                 335

Ser Gln Cys Ile Asp Ile Glu Lys Leu Pro Asp Glu Tyr Ile Thr Cys
            340                 345                 350

Lys Arg Glu Leu Ala Asn Ile Lys Ser Leu Thr Ile Asp Asp Thr Tyr
        355                 360                 365

Ser Phe Ile Tyr Ser Cys Thr Cys Ile Ile Val Leu Ile Leu Leu Lys
    370                 375                 380

Lys Ala Ala Lys Tyr Ile Leu Tyr Cys Asn Cys Ser Phe Cys Gly Met
385                 390                 395                 400

Val His Glu Arg Arg Gly Leu Lys Ile Met Asp Asn Phe Thr Asn Lys
                405                 410                 415

Cys Leu Ser Cys Val Cys Ala Glu Asn Lys Gly Leu Thr Ile His Arg
            420                 425                 430

Ala Ser Glu Lys Cys Leu Phe Lys Phe Glu Ser Ser Tyr Asn Arg Thr
```

```
            435                 440                 445
Gly Leu Ile Ile Phe Met Leu Leu Val Pro Thr Ile Val Met Thr
450                 455                 460
Gln Glu Thr Ser Ile Asn Cys Lys Asn Ile Gln Ser Thr Gln Leu Thr
465                 470                 475                 480
Ile Glu His Leu Ser Lys Cys Met Ala Phe Tyr Gln Asn Lys Thr Ser
                485                 490                 495
Ser Pro Val Val Ile Asn Glu Ile Ile Ser Asp Ala Ser Val Asp Glu
                500                 505                 510
Gln Glu Leu Ile Lys Ser Leu Asn Leu Asn Cys Asn Val Ile Asp Arg
                515                 520                 525
Phe Ile Ser Glu Ser Ser Val Ile Glu Thr Gln Val Tyr Tyr Glu Tyr
530                 535                 540
Ile Lys Ser Gln Leu Cys Pro Leu Gln Val His Asp Ile Phe Thr Ile
545                 550                 555                 560
Asn Ser Ala Ser Asn Ile Gln Trp Lys Ala Leu Ala Arg Ser Phe Thr
                565                 570                 575
Leu Gly Val Cys Asn Thr Asn Pro His Lys His Ile Cys Arg Cys Leu
                580                 585                 590
Glu Ser Met Gln Met Cys Thr Ser Thr Lys Thr Asp His Ala Arg Glu
                595                 600                 605
Met Ser Ile Tyr Tyr Asp Gly His Pro Asp Arg Phe Glu His Asp Met
610                 615                 620
Lys Ile Ile Leu Asn Ile Met Arg Tyr Ile Val Pro Gly Leu Gly Arg
625                 630                 635                 640
Val Leu Leu Asp Gln Ile Lys Gln Thr Lys Asp Tyr Gln Ala Leu Arg
                645                 650                 655
His Ile Gln Gly Lys Leu Ser Pro Lys Ser Gln Ser Asn Leu Gln Leu
                660                 665                 670
Lys Gly Phe Leu Glu Phe Val Asp Phe Ile Leu Gly Ala Asn Val Thr
                675                 680                 685
Ile Glu Lys Thr Pro Gln Thr Leu Thr Thr Leu Ser Leu Ile Lys Gly
690                 695                 700
Ala His Arg Asn Leu Asp Gln Lys Asp Pro Gly Pro Thr Pro Ile Leu
705                 710                 715                 720
Val Cys Lys Ser Pro Gln Lys Val Val Cys Tyr Ser Pro Arg Gly Val
                725                 730                 735
Thr His Pro Gly Asp Tyr Ile Ser Cys Glu Ser Lys Met Tyr Lys Trp
                740                 745                 750
Pro Ser Leu Gly Val Tyr Lys His Asn Arg Asp Gln Gln Ala Cys
                755                 760                 765
Ser Ser Asp Thr His Cys Leu Glu Met Phe Glu Pro Ala Glu Arg Thr
                770                 775                 780
Ile Thr Thr Lys Ile Cys Lys Val Ser Asp Met Thr Tyr Ser Glu Ser
785                 790                 795                 800
Pro Tyr Ser Thr Gly Ile Pro Ser Cys Asn Val Lys Arg Phe Gly Ser
                805                 810                 815
Cys Asn Val Arg Gly His Gln Trp Gln Ile Ala Glu Cys Ser Asn Gly
                820                 825                 830
Leu Phe Tyr Tyr Val Ser Ala Lys Ala His Ser Lys Thr Asn Asp Ile
                835                 840                 845
Thr Leu Tyr Cys Leu Ser Ala Asn Cys Leu Asp Leu Arg Tyr Ala Phe
                850                 855                 860
```

```
Arg Ser Ser Ser Cys Ser Asp Ile Val Trp Asp Thr Ser Tyr Arg Asn
865                 870                 875                 880

Lys Leu Thr Pro Lys Ser Ile Asn His Pro Asp Ile Glu Asn Tyr Ile
            885                 890                 895

Ala Ala Leu Gln Ser Asp Ile Ala Asn Asp Leu Thr Met His Tyr Phe
                900                 905                 910

Lys Pro Leu Lys Asn Leu Pro Ala Ile Ile Pro Gln Tyr Lys Thr Met
            915                 920                 925

Thr Leu Asn Gly Asp Lys Val Ser Asn Gly Ile Arg Asn Ser Tyr Ile
        930                 935                 940

Glu Ser His Ile Pro Ala Ile Asn Gly Leu Ser Ala Gly Ile Asn Ile
945                 950                 955                 960

Ala Met Pro Asn Gly Glu Ser Leu Phe Ser Ile Ile Tyr Val Arg
                965                 970                 975

Arg Val Ile Asn Lys Ala Ser Tyr Arg Phe Leu Tyr Glu Thr Gly Pro
            980                 985                 990

Thr Ile Gly Ile Asn Ala Lys His Glu Glu Val Cys Thr Gly Lys Cys
        995                 1000                1005

Pro Ser Pro Ile Pro His Gln Asp Gly Trp Val Thr Phe Ser Lys
    1010                1015                1020

Glu Arg Ser Ser Asn Trp Gly Cys Glu Glu Trp Gly Cys Leu Ala
    1025                1030                1035

Ile Asn Asp Gly Cys Leu Tyr Gly Ser Cys Gln Asp Ile Ile Arg
    1040                1045                1050

Pro Glu Tyr Lys Ile Tyr Lys Lys Ser Ser Ile Glu Gln Lys Asp
    1055                1060                1065

Val Glu Val Cys Ile Thr Met Ala His Glu Ser Phe Cys Ser Thr
    1070                1075                1080

Val Asp Val Leu Gln Pro Leu Ile Ser Asp Arg Ile Gln Leu Asp
    1085                1090                1095

Ile Gln Thr Ile Gln Met Asp Ser Met Pro Asn Ile Ile Ala Val
    1100                1105                1110

Lys Asn Gly Lys Val Tyr Val Gly Asp Ile Asn Asp Leu Gly Ser
    1115                1120                1125

Thr Ala Lys Lys Cys Gly Ser Val Gln Leu Tyr Ser Glu Gly Ile
    1130                1135                1140

Ile Gly Ser Gly Thr Pro Lys Phe Asp Tyr Val Cys His Ala Phe
    1145                1150                1155

Asn Arg Lys Asp Val Ile Leu Arg Arg Cys Phe Asp Asn Ser Tyr
    1160                1165                1170

Gln Ser Cys Leu Leu Leu Glu Gln Asp Asn Thr Leu Thr Ile Ala
    1175                1180                1185

Ser Thr Ser His Met Glu Val His Lys Lys Val Ser Ser Val Gly
    1190                1195                1200

Thr Ile Asn Tyr Lys Ile Met Leu Gly Asp Phe Asp Tyr Asn Ala
    1205                1210                1215

Tyr Ser Thr Gln Ala Thr Val Thr Ile Asp Glu Ile Arg Cys Gly
    1220                1225                1230

Gly Cys Tyr Gly Cys Pro Glu Gly Met Ala Cys Ala Leu Lys Leu
    1235                1240                1245

Ser Thr Asn Thr Ile Gly Ser Cys Ser Ile Lys Ser Asn Cys Asp
    1250                1255                1260
```

| Thr | Tyr | Ile | Lys | Ile | Ile | Ala | Val | Asp | Pro | Met | Gln | Ser | Glu | Tyr |
|---|---|---|---|---|---|---|---|---|---|---|---|---|---|---|
| | 1265 | | | | 1270 | | | | 1275 | | | | | |

| Ser | Ile | Lys | Leu | Asn | Cys | Pro | Leu | Ala | Thr | Glu | Thr | Val | Ser | Val |
|---|---|---|---|---|---|---|---|---|---|---|---|---|---|---|
| 1280 | | | | | 1285 | | | | | 1290 | | | | |

| Ser | Val | Cys | Ser | Ala | Ser | Ala | Tyr | Thr | Lys | Pro | Ser | Ile | Ser | Lys |
|---|---|---|---|---|---|---|---|---|---|---|---|---|---|---|
| 1295 | | | | | 1300 | | | | | 1305 | | | | |

| Asn | Gln | Pro | Lys | Ile | Val | Leu | Asn | Ser | Leu | Asp | Glu | Thr | Ser | Tyr |
|---|---|---|---|---|---|---|---|---|---|---|---|---|---|---|
| 1310 | | | | | 1315 | | | | | 1320 | | | | |

| Ile | Glu | Gln | His | Asp | Lys | Lys | Cys | Ser | Thr | Trp | Leu | Cys | Arg | Val |
|---|---|---|---|---|---|---|---|---|---|---|---|---|---|---|
| 1325 | | | | | 1330 | | | | | 1335 | | | | |

| Tyr | Glu | Glu | Gly | Ile | Ser | Val | Ile | Phe | Gln | Pro | Leu | Phe | Gly | Asn |
|---|---|---|---|---|---|---|---|---|---|---|---|---|---|---|
| 1340 | | | | | 1345 | | | | | 1350 | | | | |

| Leu | Ser | Phe | Tyr | Trp | Arg | Leu | Thr | Ile | Tyr | Ile | Ile | Ile | Ser | Leu |
|---|---|---|---|---|---|---|---|---|---|---|---|---|---|---|
| 1355 | | | | | 1360 | | | | | 1365 | | | | |

| Ile | Met | Leu | Ile | Leu | Phe | Leu | Tyr | Ile | Leu | Ile | Pro | Leu | Cys | Lys |
|---|---|---|---|---|---|---|---|---|---|---|---|---|---|---|
| 1370 | | | | | 1375 | | | | | 1380 | | | | |

| Arg | Leu | Lys | Gly | Leu | Leu | Glu | Tyr | Asn | Glu | Arg | Ile | Tyr | Gln | Met |
|---|---|---|---|---|---|---|---|---|---|---|---|---|---|---|
| 1385 | | | | | 1390 | | | | | 1395 | | | | |

| Glu | Asn | Lys | Phe | Lys |
|---|---|---|---|---|
| 1400 | | | | |

<210> SEQ ID NO 12
<211> LENGTH: 141
<212> TYPE: DNA
<213> ORGANISM: Artificial Sequence
<220> FEATURE:
<223> OTHER INFORMATION: SBV-Germ "M" 3' UTR

<400> SEQUENCE: 12
tgataagcct tataacaatg agcaattata aatgaataaa taaaaacaat aaaagataaa    60
caaataacaa catatatatg tggttacaca tatatatgta attattcagc tgagaagttt   120
ttcatgtggt agaacactac t                                              141

<210> SEQ ID NO 13
<211> LENGTH: 141
<212> TYPE: DNA
<213> ORGANISM: Artificial Sequence
<220> FEATURE:
<223> OTHER INFORMATION: SBV-Neth "M" 3' UTR

<400> SEQUENCE: 13
tgataagccc tataacaatg agcaattata aatgaataaa taaaaacaat aaaagataaa    60
caaataacaa catatatatg tggttacaca tatatatgta attattcagc tgagaagttt   120
ttcatgtggt agaacactac t                                              141

<210> SEQ ID NO 14
<211> LENGTH: 6762
<212> TYPE: DNA
<213> ORGANISM: Artificial Sequence
<220> FEATURE:
<223> OTHER INFORMATION: Schmallenberg "L" ORF nucleotide

<400> SEQUENCE: 14
atggagacat acaagattaa cattttttaga gataggatca accagtgtcg aagtgctgaa    60
gaagccaaag acattgttgc tgatcttctc atggctagac atgactactt tggtagagag   120
gtatgttatt acctggatat cgaattccgg caggatgttc cagcttacga catacttctt   180
gaatttctgc cagctggcac tgcttttcaac attcgcaatt gtacaccaga caattttatc   240

| | |
|---|---|
| attcacaatg gcaagcttta tatcattgac tataaagtat caactgatca tgcatatggt | 300 |
| caaaaaactt atgaaaagta cacccagatc tttggagacg cattgtcaga attgccgttt | 360 |
| gattttgaag ttgtgatcat ccgtgctgac cctctgcgag atactatcca tgttaattca | 420 |
| aatcaattct tggaaatatt tgggccgctc aacataaacc ttgattttac ttggttcttt | 480 |
| aatttgcgat ccctgatata tgagaaatat aaggatgacg acagattcct agaaattgtg | 540 |
| aatcaaggtg aatttacgat gactggaccc tggattgatg aggatacccc ggagctctat | 600 |
| tcacaccctg tcttttttgga attctatgat tctttagatg agatggctaa actgacattc | 660 |
| catgagtcta tgacatttga tgcaactcgc ggtgagaaat ggaatcaaaa tctacaaaag | 720 |
| gttataaata gatatggcaa tgattataac attttttgtga agaggccgc tgcaggaatc | 780 |
| tttagatgtg aagggaacta cccaaaacca aatcatgatg aaatcacaat cggttggaat | 840 |
| caaatggttc aaagagtgag tactgagaga aacctgactc aagatgtcag caagcaaaaa | 900 |
| ccatctattc atttcatatg gggtcaacct gacgaaacat caaatgcgac aacaccaaaa | 960 |
| ctaatcaaga ttgcaaaagc actccaaaat atttctggcg agtctacata tataagcgca | 1020 |
| ttcagagcat tgggtatgct tatggacttt tctgagaaca cagctttata tgaagcacac | 1080 |
| actagcaaac taaaaagtat ggcaagacag acatcgaaaa gaattgatac taaactggaa | 1140 |
| ccaatcaaaa taggcacggc gacaatttat tgggaacagc agtttaaact ggatactgaa | 1200 |
| ataatgaata caaaagacaa atcacatttg ctaaaagatt ttcttggcat aggggggtcac | 1260 |
| gtgcaatttt caaaaaagac cattgacgat ttggatactg acaaacctac tatattagat | 1320 |
| ttcaacaaaa aggaagtcat tgattttgc aaattccagt atgaaaatgt aaagaaaata | 1380 |
| ctatccggag ataataatct agagcgtata ggatgttatt tagaagaata tggtgcaaat | 1440 |
| attgcatcat gttcaaagga tacatgggat cagattaacc agataggggaa gtcaaattac | 1500 |
| tgggcttgta ttaaagattt ttcagtcttg atgaaaaata tgttggcagt ttctcaatat | 1560 |
| aataggcaca atacttttcg tgtagtgtgt tgtgcaaaca ataatctgtt tgggttttgta | 1620 |
| atgccttctt ctgatattaa agcaaagcga tccacacttg tttacttctt agctgtgttg | 1680 |
| cattctactc ctcagaatgt gatgcaccac ggtgcattgc atgcgacatt taaaactggt | 1740 |
| tcaaaatacc ttagtatctc taaaggaatg cgtttagata agaacgatg tcaacgcata | 1800 |
| gttagttcac cgggacttttt tatgttgact acattgatgt ttgcaggaga caatccgaca | 1860 |
| ctcaatttga ctgatgtcat gaattttaca ttccacactt ccctgtctat aaccaaagct | 1920 |
| atgctgtcat tgacagaacc atcaagatat atgataatga attcattagc catatccagt | 1980 |
| catgttagag attatatagc agaaaaattt ggcccttata caaagaccag cttctctgta | 2040 |
| gtaatggcaa acttgattaa aggggatgt tatatggcat ataatcaaag agataaagta | 2100 |
| gacatgagga atatctgcct aacagattat gaaataactc aaaaggtgt gagagataac | 2160 |
| agagacctat catcaatctg gtttgaaggc tatgtatcac taaagaata tattaaccaa | 2220 |
| atatatctac cattttactt caattcaaaa ggtttgcatg aaaagcatca tgttatgata | 2280 |
| gatctggcta agacaatctt agatatagaa agggaccaga gattaaatat cccaggaata | 2340 |
| tggtctacaa cacctagaaa acaaactgca aatttaaata taactatcta tgcagttgca | 2400 |
| aaaaatctaa taatggacac tgctagacat aattatatta gatcacggat agaaaacaca | 2460 |
| aacaacttaa atagatcgat atgcactatt tctacattca ccagctctaa atcatgtatt | 2520 |
| aaagtaggcg acttttgagaa agaaaaaagc tcagcaacaa aaaaggctgc agattgcatg | 2580 |

```
tcaaaagaga taaagaagta tacaattgca aacccagaat ttgttgatga agagttacta    2640
aatgcaacta taagacattc acgctatgaa gacttaaaaa aagcaatccc gaattatatt    2700
gacattatgt caactaaagt atttgattct ctgtaccaga aaataaaaag gaaggagata    2760
gatgataaac ccactgtgta tcatatactc tctgctatga agaatcacac agattttaag    2820
tttacattct ttaacaaagg ccaaaaaaca gcaaaggata gggaaatatt cgtaggcgaa    2880
tttgaggcaa aaatgtgctt gtatttagtg gagaggatat ctaaagaacg ctgtaagttg    2940
aatccagatg agatgattag tgaaccaggc gattctaaat tgaaaaaatt agaagagctt    3000
gcagagtctg aaatacgatt cacagcagca actatgaaac agatcaaaga acgctatttta   3060
gcagaaatgg gagaagcaag ccatatgatc gcatataaac cacattctgt taagattgaa   3120
atcaatgcag acatgtcaaa atggagtgcc caagatgttt tattcaaata tttctggttg   3180
tttgcattag atcccgcact ttatctgcaa gaaaagaaa ggatattgta cttcctatgc     3240
aattatatgc aaaaaaagct aattctgcct gatgaaatgc tctgtagcat ccttgaccaa   3300
cgtatcaaac atgaggatga tataatatat gaaatgacca atggcttatc gcaaaattgg   3360
gtcaatatta aacggaactg gctgcagggg aatctcaatt acacaagtag ctacctacat   3420
tcatgttcta tgaatgttta taggatatt ctaaagagag cagccacttt actagaaggg    3480
gaagttttag tcaattctat ggttcattct gatgacaatc acacttcaat agtgatgatc   3540
caagataaat tagatgatga tattgttatt gaattttctg caaaactatt tgaaaaaata   3600
tgtctaactt ttggaaatca agcaaatatg aagaagacat atataacaaa tttcataaag   3660
gagttcgttt cactttttaa tatttatggt gagccatttt ctgtttatgg tcgctttatt   3720
ttgacatctg ttggcgattg tgcttttctt ggaccatatg aggatgttgc cagtaggttg   3780
tctgcaacgc agacagcaat taagcatgga gcacctccat cacttgcatg gactgctatt   3840
gcattaactc agtggataac acatagcaca tataacatgc ttccaggtca aatcaatgat   3900
cctacttcat ctttacctag tcatgataga tttgagctgc ctatagaatt gtgtggctta   3960
ataaattcag aattacccac tatagctata gcaggtttgg aagcagataa tctaagttat   4020
ttagttaggt tatcaaaaag aatgtcccct atacatcttt gccgtgaacc aatccagcat   4080
caatatgaga atatacatac atgggatata agtaaactga cacaatgtga tattttcaga   4140
cttaagcttt taagatacat gacgttagac tcaactatgt catctgatga tggaatgggc   4200
gaaactagtg aaatgagatc taggtctctt ctgacaccaa gaaaattcac tactgcaagt   4260
tcgttatcta gattgcattc atatgctgat tatcaaaaaa caatacaaga ccaacagaaa   4320
attgaagaat tatttgaata ttttatagcc aaccctcaac tattggttac aaaaggtgag   4380
acttgtgaag agttctgtat gtctgtattg ttcagataca acagtcgtaa atttaaagaa   4440
tcattgtcta ttcaaaaccc agctcagctc ttcatagaac aagtattgtt tgcaaataaa   4500
ccaatgatag actatacaag tattcatgat aggttgtttg gtatacaaga tgacccaaat   4560
ataaatgatg ctacatgtat tattggcaag aagacttttg ttgaaacata tcagcaaata   4620
aaaattgatg tagaaaaatt tacacttgat gtagaggata taaagacgat atatagcttc   4680
tgtataatga acgaccctat attagttgct tgtgcaaaca acttgttaat ttcaatacag   4740
ggagtgggaga tgcaacgatt gggtatgaca tgctgttata tgccggagat taagagcctt   4800
aaagtaattt atcatagtcc tgctctcgta ttacgtgctt atgtaacaga taactatgag   4860
caaaagggga tggagccaga tgaaatgcgg agagatatat atcatttaga agaatttata   4920
gagaagacaa aattgaggac aaatatgcaa gggagaattg caaataatga aattaagtta   4980
```

```
atgaagcgag atttgaaatt tgaagtgcag gaattgacta aattctatca gatctgttat   5040
gaatatgtga atcaacaga acacaaaatt aaaatattca tccttccaaa aaaggcttac    5100
actcccattg atttctgctc attagtaaca ggtaatctga tatcagacaa caaatggatg   5160
gttgttcact atttaaaaca aataactgtc ccagcaaaga aggcacaaat agccacatct   5220
atagatctgg aaatacaaat agcctacgaa tgtttcaggc taattgcaca ttttgctgat   5280
atgttcctaa atgatgactc caaaaaagct tatattaatg caattattaa cacatataca   5340
tacaaggatg ttcaagtatc cagtctctac aagaaaatca aaattcgag actacgttca    5400
aaaattatac cattattata tcacctgggc gatttgcaac aaatagacgt tgacagattt   5460
gatgcagaaa aagcagaaga gcagatcaca tggaataact ggcaaacatc tcgagaattt   5520
actactggtc caattgatct atcaatcaaa ggttatggac ggtcaataag gatcgtaggt   5580
gaggacaaca agcttacagc tgcagaaatg caattgtcaa gagtgagaag tgatatagta   5640
tcaaggcatg gacaggcttt attgaacaaa cctcatgggc taaaattaga gaaatggaa    5700
ccagtgactg atctaaatcc taaattatgg tatattgcat accaattgcg tgagaaaaag   5760
cggtatcact atggggtctt tagtacatct tatatagaag agcataactc aaggatagaa   5820
gcatctcgga tacgtaagac taataaatgg ataccagttt gccctattgc tatatcaaaa   5880
caatcatctg atggaaagcc tagtcttgca aaaatcccta tgttaaatat tggggagatt   5940
aaatttacaa aactacagat tgcagtagat gatcatgcaa tgattaggaa agccccattt   6000
agtaagatgg tgttctttga tggcccaccc atacagagcg gtggcattga cattggaaag   6060
cttatgaaga accaaaatat tctcaatttg aggttagata atatacagag tataacatta   6120
ttagatttgt gccgcatatt ttcatgccga gggtctaaag tggatcaaga tgcatttgaa   6180
ttcttatctg atgaaccttt ggatgaagat gttattgatg aattagatag ctcacctgca   6240
ttagtggtat cttacacaaa gaaatcaacc aaatccaata gtttcaaaaa tgttatagtt   6300
agagcattga taagagaatg tgatatattt gaagatataa tggacataac agacgatgga   6360
ttcacatctg atagcaatct agaggtgtta gaaaacttaa catggatttt aaatatgctc   6420
gcaacaaatc agtggtctac agaactgtta gcatgcatac acatgtgttt tatcgcaat    6480
gagatggatc atatctatca caattttcaa gttccagaaa tatttgtcga caatccaatc   6540
tcattaaatg taaagtggga tgaagtaatt atgttcttaa acatactgcg agacagagat   6600
tacaaatttg agccatgggt gtctatactg aatcattcct taactaaagc tatagagtat   6660
gcttacaaaa agatggaaga ggagaggaag cagaaatcaa caggcatcaa caattctta    6720
aagggtaaaa aaatgggtgg cagatcaaag tttgatttcc ag                      6762
```

<210> SEQ ID NO 15
<211> LENGTH: 2254
<212> TYPE: PRT
<213> ORGANISM: Artificial Sequence
<220> FEATURE:
<223> OTHER INFORMATION: Schmallenberg "L" ORF amino acid

<400> SEQUENCE: 15

Met Glu Thr Tyr Lys Ile Asn Ile Phe Arg Asp Arg Ile Asn Gln Cys
1               5                   10                  15

Arg Ser Ala Glu Glu Ala Lys Asp Ile Val Ala Asp Leu Leu Met Ala
            20                  25                  30

Arg His Asp Tyr Phe Gly Arg Glu Val Cys Tyr Tyr Leu Asp Ile Glu
        35                  40                  45

Phe Arg Gln Asp Val Pro Ala Tyr Asp Ile Leu Leu Glu Phe Leu Pro
    50                  55                  60

Ala Gly Thr Ala Phe Asn Ile Arg Asn Cys Thr Pro Asp Asn Phe Ile
65                  70                  75                  80

Ile His Asn Gly Lys Leu Tyr Ile Ile Asp Tyr Lys Val Ser Thr Asp
                    85                  90                  95

His Ala Tyr Gly Gln Lys Thr Tyr Glu Lys Tyr Thr Gln Ile Phe Gly
                100                 105                 110

Asp Ala Leu Ser Glu Leu Pro Phe Asp Phe Glu Val Val Ile Ile Arg
                115                 120                 125

Ala Asp Pro Leu Arg Asp Thr Ile His Val Asn Ser Asn Gln Phe Leu
        130                 135                 140

Glu Ile Phe Gly Pro Leu Asn Ile Asn Leu Asp Phe Thr Trp Phe Phe
145                 150                 155                 160

Asn Leu Arg Ser Leu Ile Tyr Glu Lys Tyr Lys Asp Asp Arg Phe
                165                 170                 175

Leu Glu Ile Val Asn Gln Gly Glu Phe Thr Met Thr Gly Pro Trp Ile
                180                 185                 190

Asp Glu Asp Thr Pro Glu Leu Tyr Ser His Pro Val Phe Leu Glu Phe
                195                 200                 205

Tyr Asp Ser Leu Asp Glu Met Ala Lys Leu Thr Phe His Glu Ser Met
        210                 215                 220

Thr Phe Asp Ala Thr Arg Gly Glu Lys Trp Asn Gln Asn Leu Gln Lys
225                 230                 235                 240

Val Ile Asn Arg Tyr Gly Asn Asp Tyr Asn Ile Phe Val Lys Glu Ala
                245                 250                 255

Ala Ala Gly Ile Phe Arg Cys Glu Gly Asn Tyr Pro Lys Pro Asn His
                260                 265                 270

Asp Glu Ile Thr Ile Gly Trp Asn Gln Met Val Gln Arg Val Ser Thr
        275                 280                 285

Glu Arg Asn Leu Thr Gln Asp Val Ser Lys Gln Lys Pro Ser Ile His
        290                 295                 300

Phe Ile Trp Gly Gln Pro Asp Glu Thr Ser Asn Ala Thr Thr Pro Lys
305                 310                 315                 320

Leu Ile Lys Ile Ala Lys Ala Leu Gln Asn Ile Ser Gly Glu Ser Thr
                325                 330                 335

Tyr Ile Ser Ala Phe Arg Ala Leu Gly Met Leu Met Asp Phe Ser Glu
                340                 345                 350

Asn Thr Ala Leu Tyr Glu Ala His Thr Ser Lys Leu Lys Ser Met Ala
        355                 360                 365

Arg Gln Thr Ser Lys Arg Ile Asp Thr Lys Leu Glu Pro Ile Lys Ile
        370                 375                 380

Gly Thr Ala Thr Ile Tyr Trp Glu Gln Gln Phe Lys Leu Asp Thr Glu
385                 390                 395                 400

Ile Met Asn Thr Lys Asp Lys Ser His Leu Leu Lys Asp Phe Leu Gly
                405                 410                 415

Ile Gly Gly His Val Gln Phe Ser Lys Lys Thr Ile Asp Asp Leu Asp
                420                 425                 430

Thr Asp Lys Pro Thr Ile Leu Asp Phe Asn Lys Lys Glu Val Ile Asp
        435                 440                 445

Phe Cys Lys Phe Gln Tyr Glu Asn Val Lys Lys Ile Leu Ser Gly Asp
450                 455                 460

-continued

```
Asn Asn Leu Glu Arg Ile Gly Cys Tyr Leu Glu Tyr Gly Ala Asn
465                 470                 475                 480

Ile Ala Ser Cys Ser Lys Asp Thr Trp Asp Gln Ile Asn Gln Ile Gly
                485                 490                 495

Lys Ser Asn Tyr Trp Ala Cys Ile Lys Asp Phe Ser Val Leu Met Lys
            500                 505                 510

Asn Met Leu Ala Val Ser Gln Tyr Asn Arg His Asn Thr Phe Arg Val
        515                 520                 525

Val Cys Cys Ala Asn Asn Leu Phe Gly Phe Val Met Pro Ser Ser
    530                 535                 540

Asp Ile Lys Ala Lys Arg Ser Thr Leu Val Tyr Phe Leu Ala Val Leu
545                 550                 555                 560

His Ser Thr Pro Gln Asn Val Met His Gly Ala Leu His Ala Thr
                565                 570                 575

Phe Lys Thr Gly Ser Lys Tyr Leu Ser Ile Ser Lys Gly Met Arg Leu
            580                 585                 590

Asp Lys Glu Arg Cys Gln Arg Ile Val Ser Ser Pro Gly Leu Phe Met
    595                 600                 605

Leu Thr Thr Leu Met Phe Ala Gly Asp Asn Pro Thr Leu Asn Leu Thr
610                 615                 620

Asp Val Met Asn Phe Thr Phe His Thr Ser Leu Ser Ile Thr Lys Ala
625                 630                 635                 640

Met Leu Ser Leu Thr Glu Pro Ser Arg Tyr Met Ile Met Asn Ser Leu
                645                 650                 655

Ala Ile Ser Ser His Val Arg Asp Tyr Ile Ala Glu Lys Phe Gly Pro
            660                 665                 670

Tyr Thr Lys Thr Ser Phe Ser Val Val Met Ala Asn Leu Ile Lys Arg
        675                 680                 685

Gly Cys Tyr Met Ala Tyr Asn Gln Arg Asp Lys Val Asp Met Arg Asn
    690                 695                 700

Ile Cys Leu Thr Asp Tyr Glu Ile Thr Gln Lys Gly Val Arg Asp Asn
705                 710                 715                 720

Arg Asp Leu Ser Ser Ile Trp Phe Glu Gly Tyr Val Ser Leu Lys Glu
                725                 730                 735

Tyr Ile Asn Gln Ile Tyr Leu Pro Phe Tyr Phe Asn Ser Lys Gly Leu
            740                 745                 750

His Glu Lys His His Val Met Ile Asp Leu Ala Lys Thr Ile Leu Asp
        755                 760                 765

Ile Glu Arg Asp Gln Arg Leu Asn Ile Pro Gly Ile Trp Ser Thr Thr
    770                 775                 780

Pro Arg Lys Gln Thr Ala Asn Leu Asn Ile Thr Ile Tyr Ala Val Ala
785                 790                 795                 800

Lys Asn Leu Ile Met Asp Thr Ala Arg His Asn Tyr Ile Arg Ser Arg
                805                 810                 815

Ile Glu Asn Thr Asn Asn Leu Asn Arg Ser Ile Cys Thr Ile Ser Thr
            820                 825                 830

Phe Thr Ser Ser Lys Ser Cys Ile Lys Val Gly Asp Phe Glu Lys Glu
        835                 840                 845

Lys Ser Ser Ala Thr Lys Lys Ala Ala Asp Cys Met Ser Lys Glu Ile
    850                 855                 860

Lys Lys Tyr Thr Ile Ala Asn Pro Glu Phe Val Asp Glu Glu Leu Leu
865                 870                 875                 880

Asn Ala Thr Ile Arg His Ser Arg Tyr Glu Asp Leu Lys Lys Ala Ile
```

-continued

```
              885                 890                 895
Pro Asn Tyr Ile Asp Ile Met Ser Thr Lys Val Phe Asp Ser Leu Tyr
              900                 905                 910

Gln Lys Ile Lys Arg Lys Glu Ile Asp Asp Lys Pro Thr Val Tyr His
              915                 920                 925

Ile Leu Ser Ala Met Lys Asn His Thr Asp Phe Lys Phe Thr Phe Phe
              930                 935                 940

Asn Lys Gly Gln Lys Thr Ala Lys Asp Arg Glu Ile Phe Val Gly Glu
945                 950                 955                 960

Phe Glu Ala Lys Met Cys Leu Tyr Leu Val Glu Arg Ile Ser Lys Glu
                  965                 970                 975

Arg Cys Lys Leu Asn Pro Asp Glu Met Ile Ser Glu Pro Gly Asp Ser
                  980                 985                 990

Lys Leu Lys Lys Leu Glu Glu Leu Ala Glu Ser Glu Ile Arg Phe Thr
                  995                 1000                1005

Ala Ala Thr Met Lys Gln Ile Lys Glu Arg Tyr Leu Ala Glu Met
         1010                1015                1020

Gly Glu Ala Ser His Met Ile Ala Tyr Lys Pro His Ser Val Lys
         1025                1030                1035

Ile Glu Ile Asn Ala Asp Met Ser Lys Trp Ser Ala Gln Asp Val
         1040                1045                1050

Leu Phe Lys Tyr Phe Trp Leu Phe Ala Leu Asp Pro Ala Leu Tyr
         1055                1060                1065

Leu Gln Glu Lys Glu Arg Ile Leu Tyr Phe Leu Cys Asn Tyr Met
         1070                1075                1080

Gln Lys Lys Leu Ile Leu Pro Asp Glu Met Leu Cys Ser Ile Leu
         1085                1090                1095

Asp Gln Arg Ile Lys His Glu Asp Ile Ile Tyr Glu Met Thr
         1100                1105                1110

Asn Gly Leu Ser Gln Asn Trp Val Asn Ile Lys Arg Asn Trp Leu
         1115                1120                1125

Gln Gly Asn Leu Asn Tyr Thr Ser Ser Tyr Leu His Ser Cys Ser
         1130                1135                1140

Met Asn Val Tyr Lys Asp Ile Leu Lys Arg Ala Ala Thr Leu Leu
         1145                1150                1155

Glu Gly Glu Val Leu Val Asn Ser Met Val His Ser Asp Asp Asn
         1160                1165                1170

His Thr Ser Ile Val Met Ile Gln Asp Lys Leu Asp Asp Ile
         1175                1180                1185

Val Ile Glu Phe Ser Ala Lys Leu Phe Glu Lys Ile Cys Leu Thr
         1190                1195                1200

Phe Gly Asn Gln Ala Asn Met Lys Lys Thr Tyr Ile Thr Asn Phe
         1205                1210                1215

Ile Lys Glu Phe Val Ser Leu Phe Asn Ile Tyr Gly Glu Pro Phe
         1220                1225                1230

Ser Val Tyr Gly Arg Phe Ile Leu Thr Ser Val Gly Asp Cys Ala
         1235                1240                1245

Phe Leu Gly Pro Tyr Glu Asp Val Ala Ser Arg Leu Ser Ala Thr
         1250                1255                1260

Gln Thr Ala Ile Lys His Gly Ala Pro Pro Ser Leu Ala Trp Thr
         1265                1270                1275

Ala Ile Ala Leu Thr Gln Trp Ile Thr His Ser Thr Tyr Asn Met
         1280                1285                1290
```

-continued

Leu Pro Gly Gln Ile Asn Asp Pro Thr Ser Ser Leu Pro Ser His
1295                1300                1305

Asp Arg Phe Glu Leu Pro Ile Glu Leu Cys Gly Leu Ile Asn Ser
1310                1315                1320

Glu Leu Pro Thr Ile Ala Ile Ala Gly Leu Glu Ala Asp Asn Leu
1325                1330                1335

Ser Tyr Leu Val Arg Leu Ser Lys Arg Met Ser Pro Ile His Leu
1340                1345                1350

Cys Arg Glu Pro Ile Gln His Gln Tyr Glu Asn Ile His Thr Trp
1355                1360                1365

Asp Ile Ser Lys Leu Thr Gln Cys Asp Ile Phe Arg Leu Lys Leu
1370                1375                1380

Leu Arg Tyr Met Thr Leu Asp Ser Thr Met Ser Ser Asp Asp Gly
1385                1390                1395

Met Gly Glu Thr Ser Glu Met Arg Ser Arg Ser Leu Leu Thr Pro
1400                1405                1410

Arg Lys Phe Thr Thr Ala Ser Ser Leu Ser Arg Leu His Ser Tyr
1415                1420                1425

Ala Asp Tyr Gln Lys Thr Ile Gln Asp Gln Gln Lys Ile Glu Glu
1430                1435                1440

Leu Phe Glu Tyr Phe Ile Ala Asn Pro Gln Leu Leu Val Thr Lys
1445                1450                1455

Gly Glu Thr Cys Glu Glu Phe Cys Met Ser Val Leu Phe Arg Tyr
1460                1465                1470

Asn Ser Arg Lys Phe Lys Glu Ser Leu Ser Ile Gln Asn Pro Ala
1475                1480                1485

Gln Leu Phe Ile Glu Gln Val Leu Phe Ala Asn Lys Pro Met Ile
1490                1495                1500

Asp Tyr Thr Ser Ile His Asp Arg Leu Phe Gly Ile Gln Asp Asp
1505                1510                1515

Pro Asn Ile Asn Asp Ala Thr Cys Ile Ile Gly Lys Lys Thr Phe
1520                1525                1530

Val Glu Thr Tyr Gln Gln Ile Lys Ile Asp Val Glu Lys Phe Thr
1535                1540                1545

Leu Asp Val Glu Asp Ile Lys Thr Ile Tyr Ser Phe Cys Ile Met
1550                1555                1560

Asn Asp Pro Ile Leu Val Ala Cys Ala Asn Asn Leu Leu Ile Ser
1565                1570                1575

Ile Gln Gly Val Glu Met Gln Arg Leu Gly Met Thr Cys Cys Tyr
1580                1585                1590

Met Pro Glu Ile Lys Ser Leu Lys Val Ile Tyr His Ser Pro Ala
1595                1600                1605

Leu Val Leu Arg Ala Tyr Val Thr Asp Asn Tyr Glu Gln Lys Gly
1610                1615                1620

Met Glu Pro Asp Glu Met Arg Arg Asp Ile Tyr His Leu Glu Glu
1625                1630                1635

Phe Ile Glu Lys Thr Lys Leu Arg Thr Asn Met Gln Gly Arg Ile
1640                1645                1650

Ala Asn Asn Glu Ile Lys Leu Met Lys Arg Asp Leu Lys Phe Glu
1655                1660                1665

Val Gln Glu Leu Thr Lys Phe Tyr Gln Ile Cys Tyr Glu Tyr Val
1670                1675                1680

```
Lys Ser Thr Glu His Lys Ile Lys Ile Phe Ile Leu Pro Lys Lys
    1685                1690                1695

Ala Tyr Thr Pro Ile Asp Phe Cys Ser Leu Val Thr Gly Asn Leu
    1700                1705                1710

Ile Ser Asp Asn Lys Trp Met Val Val His Tyr Leu Lys Gln Ile
    1715                1720                1725

Thr Val Pro Ala Lys Lys Ala Gln Ile Ala Thr Ser Ile Asp Leu
    1730                1735                1740

Glu Ile Gln Ile Ala Tyr Glu Cys Phe Arg Leu Ile Ala His Phe
    1745                1750                1755

Ala Asp Met Phe Leu Asn Asp Ser Lys Lys Ala Tyr Ile Asn
    1760                1765                1770

Ala Ile Ile Asn Thr Tyr Thr Tyr Lys Asp Val Gln Val Ser Ser
    1775                1780                1785

Leu Tyr Lys Lys Ile Lys Asn Ser Arg Leu Arg Ser Lys Ile Ile
    1790                1795                1800

Pro Leu Leu Tyr His Leu Gly Asp Leu Gln Gln Ile Asp Val Asp
    1805                1810                1815

Arg Phe Asp Ala Glu Lys Ala Glu Glu Gln Ile Thr Trp Asn Asn
    1820                1825                1830

Trp Gln Thr Ser Arg Glu Phe Thr Thr Gly Pro Ile Asp Leu Ser
    1835                1840                1845

Ile Lys Gly Tyr Gly Arg Ser Ile Arg Ile Val Gly Glu Asp Asn
    1850                1855                1860

Lys Leu Thr Ala Ala Glu Met Gln Leu Ser Arg Val Arg Ser Asp
    1865                1870                1875

Ile Val Ser Arg His Gly Gln Ala Leu Leu Asn Lys Pro His Gly
    1880                1885                1890

Leu Lys Leu Glu Lys Met Glu Pro Val Thr Asp Leu Asn Pro Lys
    1895                1900                1905

Leu Trp Tyr Ile Ala Tyr Gln Leu Arg Glu Lys Lys Arg Tyr His
    1910                1915                1920

Tyr Gly Val Phe Ser Thr Ser Tyr Ile Glu Glu His Asn Ser Arg
    1925                1930                1935

Ile Glu Ala Ser Arg Ile Arg Lys Thr Asn Lys Trp Ile Pro Val
    1940                1945                1950

Cys Pro Ile Ala Ile Ser Lys Gln Ser Ser Asp Gly Lys Pro Ser
    1955                1960                1965

Leu Ala Lys Ile Pro Met Leu Asn Ile Gly Glu Ile Lys Phe Thr
    1970                1975                1980

Lys Leu Gln Ile Ala Val Asp Asp His Ala Met Ile Arg Lys Ala
    1985                1990                1995

Pro Phe Ser Lys Met Val Phe Phe Asp Gly Pro Ile Gln Ser
    2000                2005                2010

Gly Gly Ile Asp Ile Gly Lys Leu Met Lys Asn Gln Asn Ile Leu
    2015                2020                2025

Asn Leu Arg Leu Asp Asn Ile Gln Ser Ile Thr Leu Leu Asp Leu
    2030                2035                2040

Cys Arg Ile Phe Ser Cys Arg Gly Ser Lys Val Asp Gln Asp Ala
    2045                2050                2055

Phe Glu Phe Leu Ser Asp Glu Pro Leu Asp Glu Asp Val Ile Asp
    2060                2065                2070

Glu Leu Asp Ser Ser Pro Ala Leu Val Val Ser Tyr Thr Lys Lys
```

-continued

```
    2075                2080                2085

Ser Thr  Lys Ser Asn Ser Phe  Lys Asn Val Ile Val  Arg Ala Leu
    2090                2095                2100

Ile Arg  Glu Cys Asp Ile Phe  Glu Asp Ile Met Asp  Ile Thr Asp
    2105                2110                2115

Asp Gly  Phe Thr Ser Asp Ser  Asn Leu Glu Val Leu  Glu Asn Leu
    2120                2125                2130

Thr Trp  Ile Leu Asn Met Leu  Ala Thr Asn Gln Trp  Ser Thr Glu
    2135                2140                2145

Leu Leu  Ala Cys Ile His Met  Cys Leu Tyr Arg Asn  Glu Met Asp
    2150                2155                2160

His Ile  Tyr His Asn Phe Gln  Val Pro Glu Ile Phe  Val Asp Asn
    2165                2170                2175

Pro Ile  Ser Leu Asn Val Lys  Trp Asp Glu Val Ile  Met Phe Leu
    2180                2185                2190

Asn Ile  Leu Arg Asp Arg Asp  Tyr Lys Phe Glu Pro  Trp Val Ser
    2195                2200                2205

Ile Leu  Asn His Ser Leu Thr  Lys Ala Ile Glu Tyr  Ala Tyr Lys
    2210                2215                2220

Lys Met  Glu Glu Glu Arg Lys  Gln Lys Ser Thr Gly  Ile Asn Lys
    2225                2230                2235

Phe Leu  Lys Gly Lys Lys Met  Gly Gly Arg Ser Lys  Phe Asp Phe
    2240                2245                2250

Gln

<210> SEQ ID NO 16
<211> LENGTH: 93
<212> TYPE: DNA
<213> ORGANISM: Artificial Sequence
<220> FEATURE:
<223> OTHER INFORMATION: Schmallenberg “L” 3'UTR

<400> SEQUENCE: 16
tagcttgatc ttaaataata cataatcttt gccccaaatc tgtattatat aaataattct     60
aaagtagttt catgtaatta ggggcacact act                                  93

<210> SEQ ID NO 17
<211> LENGTH: 6864
<212> TYPE: DNA
<213> ORGANISM: Artificial Sequence
<220> FEATURE:
<223> OTHER INFORMATION: Schmallenberg HE649912 nucleotide

<400> SEQUENCE: 17
ctaattacaa tcactatgga gacatacaag attaacattt ttagagatag gatcaaccag     60
tgtcgaagtg ctgaagaagc caaagacatt gttgctgatc ttctcatggc tagacatgac    120
tactttggta gagaggtatg ttattacctg gatatcgaat tccggcagga tgttccagct    180
tacgacatac ttcttgaatt tctgccagct ggcactgctt tcaacattcg caattgtaca    240
ccagacaatt ttatcattca caatggcaag ctttatatca ttgactataa agtatcaact    300
gatcatgcat atggtcaaaa aacttatgaa aagtacaccc agatctttgg agacgcattg    360
tcagaattgc cgtttgattt tgaagttgtg atcatccgtg ctgaccctct gcgagatact    420
atccatgtta attcaaatca attcttggaa atatttgggc cgctcaacat aaaccttgat    480
tttacttggt tctttaattt gcgatccctg atatatgaga aatataagga tgacgacaga    540
```

```
ttcctagaaa ttgtgaatca aggtgaattt acgatgactg gaccctggat tgatgaggat      600
accccggagc tctattcaca ccctgtcttt ttggaattct atgattcttt agatgagatg      660
gctaaactga cattccatga gtctatgaca tttgatgcaa ctcgcggtga gaaatggaat      720
caaaatctac aaaaggttat aaatagatat ggcaatgatt ataacatttt tgtgaaagag      780
gccgctgcag gaatctttag atgtgaaggg aactacccaa aaccaaatca tgatgaaatc      840
acaatcggtt ggaatcaaat ggttcaaaga gtgagtactg agagaaacct gactcaagat      900
gtcagcaagc aaaaaccatc tattcatttc atatggggtc aacctgacga acatcaaat       960 gcgacaacac caaaactaat caagattgca aaagcactcc aaaatatttc tggcgagtct     1020
acatatataa gcgcattcag agcattgggt atgcttatgg acttttctga gaacacagct     1080
ttatatgaag cacacactag caaactaaaa agtatggcaa gacagacatc gaaaagaatt     1140
gatactaaac tggaaccaat caaaataggc acggcgacaa tttattggga acagcagttt     1200
aaactggata ctgaaataat gaatacaaaa gacaaatcac atttgctaaa agattttctt     1260
ggcatagggg gtcacgtgca attttcaaaa aagaccattg acgatttgga tactgacaaa     1320
cctactatat tagatttcaa caaaaaggaa gtcattgatt tttgcaaatt ccagtatgaa     1380
aatgtaaaga aaatactatc cggagataat aatctagagc gtataggatg ttatttagaa     1440
gaatatggtg caaatattgc atcatgttca aaggatacat gggatcagat taaccagata     1500
gggaagtcaa attactgggc ttgtattaaa gattttcag tcttgatgaa aaatatgttg      1560
gcagtttctc aatataatag gcacaatact tttcgtgtag tgtgttgtgc aaacaataat     1620
ctgtttgggt ttgtaatgcc ttcttctgat attaaagcaa agcgatccac acttgtttac     1680
ttcttagctg tgttgcattc tactcctcag aatgtgatgc accacggtgc attgcatgcg     1740
acatttaaaa ctggttcaaa ataccttagt atctctaaag gaatgcgttt agataaagaa     1800
cgatgtcaac gcatagttag ttcaccggga ctttttatgt tgactacatt gatgtttgca     1860
ggagacaatc cgacactcaa tttgactgat gtcatgaatt ttacattcca cacttccctg     1920
tctataacca aagctatgct gtcattgaca gaaccatcaa gatatatgat aatgaattca     1980
ttagccatat ccagtcatgt tagagattat atagcagaaa aatttggccc ttatacaaag     2040
accagcttct ctgtagtaat ggcaaacttg attaaaaggg gatgttatat ggcatataat     2100
caaagagata agtagacat gaggaatatc tgcctaacag attatgaaat aactcaaaaa      2160
ggtgtgagag ataacagaga cctatcatca atctggtttg aaggctatgt atcactaaaa     2220
gaatatatta accaaatata tctaccattt tacttcaatt caaaaggttt gcatgaaaag     2280
catcatgtta tgatagatct ggctaagaca atcttagata tagaaaggga ccagagatta     2340
aatatcccag gaatatggtc tacaacacct agaaaacaaa ctgcaaattt aaatataact     2400
atctatgcag ttgcaaaaaa tctaataatg gacactgcta gacataatta tattagatca     2460
cggatagaaa acacaaacaa cttaaataga tcgatatgca ctatttctac attcaccagc     2520
tctaaatcat gtattaaagt aggcgacttt gagaaagaaa aaagctcagc aacaaaaaag     2580
gctgcagatt gcatgtcaaa agagataaag aagtatacaa ttgcaaaccc agaatttgtt     2640
gatgaagagt tactaaatgc aactataaga cattcacgct atgaagactt aaaaaaagca     2700
atcccgaatt atattgacat tatgtcaact aaagtatttg attctctgta ccagaaaata     2760
aaaaggaagg agatagatga taaacccact gtgtatcata tactctctgc tatgaagaat     2820
cacacagatt ttaagtttac attctttaac aaaggccaaa aaacagcaaa ggatagggaa     2880
atattcgtag gcgaatttga ggcaaaaatg tgcttgtatt tagtggagag gatatctaaa     2940
```

```
gaacgctgta agttgaatcc agatgagatg attagtgaac caggcgattc taaattgaaa    3000
aaattagaag agcttgcaga gtctgaaata cgattcacag cagcaactat gaaacagatc    3060
aaagaacgct atttagcaga aatgggagaa gcaagccata tgatcgcata taaaccacat    3120
tctgttaaga ttgaaatcaa tgcagacatg tcaaaatgga gtgcccaaga tgttttattc    3180
aaatatttct ggttgtttgc attagatccc gcactttatc tgcaagaaaa agaaaggata    3240
ttgtacttcc tatgcaatta tatgcaaaaa aagctaattc tgcctgatga aatgctctgt    3300
agcatccttg accaacgtat caaacatgag gatgatataa tatatgaaat gaccaatggc    3360
ttatcgcaaa attgggtcaa tattaaacgg aactggctgc aggggaatct caattacaca    3420
agtagctacc tacattcatg ttctatgaat gtttataagg atattctaaa gagagcagcc    3480
actttactag aagggaagt tttagtcaat tctatggttc attctgatga caatcacact    3540
tcaatagtga tgatccaaga taaattagat gatgatattg ttattgaatt ttctgcaaaa    3600
ctatttgaaa aaatatgtct aacttttgga aatcaagcaa atatgaagaa gacatatata    3660
acaaatttca taaaggagtt cgtttcactt tttaatattt atggtgagcc attttctgtt    3720
tatggtcgct ttattttgac atctgttggc gattgtgctt tcttggacc atatgaggat    3780 gttgccagta ggttgtctgc aacgcagaca gcaattaagc atggagcacc tccatcactt    3840
gcatggactg ctattgcatt aactcagtgg ataacacata gcacatataa catgcttcca    3900
ggtcaaatca atgatcctac ttcatctta cctagtcatg atagatttga gctgcctata    3960
gaattgtgtg gcttaataaa ttcagaatta cccactatag ctatagcagg tttggaagca    4020
gataatctaa gttatttagt taggttatca aaaagaatgt cccctataca tctttgccgt    4080
gaaccaatcc agcatcaata tgagaatata catacatggg atataagtaa actgacacaa    4140
tgtgatattt tcagacttaa gctttttaaga tacatgacgt tagactcaac tatgtcatct    4200
gatgatggaa tgggcgaaac tagtgaaatg agatctaggt ctcttctgac accaagaaaa    4260
ttcactactg caagttcgtt atctagattg cattcatatg ctgattatca aaaaacaata    4320
caagaccaac agaaaattga agaattattt gaatatttta tagccaaccc tcaactattg    4380
gttacaaaag gtgagacttg tgaagagttc tgtatgtctg tattgttcag atacaacagt    4440
cgtaaattta aagaatcatt gtctattcaa aacccagctc agctcttcat agaacaagta    4500
ttgtttgcaa ataaaccaat gatagactat acaagtattc atgataggtt gtttggtata    4560
caagatgacc caaatataaa tgatgctaca tgtattattg gcaagaagac ttttgttgaa    4620
acatatcagc aaataaaaat tgatgtagaa aaatttacac ttgatgtaga ggatataaag    4680
acgatatata gcttctgtat aatgaacgac cctatattag ttgcttgtgc aaacaacttg    4740
ttaatttcaa tacagggagt ggagatgcaa cgattgggta tgacatgctg ttatatgccg    4800
gagattaaga gccttaaagt aatttatcat agtcctgctc tcgtattacg tgcttatgta    4860
acagataact atgagcaaaa agggatggag ccagatgaaa tgcggagaga tatatatcat    4920
ttagaagaat ttatagagaa gacaaaattg aggacaaata tgcaagggag aattgcaaat    4980
aatgaaatta agttaatgaa gcgagatttg aaatttgaag tgcaggaatt gactaaattc    5040
tatcagatct gttatgaata tgtgaaatca acagaacaca aaattaaaat attcatcctt    5100
ccaaaaaagg cttacactcc cattgatttc tgctcattag taacaggtaa tctgatatca    5160
gacaacaaat ggatggttgt tcactatta aaacaaataa ctgtcccagc aaagaaggca    5220
caaatagcca catctataga tctggaaata caaatagcct acgaatgttt caggctaatt    5280
```

-continued

```
gcacattttg ctgatatgtt cctaaatgat gactccaaaa aagcttatat taatgcaatt    5340
attaacacat atacatacaa ggatgttcaa gtatccagtc tctacaagaa aatcaaaaat    5400
tcgagactac gttcaaaaat tataccatta ttatatcacc tgggcgattt gcaacaaata    5460
gacgttgaca gatttgatgc agaaaaagca gaagagcaga tcacatggaa taactggcaa    5520
acatctcgag aatttactac tggtccaatt gatctatcaa tcaaggttta tggacggtca    5580
ataaggatcg taggtgagga caacaagctt acagctgcag aaatgcaatt gtcaagagtg    5640
agaagtgata tagtatcaag gcatggacag gctttattga caaacctca tgggctaaaa     5700
ttagagaaaa tggaaccagt gactgatcta atcctaaat tatggtatat tgcataccaa     5760
ttgcgtgaga aaaagcggta tcactatggg gtctttagta catcttatat agaagagcat    5820
aactcaagga tagaagcatc tcggatacgt aagactaata aatggatacc agtttgccct    5880
attgctatat caaacaatc atctgatgga aagcctagtc ttgcaaaaat ccctatgtta    5940
aatattgggg agattaaatt tacaaaacta cagattgcag tagatgatca tgcaatgatt    6000
aggaaagccc catttagtaa gatggtgttc tttgatggcc cacccataca gagcggtggc    6060
attgacattg gaaagcttat gaagaaccaa aatattctca atttgaggtt agataatata    6120
cagagtataa cattattaga tttgtgccgc atattttcat gccgagggtc taaagtggat    6180
caagatgcat ttgaattctt atctgatgaa cctttggatg aagatgttat tgatgaatta    6240
gatagctcac ctgcattagt ggtatcttac acaaagaaat caaccaaatc caatagtttc    6300
aaaaatgtta tagttagagc attgataaga gaatgtgata tatttgaaga tataatggac    6360
ataacagacg atggattcac atctgatagc aatctagagg tgttagaaaa cttaacatgg    6420
attttaaata tgctcgcaac aaatcagtgg tctacagaac tgttagcatg catacacatg    6480
tgtttatatc gcaatgagat ggatcatatc tatcacaatt ttcaagttcc agaaatatttt    6540
gtcgacaatc caatctcatt aaatgtaaag tgggatgaag taattatgtt cttaaacata    6600
ctgcgagaca gagattacaa atttgagcca tgggtgtcta tactgaatca ttccttaact    6660
aaagctatag agtatgctta caaaaagatg gaagaggaga ggaagcagaa atcaacaggc    6720
atcaacaaat tcttaaaggg taaaaaaatg ggtggcagat caaagtttga tttccagtag    6780
cttgatctta ataatacat aatctttgcc ccaaatctgt attatataaa taattctaaa     6840
gtagtttcat gtaattaggg gcac                                           6864
```

<210> SEQ ID NO 18
<211> LENGTH: 2254
<212> TYPE: PRT
<213> ORGANISM: Artificial Sequence
<220> FEATURE:
<223> OTHER INFORMATION: Schmallenberg HE649912 amino acid

<400> SEQUENCE: 18

```
Met Glu Thr Tyr Lys Ile Asn Ile Phe Arg Asp Arg Ile Asn Gln Cys
1               5                   10                  15

Arg Ser Ala Glu Glu Ala Lys Asp Ile Val Ala Asp Leu Leu Met Ala
            20                  25                  30

Arg His Asp Tyr Phe Gly Arg Glu Val Cys Tyr Tyr Leu Asp Ile Glu
        35                  40                  45

Phe Arg Gln Asp Val Pro Ala Tyr Asp Ile Leu Leu Glu Phe Leu Pro
    50                  55                  60

Ala Gly Thr Ala Phe Asn Ile Arg Asn Cys Thr Pro Asp Asn Phe Ile
65                  70                  75                  80
```

```
Ile His Asn Gly Lys Leu Tyr Ile Ile Asp Tyr Lys Val Ser Thr Asp
                85                  90                  95
His Ala Tyr Gly Gln Lys Thr Tyr Glu Lys Tyr Thr Gln Ile Phe Gly
            100                 105                 110
Asp Ala Leu Ser Glu Leu Pro Phe Asp Phe Glu Val Val Ile Ile Arg
            115                 120                 125
Ala Asp Pro Leu Arg Asp Thr Ile His Val Asn Ser Asn Gln Phe Leu
        130                 135                 140
Glu Ile Phe Gly Pro Leu Asn Ile Asn Leu Asp Phe Thr Trp Phe Phe
145                 150                 155                 160
Asn Leu Arg Ser Leu Ile Tyr Glu Lys Tyr Lys Asp Asp Asp Arg Phe
                165                 170                 175
Leu Glu Ile Val Asn Gln Gly Glu Phe Thr Met Thr Gly Pro Trp Ile
            180                 185                 190
Asp Glu Asp Thr Pro Glu Leu Tyr Ser His Pro Val Phe Leu Glu Phe
        195                 200                 205
Tyr Asp Ser Leu Asp Glu Met Ala Lys Leu Thr Phe His Glu Ser Met
    210                 215                 220
Thr Phe Asp Ala Thr Arg Gly Glu Lys Trp Asn Gln Asn Leu Gln Lys
225                 230                 235                 240
Val Ile Asn Arg Tyr Gly Asn Asp Tyr Asn Ile Phe Val Lys Glu Ala
                245                 250                 255
Ala Ala Gly Ile Phe Arg Cys Glu Gly Asn Tyr Pro Lys Pro Asn His
            260                 265                 270
Asp Glu Ile Thr Ile Gly Trp Asn Gln Met Val Gln Arg Val Ser Thr
        275                 280                 285
Glu Arg Asn Leu Thr Gln Asp Val Ser Lys Gln Lys Pro Ser Ile His
    290                 295                 300
Phe Ile Trp Gly Gln Pro Asp Glu Thr Ser Asn Ala Thr Thr Pro Lys
305                 310                 315                 320
Leu Ile Lys Ile Ala Lys Ala Leu Gln Asn Ile Ser Gly Glu Ser Thr
                325                 330                 335
Tyr Ile Ser Ala Phe Arg Ala Leu Gly Met Leu Met Asp Phe Ser Glu
            340                 345                 350
Asn Thr Ala Leu Tyr Glu Ala His Thr Ser Lys Leu Lys Ser Met Ala
        355                 360                 365
Arg Gln Thr Ser Lys Arg Ile Asp Thr Lys Leu Glu Pro Ile Lys Ile
    370                 375                 380
Gly Thr Ala Thr Ile Tyr Trp Glu Gln Gln Phe Lys Leu Asp Thr Glu
385                 390                 395                 400
Ile Met Asn Thr Lys Asp Lys Ser His Leu Leu Lys Asp Phe Leu Gly
                405                 410                 415
Ile Gly Gly His Val Gln Phe Ser Lys Lys Thr Ile Asp Asp Leu Asp
            420                 425                 430
Thr Asp Lys Pro Thr Ile Leu Asp Phe Asn Lys Lys Glu Val Ile Asp
        435                 440                 445
Phe Cys Lys Phe Gln Tyr Glu Asn Val Lys Lys Ile Leu Ser Gly Asp
    450                 455                 460
Asn Asn Leu Glu Arg Ile Gly Cys Tyr Leu Glu Tyr Gly Ala Asn
465                 470                 475                 480
Ile Ala Ser Cys Ser Lys Asp Thr Trp Asp Gln Ile Asn Gln Ile Gly
                485                 490                 495
Lys Ser Asn Tyr Trp Ala Cys Ile Lys Asp Phe Ser Val Leu Met Lys
```

```
                500             505             510
Asn Met Leu Ala Val Ser Gln Tyr Asn Arg His Asn Thr Phe Arg Val
            515             520             525

Val Cys Cys Ala Asn Asn Leu Phe Gly Phe Val Met Pro Ser Ser
        530             535             540

Asp Ile Lys Ala Lys Arg Ser Thr Leu Val Tyr Phe Leu Ala Val Leu
545             550             555             560

His Ser Thr Pro Gln Asn Val Met His Gly Ala Leu His Ala Thr
            565             570             575

Phe Lys Thr Gly Ser Lys Tyr Leu Ser Ile Ser Lys Gly Met Arg Leu
            580             585             590

Asp Lys Glu Arg Cys Gln Arg Ile Val Ser Ser Pro Gly Leu Phe Met
            595             600             605

Leu Thr Thr Leu Met Phe Ala Gly Asp Asn Pro Thr Leu Asn Leu Thr
            610             615             620

Asp Val Met Asn Phe Thr Phe His Thr Ser Leu Ser Ile Thr Lys Ala
625             630             635             640

Met Leu Ser Leu Thr Glu Pro Ser Arg Tyr Met Ile Met Asn Ser Leu
            645             650             655

Ala Ile Ser Ser His Val Arg Asp Tyr Ile Ala Glu Lys Phe Gly Pro
            660             665             670

Tyr Thr Lys Thr Ser Phe Ser Val Val Met Ala Asn Leu Ile Lys Arg
            675             680             685

Gly Cys Tyr Met Ala Tyr Asn Gln Arg Asp Lys Val Asp Met Arg Asn
            690             695             700

Ile Cys Leu Thr Asp Tyr Glu Ile Thr Gln Lys Gly Val Arg Asp Asn
705             710             715             720

Arg Asp Leu Ser Ser Ile Trp Phe Glu Gly Tyr Val Ser Leu Lys Glu
            725             730             735

Tyr Ile Asn Gln Ile Tyr Leu Pro Phe Tyr Phe Asn Ser Lys Gly Leu
            740             745             750

His Glu Lys His His Val Met Ile Asp Leu Ala Lys Thr Ile Leu Asp
            755             760             765

Ile Glu Arg Asp Gln Arg Leu Asn Ile Pro Gly Ile Trp Ser Thr Thr
            770             775             780

Pro Arg Lys Gln Thr Ala Asn Leu Asn Ile Thr Ile Tyr Ala Val Ala
785             790             795             800

Lys Asn Leu Ile Met Asp Thr Ala Arg His Asn Tyr Ile Arg Ser Arg
            805             810             815

Ile Glu Asn Thr Asn Asn Leu Asn Arg Ser Ile Cys Thr Ile Ser Thr
            820             825             830

Phe Thr Ser Ser Lys Ser Cys Ile Lys Val Gly Asp Phe Glu Lys Glu
            835             840             845

Lys Ser Ser Ala Thr Lys Lys Ala Ala Asp Cys Met Ser Lys Glu Ile
            850             855             860

Lys Lys Tyr Thr Ile Ala Asn Pro Glu Phe Val Asp Glu Leu Leu
865             870             875             880

Asn Ala Thr Ile Arg His Ser Arg Tyr Glu Asp Leu Lys Lys Ala Ile
            885             890             895

Pro Asn Tyr Ile Asp Ile Met Ser Thr Lys Val Phe Asp Ser Leu Tyr
            900             905             910

Gln Lys Ile Lys Arg Lys Glu Ile Asp Asp Lys Pro Thr Val Tyr His
            915             920             925
```

```
Ile Leu Ser Ala Met Lys Asn His Thr Asp Phe Lys Phe Thr Phe Phe
    930                 935                 940

Asn Lys Gly Gln Lys Thr Ala Lys Asp Arg Glu Ile Phe Val Gly Glu
945                 950                 955                 960

Phe Glu Ala Lys Met Cys Leu Tyr Leu Val Glu Arg Ile Ser Lys Glu
                965                 970                 975

Arg Cys Lys Leu Asn Pro Asp Glu Met Ile Ser Glu Pro Gly Asp Ser
            980                 985                 990

Lys Leu Lys Lys Leu Glu Glu Leu Ala Glu Ser Glu Ile Arg Phe Thr
        995                 1000                1005

Ala Ala Thr Met Lys Gln Ile Lys Glu Arg Tyr Leu Ala Glu Met
    1010                1015                1020

Gly Glu Ala Ser His Met Ile Ala Tyr Lys Pro His Ser Val Lys
    1025                1030                1035

Ile Glu Ile Asn Ala Asp Met Ser Lys Trp Ser Ala Gln Asp Val
    1040                1045                1050

Leu Phe Lys Tyr Phe Trp Leu Phe Ala Leu Asp Pro Ala Leu Tyr
    1055                1060                1065

Leu Gln Glu Lys Glu Arg Ile Leu Tyr Phe Leu Cys Asn Tyr Met
    1070                1075                1080

Gln Lys Lys Leu Ile Leu Pro Asp Glu Met Leu Cys Ser Ile Leu
    1085                1090                1095

Asp Gln Arg Ile Lys His Glu Asp Ile Ile Tyr Glu Met Thr
    1100                1105                1110

Asn Gly Leu Ser Gln Asn Trp Val Asn Ile Lys Arg Asn Trp Leu
    1115                1120                1125

Gln Gly Asn Leu Asn Tyr Thr Ser Ser Tyr Leu His Ser Cys Ser
    1130                1135                1140

Met Asn Val Tyr Lys Asp Ile Leu Lys Arg Ala Ala Thr Leu Leu
    1145                1150                1155

Glu Gly Glu Val Leu Val Asn Ser Met Val His Ser Asp Asp Asn
    1160                1165                1170

His Thr Ser Ile Val Met Ile Gln Asp Lys Leu Asp Asp Ile
    1175                1180                1185

Val Ile Glu Phe Ser Ala Lys Leu Phe Glu Lys Ile Cys Leu Thr
    1190                1195                1200

Phe Gly Asn Gln Ala Asn Met Lys Lys Thr Tyr Ile Thr Asn Phe
    1205                1210                1215

Ile Lys Glu Phe Val Ser Leu Phe Asn Ile Tyr Gly Glu Pro Phe
    1220                1225                1230

Ser Val Tyr Gly Arg Phe Ile Leu Thr Ser Val Gly Asp Cys Ala
    1235                1240                1245

Phe Leu Gly Pro Tyr Glu Asp Val Ala Ser Arg Leu Ser Ala Thr
    1250                1255                1260

Gln Thr Ala Ile Lys His Gly Ala Pro Pro Ser Leu Ala Trp Thr
    1265                1270                1275

Ala Ile Ala Leu Thr Gln Trp Ile Thr His Ser Thr Tyr Asn Met
    1280                1285                1290

Leu Pro Gly Gln Ile Asn Asp Pro Thr Ser Ser Leu Pro Ser His
    1295                1300                1305

Asp Arg Phe Glu Leu Pro Ile Glu Leu Cys Gly Leu Ile Asn Ser
    1310                1315                1320
```

```
Glu  Leu  Pro  Thr  Ile  Ala  Ile  Ala  Gly  Leu  Glu  Ala  Asp  Asn  Leu
     1325                1330                1335

Ser  Tyr  Leu  Val  Arg  Leu  Ser  Lys  Arg  Met  Ser  Pro  Ile  His  Leu
     1340                1345                1350

Cys  Arg  Glu  Pro  Ile  Gln  His  Gln  Tyr  Glu  Asn  Ile  His  Thr  Trp
     1355                1360                1365

Asp  Ile  Ser  Lys  Leu  Thr  Gln  Cys  Asp  Ile  Phe  Arg  Leu  Lys  Leu
     1370                1375                1380

Leu  Arg  Tyr  Met  Thr  Leu  Asp  Ser  Thr  Met  Ser  Ser  Asp  Asp  Gly
     1385                1390                1395

Met  Gly  Glu  Thr  Ser  Glu  Met  Arg  Ser  Arg  Ser  Leu  Leu  Thr  Pro
     1400                1405                1410

Arg  Lys  Phe  Thr  Thr  Ala  Ser  Ser  Leu  Ser  Arg  Leu  His  Ser  Tyr
     1415                1420                1425

Ala  Asp  Tyr  Gln  Lys  Thr  Ile  Gln  Asp  Gln  Gln  Lys  Ile  Glu  Glu
     1430                1435                1440

Leu  Phe  Glu  Tyr  Phe  Ile  Ala  Asn  Pro  Gln  Leu  Leu  Val  Thr  Lys
     1445                1450                1455

Gly  Glu  Thr  Cys  Glu  Glu  Phe  Cys  Met  Ser  Val  Leu  Phe  Arg  Tyr
     1460                1465                1470

Asn  Ser  Arg  Lys  Phe  Lys  Glu  Ser  Leu  Ser  Ile  Gln  Asn  Pro  Ala
     1475                1480                1485

Gln  Leu  Phe  Ile  Glu  Gln  Val  Leu  Phe  Ala  Asn  Lys  Pro  Met  Ile
     1490                1495                1500

Asp  Tyr  Thr  Ser  Ile  His  Asp  Arg  Leu  Phe  Gly  Ile  Gln  Asp  Asp
     1505                1510                1515

Pro  Asn  Ile  Asn  Asp  Ala  Thr  Cys  Ile  Ile  Gly  Lys  Lys  Thr  Phe
     1520                1525                1530

Val  Glu  Thr  Tyr  Gln  Gln  Ile  Lys  Ile  Asp  Val  Glu  Lys  Phe  Thr
     1535                1540                1545

Leu  Asp  Val  Glu  Asp  Ile  Lys  Thr  Ile  Tyr  Ser  Phe  Cys  Ile  Met
     1550                1555                1560

Asn  Asp  Pro  Ile  Leu  Val  Ala  Cys  Ala  Asn  Asn  Leu  Leu  Ile  Ser
     1565                1570                1575

Ile  Gln  Gly  Val  Glu  Met  Gln  Arg  Leu  Gly  Met  Thr  Cys  Cys  Tyr
     1580                1585                1590

Met  Pro  Glu  Ile  Lys  Ser  Leu  Lys  Val  Ile  Tyr  His  Ser  Pro  Ala
     1595                1600                1605

Leu  Val  Leu  Arg  Ala  Tyr  Val  Thr  Asp  Asn  Tyr  Glu  Gln  Lys  Gly
     1610                1615                1620

Met  Glu  Pro  Asp  Glu  Met  Arg  Arg  Asp  Ile  Tyr  His  Leu  Glu  Glu
     1625                1630                1635

Phe  Ile  Glu  Lys  Thr  Lys  Leu  Arg  Thr  Asn  Met  Gln  Gly  Arg  Ile
     1640                1645                1650

Ala  Asn  Asn  Glu  Ile  Lys  Leu  Met  Lys  Arg  Asp  Leu  Lys  Phe  Glu
     1655                1660                1665

Val  Gln  Glu  Leu  Thr  Lys  Phe  Tyr  Gln  Ile  Cys  Tyr  Glu  Tyr  Val
     1670                1675                1680

Lys  Ser  Thr  Glu  His  Lys  Ile  Lys  Ile  Phe  Ile  Leu  Pro  Lys  Lys
     1685                1690                1695

Ala  Tyr  Thr  Pro  Ile  Asp  Phe  Cys  Ser  Leu  Val  Thr  Gly  Asn  Leu
     1700                1705                1710

Ile  Ser  Asp  Asn  Lys  Trp  Met  Val  Val  His  Tyr  Leu  Lys  Gln  Ile
```

-continued

```
                1715                1720                1725
Thr Val Pro Ala Lys Lys Ala Gln Ile Ala Thr Ser Ile Asp Leu
        1730                1735                1740
Glu Ile Gln Ile Ala Tyr Glu Cys Phe Arg Leu Ile Ala His Phe
        1745                1750                1755
Ala Asp Met Phe Leu Asn Asp Ser Lys Lys Ala Tyr Ile Asn
        1760                1765                1770
Ala Ile Ile Asn Thr Tyr Thr Tyr Lys Asp Val Gln Val Ser Ser
        1775                1780                1785
Leu Tyr Lys Lys Ile Lys Asn Ser Arg Leu Arg Ser Lys Ile Ile
        1790                1795                1800
Pro Leu Leu Tyr His Leu Gly Asp Leu Gln Gln Ile Asp Val Asp
        1805                1810                1815
Arg Phe Asp Ala Glu Lys Ala Glu Glu Gln Ile Thr Trp Asn Asn
        1820                1825                1830
Trp Gln Thr Ser Arg Glu Phe Thr Thr Gly Pro Ile Asp Leu Ser
        1835                1840                1845
Ile Lys Gly Tyr Gly Arg Ser Ile Arg Ile Val Gly Glu Asp Asn
        1850                1855                1860
Lys Leu Thr Ala Ala Glu Met Gln Leu Ser Arg Val Arg Ser Asp
        1865                1870                1875
Ile Val Ser Arg His Gly Gln Ala Leu Leu Asn Lys Pro His Gly
        1880                1885                1890
Leu Lys Leu Glu Lys Met Glu Pro Val Thr Asp Leu Asn Pro Lys
        1895                1900                1905
Leu Trp Tyr Ile Ala Tyr Gln Leu Arg Glu Lys Lys Arg Tyr His
        1910                1915                1920
Tyr Gly Val Phe Ser Thr Ser Tyr Ile Glu Glu His Asn Ser Arg
        1925                1930                1935
Ile Glu Ala Ser Arg Ile Arg Lys Thr Asn Lys Trp Ile Pro Val
        1940                1945                1950
Cys Pro Ile Ala Ile Ser Lys Gln Ser Ser Asp Gly Lys Pro Ser
        1955                1960                1965
Leu Ala Lys Ile Pro Met Leu Asn Ile Gly Glu Ile Lys Phe Thr
        1970                1975                1980
Lys Leu Gln Ile Ala Val Asp Asp His Ala Met Ile Arg Lys Ala
        1985                1990                1995
Pro Phe Ser Lys Met Val Phe Phe Asp Gly Pro Ile Gln Ser
        2000                2005                2010
Gly Gly Ile Asp Ile Gly Lys Leu Met Lys Asn Gln Asn Ile Leu
        2015                2020                2025
Asn Leu Arg Leu Asp Asn Ile Gln Ser Ile Thr Leu Leu Asp Leu
        2030                2035                2040
Cys Arg Ile Phe Ser Cys Arg Gly Ser Lys Val Asp Gln Asp Ala
        2045                2050                2055
Phe Glu Phe Leu Ser Asp Glu Pro Leu Asp Glu Asp Val Ile Asp
        2060                2065                2070
Glu Leu Asp Ser Ser Pro Ala Leu Val Val Ser Tyr Thr Lys Lys
        2075                2080                2085
Ser Thr Lys Ser Asn Ser Phe Lys Asn Val Ile Val Arg Ala Leu
        2090                2095                2100
Ile Arg Glu Cys Asp Ile Phe Glu Asp Ile Met Asp Ile Thr Asp
        2105                2110                2115
```

```
Asp Gly Phe Thr Ser Asp Ser  Asn Leu Glu Val Leu  Glu Asn Leu
    2120            2125                 2130

Thr Trp Ile Leu Asn Met Leu  Ala Thr Asn Gln Trp  Ser Thr Glu
    2135            2140                 2145

Leu Leu Ala Cys Ile His Met  Cys Leu Tyr Arg Asn  Glu Met Asp
    2150            2155                 2160

His Ile Tyr His Asn Phe Gln  Val Pro Glu Ile Phe  Val Asp Asn
    2165            2170                 2175

Pro Ile Ser Leu Asn Val Lys  Trp Asp Glu Val Ile  Met Phe Leu
    2180            2185                 2190

Asn Ile Leu Arg Asp Arg Asp  Tyr Lys Phe Glu Pro  Trp Val Ser
    2195            2200                 2205

Ile Leu Asn His Ser Leu Thr  Lys Ala Ile Glu Tyr  Ala Tyr Lys
    2210            2215                 2220

Lys Met Glu Glu Glu Arg Lys  Gln Lys Ser Thr Gly  Ile Asn Lys
    2225            2230                 2235

Phe Leu Lys Gly Lys Lys Met  Gly Gly Arg Ser Lys  Phe Asp Phe
    2240            2245                 2250

Gln
```

REVERSE GENETICS SCHMALLENBERG VIRUS VACCINE COMPOSITIONS, AND METHODS OF USE THEREOF

INCORPORATION BY REFERENCE

This application claims priority to provisional application U.S. Ser. No. 61/776,833, filed on Mar. 12, 2013, which is incorporated by reference herein in its entirety. All documents cited or referenced herein, and all documents cited or referenced therein, are hereby incorporated herein by reference, and may be employed in the practice of the invention.

FIELD OF THE INVENTION

The present disclosure relates to Schmallenberg viruses (SBV), sequences and vaccine compositions. The disclosure further relates to a reverse genetics system for the production of live attenuated vaccines. It also relates to polynucleotides which can be used for the production of subunits in an in vitro expression system or integrated into an appropriate vehicle for in vivo expression. Moreover, the present disclosure relates to unmodified and modified SBV, to methods of making and using the same, and to certain DNA and protein sequences.

BACKGROUND

Schmallenberg virus (SBV) belongs to the *Orthobunyavirus* genus of the Bunyaviridae family. SBV was initially reported in 2001 to cause congenital malformations and stillbirths in cattle, sheep, goats, and possibly alpaca, and is apparently transmitted by midges (*Culicoides* spp.). The SBV genome comprises three segments: small (S), medium (M) and large (L). The S segment encodes the nucleocapsid (N) protein and a non-structural protein (NSs). The M genome segment encodes a non-structural protein (NSm) and two structural glycoproteins (Gn and Gc). The L segment encodes the viral polymerase (FIG. 1). Prior to the instant disclosure, the only published SBV sequence was by Hoffmann et al. (GenBank HE649912-14, herein the "FLI sequence;" Hoffmann et al., E.I.D. 18(3), 2012). It is important to note, however, that the FLI sequence was not obtained from a single virus isolate and sequence gaps were filled by sequencing of cell culture-passaged virus. Furthermore, although Hoffmann et al. claimed that the published sequences correspond to the full-length genome segments, the absence of "panhandle" sequences on the 3' and 5' terminal ends of the sequences made clear that the sequences were not complete. Therefore, one goal of the instant disclosure is to present a full SBV genome sequence.

SUMMARY OF THE INVENTION

The invention is based on Schmallenberg virus (SBV) vaccine compositions produced using a reverse genetics approach. Plasmids encoding the SBV S, M, and L segments were produced and co-transfected into permissive cells for production of recombinant SBV. The SBV sequence and reverse genetic system described herein may be used to produce effective, immunological and vaccine compositions. Moreover, the system naturally lends itself to the engineering of viral vaccines having little or no virulence, as compared to the wildtype SBV, thereby paving the way for safety of the host animal.

One aspect of the disclosure relates to SBV, DNA and protein sequences involved in making modified or recombinant virus. One embodiment of the invention relates to the genomic and protein sequences of SBV.

Another aspect of the disclosure relates to SBV, which have enhanced safety, strong humoral immune responses. The disclosure thus encompasses methods of making such recombinant viruses.

Another aspect of the disclosure relates to SBV vaccines or compositions having an increased level of safety compared to known SBV or other recombinant vaccines.

Another aspect of the disclosure relates to an SBV vector which provides a reverse genetics system, wherein the vector can be used as a backbone for recombinant vaccines or compositions in different host animals.

In yet another aspect, the present disclosure relates to a pharmaceutical composition or vaccine for inducing an immunological response in a host animal inoculated with the composition or vaccine, the composition or vaccine including a pharmaceutical acceptable carrier and an SB virus or viral vector. In yet another aspect of the disclosure, the SB virus or viral vector includes, within a non-essential region of the virus genome, a heterologous DNA which encodes an antigenic protein derived from a pathogen wherein the composition or vaccine when administered to a host, is capable of inducing an immunological response specific to the protein encoded by the pathogen.

These and other embodiments are disclosed or are obvious from and encompassed by, the following Detailed Description.

BRIEF DESCRIPTION OF DRAWINGS

A full and enabling disclosure of the present invention, including the best mode thereof, to one of ordinary skill in the art, is set forth more particularly in the remainder of the specification, including reference to the accompanying figures, wherein:

FIG. 3 presents the SBV S segment and RevGen construct features;

FIG. 4 presents the SBV M segment and RevGen construct features;

FIG. 5 presents the SBV L segment and RevGen construct features;

FIG. 6 presents the published HE649912 sequence as set forth in SEQ ID NO: 17;

FIG. 7 presents the HE649912 amino acid sequence, as set forth in SEQ ID NO: 18.

DETAILED DESCRIPTION OF THE INVENTION

Figure 1:
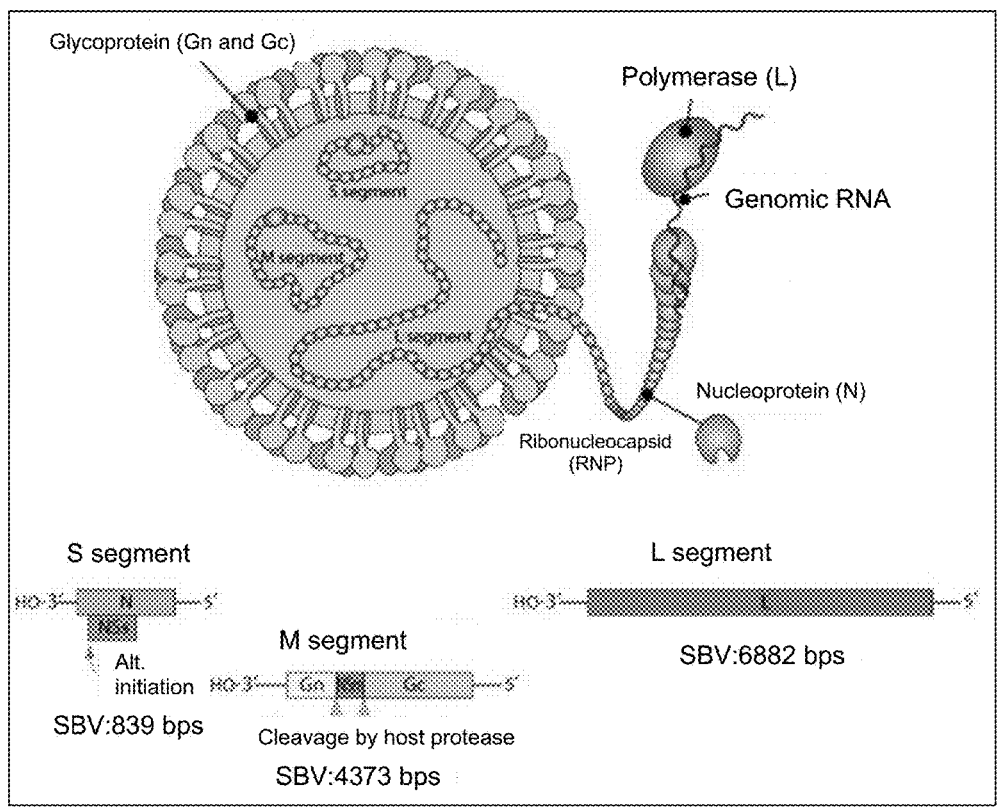
FIG. 1 depicts structure and genome organization of *Orthobunyaviruses* (Source: ViralZone 2010, Swiss Institute of Bioinformatics). The sizes of the SBV L, M and S segments are indicated.

Other objects, features and aspects of the present invention are disclosed in, or are obvious from, the following Detailed Description. It is to be understood by one of ordinary skill in the art that the present discussion is a description of exemplary embodiments only and is not intended as limiting the broader aspects of the present invention, which broader aspects are embodied in the exemplary construction. In fact, it will be apparent to those skilled in the art that various modifications and variations can be made in the present invention without departing from the scope or spirit of the invention. For instance, features illustrated or described as part of one embodiment can be used in another embodiment to yield a still further embodiment. It is intended that the present invention cover such modifications and variations as come within the scope of the appended claims and their equivalents. The contents of all references, published patents, and patents cited throughout the present application are hereby incorporated by reference in their entirety.

In a first aspect, the present disclosure provides vaccine compositions comprising SBV produced using a reverse genetic approach. The composition comprises nucleotides encoding S, M, and L viral segments. In an embodiment, the S, M, and L segments encode sequences having at least 90% homology to the sequences or reverse complementary sequences of those set forth in SEQ ID NO:3, 9, or 14.

In an embodiment, the disclosure provides an immunological composition comprising a Schmallenberg virus (SBV) or portion thereof. The composition may comprise SBV S, M, and L segments.

In an embodiment, the SBV comprises polynucleotides having at least 90% sequence identity to polynucleotides having the sequence as set forth in SEQ ID NO:3 (S segment); SEQ ID NO:9 (M segment); and SEQ ID NO:14 (L segment).

In an embodiment, the compositions comprise SBV comprising a polynucleotide complementary to a polynucleotide having at least 90% sequence identity to the polynucleotide having the sequences as set forth in SEQ ID NO:3 (S segment); SEQ ID NO:9 (M segment); and SEQ ID NO:14 (L segment). In another embodiment, the S segment encodes a peptide having at least 90% homology to SEQ ID NO:4; the M segment encodes a peptide having at least 90% homology to SEQ ID NO:10 or 11; and the L segment encodes a peptide having at least 90% homology to SEQ ID NO:15. In yet another embodiment, the S, M, and L segments encode peptides as set forth in SEQ ID NO:4, SEQ ID NOs:10 or 11, and SEQ ID NO:15, respectively.

In an embodiment, the composition is a vaccine composition, and further comprises a veterinarily and/or pharmaceutically acceptable carrier.

The disclosure also provides a reverse genetics (RG) system for producing the immunological or vaccine compositions comprising SV virus or viral sequences. The system may comprise one or more plasmids comprising nucleotides having at least 90% homology to the sequence of SEQ ID NO:3 (S segment); SEQ ID NO:9 (M segment); and SEQ ID NO:14 (L segment).

In an embodiment, the system of comprises nucleotides having the sequences as set forth in SEQ ID NOs:3, 9, and 14. The RG system may comprise 3 separate plasmids, wherein a first plasmid encodes the S segment, a second plasmid encodes the M segment, and a third plasmid encodes the L segment.

In another embodiment of the RG system, the S, M, and L segments may encode peptides as set forth in SEQ ID NOs:4 (S segment), 10 or 11 (M segment), and 15 (L segment).

In an embodiment of the RG system, the first plasmid encodes the SBV S segment 5' and 3' UTR, the second plasmid encodes the SBV M segment 5' and 3' UTR, and the third plasmid encodes the SBV L segment 5' and 3' UTR. In another embodiment, the first plasmid may comprise the sequences as set forth in SEQ ID NOs:2 & 3; the second plasmid may comprise the sequences as set forth in SEQ ID NOs: 8 & 12 or 13; and the third plasmid may comprise the sequences as set forth in SEQ ID NOs:13 & 16.

In another embodiment, the RG system plasmids comprise a T7 minimal promoter as set forth in SEQ ID NO:7 and a ribozyme/T7 terminator as set forth in SEQ ID NO:6.

The disclosure also provides for cDNA(s) useful for the production of the SBV compositions. The cDNA(s) may comprise nucleotides coding for SBV S, M, and L segments. The cDNA(s) may comprise nucleotides having at least 90% homology to the sequences as set forth in SEQ ID NO:3 (S segment); SEQ ID NO:9 (M segment); and SEQ ID NO:14 (L segment).

In an aspect, the disclosure provides isolated RNA molecules transcribed from the cDNA(s) used for producing the SB viruses and compositions. In an embodiment, the RNA molecules comprise sequence complementary to SEQ ID NO:3 (S segment); SEQ ID NO:9 (M segment); and SEQ ID NO:14 (L segment), or to sequences having at least 90% homology to the complementary sequences of those set forth in SEQ ID NO:3 (S segment); SEQ ID NO:9 (M segment); and SEQ ID NO:14 (L segment).

In another aspect, the disclosure provides a method for producing the SB viruses and compositions, comprising the steps of:
 a. producing a cDNA encoding each of the SBV segments (S, M, and L);
 b. co-transfecting the cDNAs into cells capable of producing the SBV from said cDNAs; and
 c. allowing the cells to make the virus, thereby producing the virus.

In an embodiment of the method, the cDNAs have the sequence as set forth in SEQ ID NO:3 (S segment); SEQ ID NO:9 (M segment); and SEQ ID NO:14 (L segment), or the sequence having at least 90% homology thereto.

In another embodiment of the method, the cells are BSR-T7/5 cells.

In still another aspect, the disclosure provides a method for providing an animal protection against SBV comprising the steps of administering the SB viruses and/or compositions to said animal, thereby providing the protection. The viruses or compositions may be administered as an IP or SC dose, and in a range of about 10 µg to about 300 µg per dose. In an embodiment, the protection lasts for at least about 1 year.

For convenience, certain terms employed in the Specification, Examples, and appended Claims are collected here.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

It is also noted that in this disclosure and particularly in the claims, terms such as "comprises", "comprised", "comprising" and the like can have the meaning attributed to such terms in U.S. Patent law; e.g., they can mean "includes", "included", "including", and the like; and that terms such as "consisting essentially of" and "consists essentially of" have the meaning ascribed to them by U.S. Patent law, e.g., they allow for elements not explicitly recited, but exclude elements that are found in the prior art or that affect a basic or novel characteristic of the invention.

As used herein, the term "animal" includes all vertebrate animals including humans. Animal or host includes mammals and human. The animal may be selected from the group consisting of equine (e.g., horse), canine (e.g., dogs, wolves, foxes, coyotes, jackals), feline (e.g., lions, tigers, domestic cats, wild cats, other big cats, and other felines including cheetahs and lynx), ovine (e.g., sheep), bovine (e.g., cattle), porcine (e.g., pig), caprine (e.g., goat), avian (e.g., chicken, duck, goose, turkey, quail, pheasant, parrot, finches, hawk, crow, ostrich, emu and cassowary), primate (e.g., prosimian, tarsier, monkey, gibbon, ape), and fish. The term "animal" also includes an individual animal in all stages of development, including embryonic and fetal stages.

As used herein, the term "virulent" means an isolate that retains its ability to be infectious in an animal host.

As used herein, the term "inactivated vaccine" means a vaccine composition containing an infectious organism or pathogen that is no longer capable of replication or growth. The pathogen may be bacterial, viral, protozoal or fungal in origin. Inactivation may be accomplished by a variety of methods including freeze-thawing, chemical treatment (for example, treatment with formalin), sonication, radiation, heat or any other convention means sufficient to prevent replication or growth of the organism while maintaining its immunogenicity.

As used herein, the term "immunogenicity" means capable of producing an immune response in a host animal against an antigen or antigens. This immune response forms the basis of the protective immunity elicited by a vaccine against a specific infectious organism.

As used herein, the term "immune response" refers to a response elicited in an animal. An immune response may refer to cellular immunity (CMI); humoral immunity or may involve both. The present invention also contemplates a response limited to a part of the immune system. For example, a vaccine composition of the present invention may specifically induce an increased gamma interferon response.

As used herein, the term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a protein, a polypeptide, a peptide, an epitope, a hapten, or any combination thereof. Alternately, the immunogen or antigen may comprise a toxin or antitoxin.

As used herein, the term "multivalent" means a vaccine containing more than one antigen whether from the same species (i.e., different isolates of SBV serotypes), from a different species (i.e., isolates from both bovine diarrhea virus and bovine BTV), or a vaccine containing a combination of antigens from different genera (for example, a vaccine comprising antigens from *leptospira* spp., BTV, lyme disease, and parainfluenza).

As used herein, the term "adjuvant" means a substance added to a vaccine to increase a vaccine's immunogenicity, as compared with its efficacy in absence of the adjuvant. The mechanism of how adjuvants operate is not entirely known. Some adjuvants are believed to enhance the immune response by slowly releasing the antigen, while other adjuvants are strongly immunogenic in their own right and are believed to function synergistically. Known vaccine adjuvants include, but are not limited to, oil and water emulsions (for example, complete Freund's adjuvant and incomplete Freund's adjuvant, and adjuvants disclosed in U.S. Pat. No. 7,371,395 to Merial Limited, which are herein incorporated by reference in their entirety), *Corynebacterium parvum*, Bacillus Calmette Guerin, aluminum hydroxide, glucan, dextran sulfate, iron oxide, sodium alginate, Bacto-Adjuvant, certain synthetic polymers such as poly amino acids and co-polymers of amino acids, saponin, "REGRESSIN" (Vetrepharm, Athens, Ga.), "AVRIDINE" (N, N-dioctadecyl-N',N'-bis(2-hydroxyethyl)-propanediamine), paraffin oil, muramyl dipeptide and the like.

As used herein, the term "emulsion" refers to a combination of at least two substances, wherein a first substance is dispersed in a second substance in which the first substance is insoluble. One example of an emulsion of the present invention is an oil phase dispersed in an aqueous phase.

As used herein, the terms "pharmaceutically acceptable carrier" and "pharmaceutically acceptable vehicle" are interchangeable and refer to a fluid vehicle for containing vaccine antigens that can be injected into a host without adverse effects. Suitable pharmaceutically acceptable carriers known in the art include, but are not limited to, sterile water, saline, glucose, dextrose, or buffered solutions. Carriers may include auxiliary agents including, but not limited to, diluents, stabilizers (i.e., sugars and amino acids), preservatives, wetting agents, emulsifying agents, pH buffering agents, viscosity enhancing additives, colors and the like.

As used herein, the term "vaccine composition" includes at least one antigen or immunogen in a pharmaceutically acceptable vehicle useful for inducing an immune response in a host. Vaccine compositions can be administered in dosages and by techniques well known to those skilled in the medical or veterinary arts, taking into consideration such factors as the age, sex, weight, species and condition of the recipient animal, and the route of administration. The route of administration can be percutaneous, via mucosal administration (e.g., oral, nasal, anal, vaginal) or via a parenteral route (intradermal, intramuscular, subcutaneous, intravenous, or intraperitoneal). Vaccine compositions can be administered alone, or can be co-administered or sequentially administered with other treatments or therapies. Forms of administration may include suspensions, syrups or elixirs, and preparations for parenteral, subcutaneous, intradermal, intramuscular or intravenous administration (e.g., injectable administration) such as sterile suspensions or emulsions. Vaccine compositions may be administered as a spray or mixed in food and/or water or delivered in admixture with a suitable carrier, diluent, or excipient such as sterile water, physiological saline, glucose, or the like. The compositions can contain auxiliary substances such as wetting or emulsifying agents, pH buffering agents, adjuvants, gelling or viscosity enhancing additives, preservatives, flavoring agents, colors, and the like, depending upon the route of administration and the preparation desired. Standard pharmaceutical texts, such as "Remington's Pharmaceutical Sciences," 1990 may be consulted to prepare suitable preparations, without undue experimentation.

The term "purified" as used herein does not require absolute purity; rather, it is intended as a relative term. Thus, for example, a purified immunogen preparation, such as protein or inactivated virus, is one in which the immunogen is more enriched than the immunogen is in its natural environment. An immunogen preparation is herein broadly referred to as "purified" such that the immunogen represents at least 60%, at least 70%, at least 80%, at least 90%, at least 95%, or at least 98%, of the total immunogen content of the preparation. A "crude preparation", which represents the lowest degree of purification, may contain as little as less than 60%, lest than 20%, less than 10%, less than 5%, or less than 1% of immunogenic components.

The term "highly purified" as used herein is intended to suggest a "higher degree of purity" as compared to the term "moderately purified". This "higher degree of purity" can include, but is in no way limited to, reduced percentages of contaminants, in an immunological preparation that has been "highly purified" versus an immunological preparation that has been "moderately purified". As discussed herein, "highly purified" immunological preparations will have the lowest to undetectable percentages of contaminants that can cause: reduced desired immune response, increased undesired immune response (e.g. hypersensitivity reaction), or reduced formulation stability. Similarly, an immunological preparation that has been "moderately purified" contains relatively reduced percentages of contaminants versus an immunological preparation that has been "minimally purified", which likewise, has reduced percentages of contaminants versus a preparation designated a "crude preparation".

Contaminants in an immunological preparation can include, but are in no way limited to, substances that contribute negatively to an immunological composition according to the present invention. One of several examples of a contaminant contributing negatively would be a contaminant that reduces the ability of an immunological composition of the present invention to elicit an immune response in animals.

Varying levels of purity (e.g. "highly purified", "moderately purified", and the like) can be achieved using various methods. For example, a combination of chromatography and size exclusion gel filtration can result in a "highly purified" or "moderately purified" immunological preparations. Differences in source/type of immunogens, as well as slight variations in purification procedures can significantly affect the final degree of immunogen purity. In general, as used herein, immunological preparations having the lowest to highest percentage of contaminants will be described as 1) "highly purified, 2) "moderately purified", 3) "minimally purified", 4) "crude preparation", respectively. A "highly purified" preparation will have the lowest level across all types of contaminants. A "moderately purified" preparation will have relatively low levels of most types of contaminants, but may have one type of contaminant in higher abundance than would be observed for a comparable "highly purified" preparation. Likewise, a "minimally purified preparation" will have relatively low levels of some types of contaminants, but may have more than one type of contaminant in higher abundance than a comparable "moderately purified" preparation. As expected, a "crude preparation" has the highest level of contaminants, across all contaminant types, as compared to the other types of preparations discussed herein.

A "polynucleotide" is a polymeric form of nucleotides of any length, which contain deoxyribonucleotides, ribonucleotides, and analogs in any combination. Polynucleotides may have three-dimensional structure, and may perform any function, known or unknown. The term "polynucleotide" includes double-, single-stranded, and triple-helical molecules. Unless otherwise specified or required, any embodiment of the invention described herein that is a polynucleotide encompasses both the double stranded form and each of two complementary forms known or predicted to make up the double stranded form of either the DNA, RNA or hybrid molecule.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracyl, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support.

An "isolated" polynucleotide or polypeptide is one that is substantially free of the materials with which it is associated in its native environment. By substantially free, is meant at least 50%, advantageously at least 70%, more advantageously at least 80%, and even more advantageously at least 90% free of these materials.

The invention further comprises a complementary strand to a SBV polynucleotide.

The complementary strand can be polymeric and of any length, and can contain deoxyribonucleotides, ribonucleotides, and analogs in any combination.

Hybridization reactions can be performed under conditions of different "stringency." Conditions that increase stringency of a hybridization reaction are well known. See for examples, "Molecular Cloning: A Laboratory Manual", second edition (Sambrook et al. 1989). Examples of relevant conditions include (in order of increasing stringency): incubation temperatures of 25° C., 37° C., 50° C., and 68° C.; buffer concentrations of 10×SSC, 6×SSC, 1×SSC, 0.1×SSC (where SSC is 0.15 M NaCl and 15 mM citrate buffer) and their equivalent using other buffer systems; formamide concentrations of 0%, 25%, 50%, and 75%; incubation times from 5 minutes to 24 hours; 1, 2 or more washing steps; wash incubation times of 1, 2, or 15 minutes; and wash solutions of 6×SSC, 1×SSC, 0.1×SSC, or deionized water.

The invention further encompasses polynucleotides encoding functionally equivalent variants and derivatives of a SBV polypeptides and functionally equivalent fragments thereof which may enhance, decrease or not significantly affect properties of the polypeptides encoded thereby. These functionally equivalent variants, derivatives, and fragments display the ability to retain SBV activity. For instance, changes in a DNA sequence that do not change the encoded amino acid sequence, as well as those that result in conservative substitutions of amino acid residues, one or a few amino acid deletions or additions, and substitution of amino acid residues by amino acid analogs are those which will not significantly affect properties of the encoded polypeptide. Conservative amino acid substitutions are glycine/alanine; valine/isoleucine/leucine; asparagine/glutamine; aspartic acid/glutamic acid; serine/threonine/methionine; lysine/arginine; and phenylalanine/tyrosine/tryptophan.

For the purposes of the present invention, sequence identity or homology is determined by comparing the sequences when aligned so as to maximize overlap and identity while minimizing sequence gaps. In particular, sequence identity may be determined using any of a number of mathematical algorithms. A non-limiting example of a mathematical algorithm used for comparison of two sequences is the algorithm of Karlin & Altschul, Proc. Natl. Acad. Sci. USA 1990; 87: 2264-2268, modified as in Karlin & Altschul, Proc. Natl. Acad. Sci. USA 1993; 90: 5873-5877.

Another example of a mathematical algorithm used for comparison of sequences is the algorithm of Myers & Miller, CABIOS 1988; 4: 11-17. Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Yet another useful algorithm for identifying regions of local sequence similarity and alignment is the FASTA algorithm as described in Pearson & Lipman, Proc. Natl. Acad. Sci. USA 1988; 85: 2444-2448.

Advantageous for use according to the present invention is the WU-BLAST (Washington University BLAST) version 2.0 software. WU-BLAST version 2.0 executable programs for several UNIX platforms can be downloaded from ftp://blast.wustl.edu/blast/executables. This program is based on WU-BLAST version 1.4, which in turn is based on the public domain NCBI-BLAST version 1.4 (Altschul & Gish, 1996, Local alignment statistics, Doolittle ed., Methods in Enzymology 266: 460-480; Altschul et al., Journal of Molecular Biology 1990; 215: 403-410; Gish & States, 1993; Nature Genetics 3: 266-272; Karlin & Altschul, 1993; Proc. Natl. Acad. Sci. USA 90: 5873-5877; all of which are incorporated by reference herein).

In general, comparison of amino acid sequences is accomplished by aligning an amino acid sequence of a polypeptide of a known structure with the amino acid sequence of a the polypeptide of unknown structure. Amino acids in the sequences are then compared and groups of amino acids that are homologous are grouped together. This method detects conserved regions of the polypeptides and accounts for amino acid insertions and deletions. Homology between amino acid sequences can be determined by using commercially available algorithms (see also the description of homology above). In addition to those otherwise mentioned herein, mention is made too of the programs BLAST, gapped BLAST, BLASTN, BLASTP, and PSI-BLAST, provided by the National Center for Biotechnology Information. These programs are widely used in the art for this purpose and can align homologous regions of two amino acid sequences.

In all search programs in the suite the gapped alignment routines are integral to the database search itself. Gapping can be turned off if desired. The default penalty (Q) for a gap of length one is Q=9 for proteins and BLASTP, and Q=10 for BLASTN, but may be changed to any integer. The default per-residue penalty for extending a gap (R) is R=2 for proteins and BLASTP, and R=10 for BLASTN, but may be changed to any integer. Any combination of values for Q and R can be used in order to align sequences so as to maximize overlap and identity while minimizing sequence gaps. The default amino acid comparison matrix is BLOSUM62, but other amino acid comparison matrices such as PAM can be utilized.

Alternatively or additionally, the term "homology" or "identity", for instance, with respect to a nucleotide or amino acid sequence, can indicate a quantitative measure of homology between two sequences. The percent sequence homology can be calculated as (Nref−Ndif)*100/Nref, wherein Ndif is the total number of non-identical residues in the two sequences when aligned and wherein Nref is the number of residues in one of the sequences. Hence, the DNA sequence AGTCAGTC will have a sequence identity of 75% with the sequence AATCAATC (Nref=8; Ndif=2).

Alternatively or additionally, "homology" or "identity" with respect to sequences can refer to the number of positions with identical nucleotides or amino acids divided by the number of nucleotides or amino acids in the shorter of the two sequences wherein alignment of the two sequences can be determined in accordance with the Wilbur and Lipman algorithm (Wilbur & Lipman, Proc Natl Acad Sci USA 1983; 80:726, incorporated herein by reference), for instance, using a window size of 20 nucleotides, a word length of 4 nucleotides, and a gap penalty of 4, and computer-assisted analysis and interpretation of the sequence data including alignment can be conveniently performed using commercially available programs (e.g., Intelligenetics™ Suite, Intelligenetics Inc. CA). When RNA sequences are said to be similar, or have a degree of sequence identity or homology with DNA sequences, thymidine (T) in the DNA sequence is considered equal to uracil (U) in the RNA sequence. Thus, RNA sequences are within the scope of the invention and can be derived from DNA sequences, by thymidine (T) in the DNA sequence being-considered equal to uracil (U) in RNA sequences.

And, without undue experimentation, the skilled artisan can consult with many other programs or references for determining percent homology.

A "vector" refers to a recombinant DNA or RNA plasmid or virus that comprises a heterologous polynucleotide to be delivered to a target cell, either in vitro or in vivo. The heterologous polynucleotide may comprise a sequence of interest for purposes of therapy, and may optionally be in the form of an expression cassette. As used herein, a vector need not be capable of replication in the ultimate target cell or subject. The term includes cloning vectors for translation of a polynucleotide encoding sequence. Also included are viral vectors.

The term "recombinant" means a polynucleotide of genomic cDNA, semisynthetic, or synthetic origin which either does not occur in nature or is linked to another polynucleotide in an arrangement not found in nature.

"Heterologous" means derived from a genetically distinct entity from the rest of the entity to which it is being compared. For example, a polynucleotide, may be placed by genetic engineering techniques into a plasmid or vector derived from a different source, and is a heterologous polynucleotide. A promoter removed from its native coding sequence and operatively linked to a coding sequence other than the native sequence is a heterologous promoter.

The polynucleotides of the invention may comprise additional sequences, such as additional encoding sequences within the same transcription unit, controlling elements such as promoters, ribosome binding sites, polyadenylation sites, additional transcription units under control of the same or a different promoter, sequences that permit cloning, expression, homologous recombination, and transformation of a host cell, and any such construct as may be desirable to provide embodiments of this invention.

Methods for making and/or administering a vector or recombinants or plasmid for expression of gene products of genes of the invention either in vivo or in vitro can be any desired method, e.g., a method which is by or analogous to the methods disclosed in, or disclosed in documents cited in: U.S. Pat. Nos. 4,603,112; 4,769,330; 4,394,448; 4,722,848; 4,745,051; 4,769,331; 4,945,050; 5,494,807; 5,514,375; 5,744,140; 5,744,141; 5,756,103; 5,762,938; 5,766,599; 5,990,091; 5,174,993; 5,505,941; 5,338,683; 5,494,807; 5,591,639; 5,589,466; 5,677,178; 5,591,439; 5,552,143; 5,580,859; 6,130,066; 6,004,777; 6,130,066; 6,497,883; 6,464,984; 6,451,770; 6,391,314; 6,387,376; 6,376,473; 6,368,603; 6,348,196; 6,306,400; 6,228,846; 6,221,362; 6,217,883; 6,207,166; 6,207,165; 6,159,477; 6,153,199; 6,090,393; 6,074,649; 6,045,803; 6,033,670; 6,485,729; 6,103,526; 6,224,882; 6,312,682; 6,348,450 and 6,312,683; U.S. patent application Ser. No. 920,197, filed Oct. 16, 1986; WO 90/01543; WO91/11525; WO 94/16716; WO 96/39491;

WO 98/33510; EP 265785; EP 0 370 573; Andreansky et al., Proc. Natl. Acad. Sci. USA 1996; 93:11313-11318; Ballay et al., EMBO J. 1993; 4:3861-65; Felgner et al., J. Biol. Chem. 1994; 269:2550-2561; Frolov et al., Proc. Natl. Acad. Sci. USA 1996; 93:11371-11377; Graham, Tibtech 1990; 8:85-87; Grunhaus et al., Sem. Virol. 1992; 3:237-52; Ju et al., Diabetologia 1998; 41:736-739; Kitson et al., J. Virol. 1991; 65:3068-3075; McClements et al., Proc. Natl. Acad. Sci. USA 1996; 93:11414-11420; Moss, Proc. Natl. Acad. Sci. USA 1996; 93:11341-11348; Paoletti, Proc. Natl. Acad. Sci. USA 1996; 93:11349-11353; Pennock et al., Mol. Cell. Biol. 1984; 4:399-406; Richardson (Ed), Methods in Molecular Biology 1995; 39, "Baculovirus Expression Protocols," Humana Press Inc.; Smith et al. (1983) Mol. Cell. Biol. 1983; 3:2156-2165; Robertson et al., Proc. Natl. Acad. Sci. USA 1996; 93:11334-11340; Robinson et al., Sem. Immunol. 1997; 9:271; and Roizman, Proc. Natl. Acad. Sci. USA 1996; 93:11307-11312. Thus, the vector in the invention can be any suitable recombinant virus or virus vector, such as a poxvirus (e.g., vaccinia virus, avipox virus, canarypox virus, fowlpox virus, raccoonpox virus, swinepox virus, etc.), adenovirus (e.g., canine adenovirus), herpesvirus, baculovirus, retrovirus, etc. (as in documents incorporated herein by reference); or the vector can be a plasmid.

It is understood to one of skill in the art that conditions for culturing a host cell varies according to the particular gene and that routine experimentation is necessary at times to determine the optimal conditions for culturing SBV depending on the host cell. A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof.

Polynucleotides comprising a desired sequence can be inserted into a suitable cloning or expression vector, and the vector in turn can be introduced into a suitable host cell for replication and amplification. Polynucleotides can be introduced into host cells by any means known in the art. The vectors containing the polynucleotides of interest can be introduced into the host cell by any of a number of appropriate means, including direct uptake, endocytosis, transfection, f-mating, electroporation, transfection employing calcium chloride, rubidium chloride, calcium phosphate, DEAE-dextran, or other substances; microprojectile bombardment; lipofection; and infection (where the vector is infectious, for instance, a retroviral vector). The choice of introducing vectors or polynucleotides will often depend on features of the host cell.

Advantageously, the pharmaceutical and/or therapeutic compositions and/or formulations according to the invention comprise or consist essentially of or consist of an effective quantity to elicit a therapeutic response of one or more expression vectors and/or polypeptides as discussed herein; and, an effective quantity can be determined from this disclosure, including the documents incorporated herein, and the knowledge in the art, without undue experimentation.

One skilled in the art can determine the effective plasmid dose to be used for each immunization or vaccination protocol and species from this disclosure and the knowledge in the art.

Also in connection with such a therapeutic composition, from the disclosure herein and the knowledge in the art, the skilled artisan can determine the number of administrations, the administration route, and the doses to be used for each injection protocol, without any undue experimentation.

In some embodiments, non-ionic hydrophilic surfactants having a high hydrophilic-lipophilic balance (HLB) value may be added to the disclosed formulations. This group comprises ethoxylated fatty acid monoesters of sorbitan (in particular 20 ethoxyl groups) (e.g. ethoxylated sorbitan monolaurate such as TWEEN 20®, ethoxylated sorbitan monopalmitate such as TWEEN 40®, ethoxylated sorbitan monostearate (such as TWEEN 60®, ethoxylated sorbitan monooleate such as TWEEN 80®, ethoxylated fatty alcohols (in particular 15-30 ethoxyl groups) (e.g. BRIJ 78®, BRIJ 98®, BRIJ 721®), ethoxylated fatty acids (in particular 15-30 ethoxyl groups) (e.g. MYRJ 49®, MYRJ 51®, MYRJ 52®, MYRJ 53®), non-ionic block-copolymers (e.g. polyoxyethylene/polyoxypropylene copolymer (POE-POP), such as LUTROL F127®, LUTROL F68®), and combinations thereof.

The disclosed formulation may include fatty acid esters of sorbitan (e.g. sorbitan monolaurate, like SPAN 20®, sorbitan monopalmitate, such as SPAN 40®, sorbitan monostearate, such as SPAN 60®, sorbitan tristearate, such as SPAN 65®, sorbitan monooleate, like SPAN 80®, sorbitan trioleate, like SPAN 85®, sorbitan monoisostearate, such as ARLACEL 987®, sorbitan isostearate, such as CRILL 6®), fatty acid esters of mannide (e.g. MONTANIDE 80®, mannide monooleate (such as ARLACEL A®), mannide dioleate, mannide trioleate, mannide tetraoleate), ethoxylated fatty acid esters of mannide (2, 3 or 4 ethoxyl groups) (e.g. MONTANIDE 888®, MONTANIDE 103®, ethoxylated mannide monooleate, ethoxylated mannide dioleate, ethoxylated mannide trioleate, ethoxylated mannide tetraoleate), and combinations thereof. The fatty acid may be oleate, palmitate, stearate, isostearate, laurate and combinations thereof.

In some embodiments, oils may be added to the disclosed formulations, including mineral oils, such as paraffin oil including isoparaffinic oil and/or naphtenic oil, squalane, pristane, polyisobutene oil, hydrogenated polyisobutene oil, polydecene oil, polyisoprene oil, polyisopropene oil and the like. Such oils may, for example, be those marketed under the name "MARCOL 52®" or "MARCOL 82®" (produced by Esso, France) or "DRAKEOL 6VR®" or "DRAKEOL 5®" "DRAKEOL 7®" (produced by Penreco, USA), "CLEAROL®" (produced by Sonneborn, USA), "Paraffin Oil Codex AAB2®" (produced by Aiglon, France), BLANDOL (produced by Sonneborn, USA), ONDINA 915 (produced by Shell, UK). The oil may also be a mixture of oils comprising at least 2 oils selected among the oils described herein, and in any proportion. The mixture of oils may also comprise at least one oil selected among the oils described above and at least one vegetable oil, and this vegetable oil represents from about 0.1% to about 33% of the oily phase, preferably from about 10% to about 25% v/v. These vegetable oils are unsaturated oils rich in oleic acid that are biodegradable and preferably liquid at the storage temperature (about +4° C.) or at least make it possible to give emulsions that are liquid at this temperature. For example the vegetable oil may be groundnut oil, nut oil, sunflower oil, safflower oil, soya oil, onager oil and the like.

The invention will now be further described by way of the following non-limiting examples.

EXAMPLES

Example 1

Complete SBV Genome Sequence and Comparison to Published Sequence

SBV was isolated from the brain of a malformed lamb and initially grown on BHK cells. Although cytopathic effect (cpe) was observed on BHK cells, the virus was lost upon passage of supernatant, so further virus production was carried out using Vero cells. The full genome sequence of the lamb isolate was determined by "next generation sequencing" (NGS) of passage #2 (Vero cells) using a single Miseq run. This analysis suggested (later confirmed, see below) that HE649912.1 (GenBank accession number), representing the L segment, lacks 12 nucleotides on the 3' untranslated region (UTR) and 6 nucleotides on the 5' UTR; HE649913.1, representing the M genome segment, lacks 12 nucleotides on the 3' UTR and a sequence duplication resulting from a sequencing artifact on the 5' UTR; HE649914.1, representing the S genome segment, lacks 54 nucleotides on the 5' UTR and 9 nucleotides on the 3' UTR.

In addition, four amino acid differences between cow blood (CB, FLI sequence) and lamb brain sequences (LB, sequence of instant disclosure) were identified in the L protein: H272Y; D487N; Y1019H; E1159D (Y, N, H, D corresponds to the LB sequence). A total of 12 amino acid differences were identified in the sequence of the glycoprotein precursor (GPC): C352R; T538A; N581I; H587D; N629Y; E690K; T737I; H738R; P739L; K746E; N1159D; K1340E. Some silent nucleotide differences were also identified (a potentially relevant silent mutation is detailed below).

Example 2

Infection of Sheep with SBV

Initial experiments were conducted to determine the virulence of the LB isolate in sheep. Since neither clinical signs nor viremia were detected, sheep were then inoculated with SBV isolated from bovine. Although no clinical signs were observed, viremia was detected by quantitative PCR. Subsequent experiments with sheep confirmed this finding and so the LB isolate was not pursued (recent sequencing results suggest that the LB isolate is an "atypical" SBV and that the sequence differences are not correlated with the host species).

Example 3

Sequence of SBV Isolated from Cattle Blood

The full genome sequence of SBV isolated at the CVI from cattle blood was determined by Illumina sequencing and was found to be highly similar to the (corrected) FLI sequence. The sequences of the S and L segments were identical. Two amino acid differences and one nucleotide difference in the 5' UTR were identified. The FLI sequence encodes lysines (K) at positions 746 and 1340, whereas the CVI sequence encodes glutamic acids (E) at these positions. It is possible the lysines present in the FLI sequence result from cell adaptation and that this could negatively influence virulence of the virus (i.e. attenuated virus). For this reason, the M genome segment from both FLI and instant isolates were synthesized.

Example 4

Reverse Genetics Production of SBV

The full genome sequences corresponding to the L, S and M sequences (in antigenomic orientation; and flanked by a minimal T7 promoter sequence on the 5' end and a hepatitis-δ ribozyme sequence and T7 terminator sequence on the 3' end), were synthesized by the GenScript Corporation. The sequences were cloned into pUC57 plasmids, resulting in pUC57-SBV-S, pUC57-SBV-L and pUC57-SBV-M. Two versions of pUC57-SBV-M were developed, one encoding the FLI sequence (referred to as M-Germ) and one encoding the CVI sequence (referred to as M-Neth).

Figure 2:
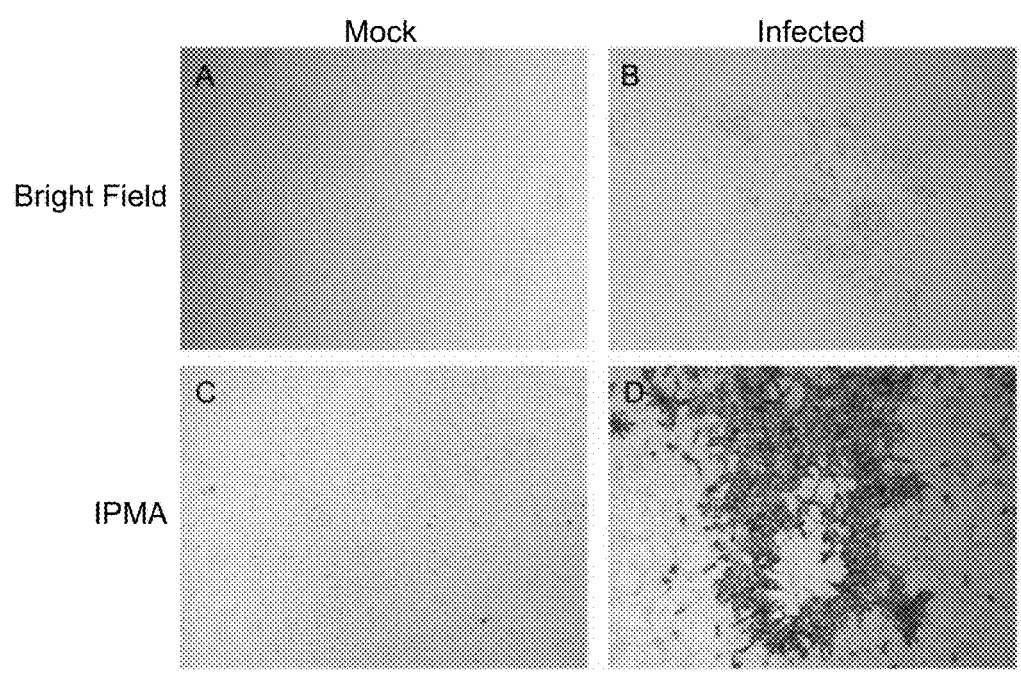
FIG. 2 is a bright-field micrograph of mock-infected Vero cells (A) and cells inoculated with SBV rescued on BSR-T7/5 cells (B). Mock-infected (C) and SBV-infected (D) Vero cells stained with an anti-SBV convalescent sheep serum.

Rescue of the viruses from cDNA was performed by co-transfection of plasmids pUC57-SBV-S, pUC57-SBV-M (Neth or Germ) and pUC57-SBV-L into BSR-T7/5 cells using JetPEI as the transfection reagent. Rescue of SBV-Germ was relatively straightforward. Transfection of the plasmids resulted in cytopathic effect (CPE) on BSR-T7/5 cells. Initial passaging was performed on BSR-T7/5 cells, but this resulted in loss of the virus (similar results were obtained with passage of field-collected isolates on BHK cells). Vero cells were also inoculated with the rescued virus, which resulted in clear CPE (FIG. 2B). Immunoperoxidase monolayer assays (IPMA) with a convalescent sheep serum confirmed that this cpe was caused by SBV (FIG. 2D).

Rescue of the SBV-Neth virus required considerably more effort, which is possibly explained by the putative cell-adaptive mutations present in the SBV-Germ virus. P1 stocks (rescued on BSR-T7/5 cells and passaged once on Vero cells) of both viruses are now available. Stocks SBV-Germ: 106.61 TCID$_{50}$/ml; SBV-Neth: 107.39 TCID$_{50}$/ml. The full genome sequences including flanking sequences are depicted in FIGS. 3-5.

Example 5

Efficacy of Reverse Genetics-Produced SBV Vaccine in Sheep

Objective.

Demonstrate the efficacy of different doses of SBV vaccine by vaccination/challenge in sero-negative lambs. Efficacy will be tested after one dose of vaccine and compared to a group of non-vaccinated age-matched lambs.

Materials and Methods.

Twenty conventional lambs, both males and females, less than 6 months of age at the time of vaccination. All lambs will be seronegative against SBV.

Vaccines.

Three batches of vaccine containing a low (L), medium (M) or high (H) dose of inactivated SBV antigen, respectively in the presence of ALSAP adjuvant (aluminum hydroxide+saponin+TS6 adjuvant described in U.S. Pat. No. 7,371,395).

Randomization and Vaccination.

At reception, all lambs will be randomized based on body weight to 4 groups (G1-G4) containing 5 lambs each. On D0, lambs from group G1, G2 and G3 will receive one dose of vaccine L, M or H, respectively by SQ administration on the thorax. Prior to vaccination, the injection site will be shaved and disinfected. Lambs from G4 will not be vaccinated and serve as negative controls.

Challenge and Follow-Up.

On D14, all lambs will be infected SQ with 1-3 ml of a suspension of a virulent strain of SBV. Lambs will be clinically examined (including rectal temperatures) for 14 days after challenge and blood will be collected on days 1-7, 10 and 14 after challenge and tested for the presence of SBV (viremia) by q-PCR Evaluation of Results.

Clinical signs and rectal temperatures will be described and discussed. Groups will be statistically compared to each other with respect to the amount of SBV detected in the blood following challenge expressed as the area under the curve.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A vaccine composition comprising a chemically-inactivated Schmallenberg virus (SBV) comprising SBV S, M and L segments encoded by the polynucleotides having the sequences as set forth in SEQ ID NO: 3, 9 and 14; and, an immuno-effective amount of aluminum hydroxide and saponin.

2. The composition of claim 1, further comprising a mineral oil and a surfactant.

3. The composition of claim 1, further comprising a veterinarily and/or pharmaceutically acceptable carrier.

4. A method for producing the SBV of claim 1, comprising the steps of:
   a. producing a cDNA encoding each of the SBV segments (S, M, and L);
   b. co-transfecting the cDNAs into cells capable of producing the SBV from said cDNAs; and
   c. allowing the cells to make the virus, thereby producing the virus.

5. The method of claim 4, wherein the cDNAs have the sequence as set forth in SEQ ID NO: 3 (S segment); SEQ ID NO:9 (M segment); and SEQ ID NO:14 (L segment).

6. The method of claim 4, wherein the cells are BSR-T7/5 cells.

7. A method for providing an animal protection against SBV comprising the steps of administering the composition of claim 1 to said animal, thereby providing the protection.

8. The method of claim 7, comprising the step of administering IP or CS about 10 μg to about 300 μg of the composition.

9. The method of claim 7, wherein protection lasts for at least about one year.

* * * * *